United States Patent
Ritchie et al.

(10) Patent No.: US 10,328,075 B2
(45) Date of Patent: Jun. 25, 2019

(54) METHOD OF TREATMENT AND COMPOUNDS FOR USE THEREIN

(71) Applicants: Baker Heart and Diabetes Institute, Melbourne, Victoria (AU); Monash University, Clayton, Victoria (AU)

(72) Inventors: Rebecca Helen Ritchie, McKinnon (AU); Cheng Xue Qin, Spotswood (AU); Arthur Christopoulos, Kew East (AU); Patrick Michael Sexton, Bundoora (AU); Jonathan Bayldon Baell, Parkville (AU)

(73) Assignees: Baker Heart and Diabetes Institute, Melbourne, Victoria (AU); Monash University, Clayton, Victoria (AU)

( * ) Notice: Subject to any disclaimer, the term of this patent is extended or adjusted under 35 U.S.C. 154(b) by 0 days.

(21) Appl. No.: 15/548,555

(22) PCT Filed: Feb. 4, 2016

(86) PCT No.: PCT/AU2016/050065
§ 371 (c)(1),
(2) Date: Aug. 3, 2017

(87) PCT Pub. No.: WO2016/123672
PCT Pub. Date: Aug. 11, 2016

(65) Prior Publication Data
US 2018/0092917 A1    Apr. 5, 2018

(30) Foreign Application Priority Data
Feb. 4, 2015    (AU) ................................ 2015900336

(51) Int. Cl.
*A61K 31/501*    (2006.01)
*A61K 31/50*    (2006.01)

(52) U.S. Cl.
CPC ............ *A61K 31/501* (2013.01); *A61K 31/50* (2013.01)

(58) Field of Classification Search
CPC .............................. A61K 31/501; A61K 31/50
USPC ..................................................... 514/252.03
See application file for complete search history.

(56) References Cited

FOREIGN PATENT DOCUMENTS

| WO | 03/074069 A2 | 9/2003 |
|----|----|----|
| WO | 2011/163502 A1 | 12/2011 |
| WO | 2012/074785 A1 | 6/2012 |
| WO | 2013/122953 A1 | 8/2013 |

OTHER PUBLICATIONS

Anderson et al. (2011) "2011 ACCF/AHA Focused Update Incorporated Into the ACC/AHA 2007 Guidelines for the Management of Patients With Unstable Angina/Non-ST-Elevation Myocardial Infarction a Report of the American College of Cardiology Foundation/American Heart Association Task Force on Practice Guidelines," Circulation. 123: e426-e579.
Armstrong et al. (2007) "Pexelizumab and the APEX AMI Trial," JAMA. 297:43-51.
Arumugam et al. (2009) "Toll-like receptors in ischemia-reperfusion injury," Shock. 32(1):4-16.
Berge et al. (1977) "Pharmaceutical salts," J. Pharm. Sci. 66:1-19.
Burli et al. (2006) "Potent hFPRL1 (ALXR) agonists as potential anti-inflammatory agents," Bioorg. Med. Chem. Lett. 16:3713-8.
Cha et al. (2008) "Cytokines link Toll-like receptor 4 signaling to cardiac dysfunction after global myocardial ischemia," Ann. Thorac. Surg. 85(5):1678-85.
Chao (2009) "Toll-like receptor signaling: a critical modulator of cell survival and ischemic injury in the heart," Am. J. Physiol. Heart Circ. Physiol. 296(1):H1-12.
Chen et al. (2010) "Sterile inflammation: sensing and reacting to damage," Nat. Rev. Immunol. 10(12):826-37.
Christopoulos et al. (2002) "G protein-coupled receptor allosterism and complexing," Pharmacol. Rev. 54:323-74.
Cilibrizzi et al. (2009) "6-methyl-2,4-disubstituted pyridazin-3(2H)-ones: a novel class of small-molecule agonists for formyl peptide receptors," J. Med. Chem. 52:5044-5057.
Cilibrizzi et al. (2012) "Synthesis, enantioresolution, and activity profile of chiral 6-methyl-2,4-disubstituted pyridazin-3(2H)-ones as potent N-formyl peptide receptor agonists," Bioorg. Med. Chem. 20:3781-3792.
Crocetti et al. (May 23, 2013) "Synthesis and Pharmacological Evaluation of New Pyridazin-Based Thioderivatives as Formyl Peptide Receptor (FPR) Agonists," Drug Dev. Res. 74:259-271.
Egleton et al. (1997) "Bioavailability and transport of peptides and peptide drugs into the brain," Peptides. 18:1431-1439.
Fleetwood et al. (2007) "Granulocyte-Macrophage Colony-Stimulating Factor (CSF) and Macrophage CSF-Dependent Macrophage Phenotypes Display Differences in Cytokine Profiles and Transcription Factor Activities: Implications for CSF Blockade in Inflammation," J. Immunol. 178:5245-5252.
Frangogiannis et al. (2008) "The immune system and cardiac repair," Pharmacol. Res. 58:88-111.
Gao et al. (2000) "Expression of active alpha(1B)-adrenergic receptors in the heart does not alleviate ischemic reperfusion injury," J. Mol. Cell. Cardiol. 32(9):1679-1686.
Gao et. al. (2011) "Deletion of macrophage migration inhibitory factor protects the heart from severe ischemia-reperfusion injury: a predominant role of anti-inflammation," J. Mol. Cell. Cardiol. 50(6):991-999.

(Continued)

*Primary Examiner* — Yevgeny Valenrod
(74) *Attorney, Agent, or Firm* — Brian C. Trinque; Lathrop Gage LLP

(57) ABSTRACT

The present invention relates generally to a method of therapeutically or prophylactically treating ischaemia-induced myocardial tissue damage, in particular ischaemia-reperfusion-induced myocardial tissue damage. More particularly, the present invention relates to a method of reducing the extent of ischaemia-induced myocardial tissue damage in a mammal by selectively upregulating FPR1-mediated ERK signalling. The method of the present invention is useful, inter alia, in reducing the extent and/or severity of myocardial tissue damage associated with conditions characterized by myocardial ischaemia or myocardial ischaemia and reperfusion, such as acute myocardial infarction caused by atherosclerotic artery occlusion or blood clot-induced artery occlusion.

22 Claims, 25 Drawing Sheets

(56) References Cited

OTHER PUBLICATIONS

Gavins (2010) "Are formyl peptide receptors novel targets for therapeutic intervention in ischaemia-reperfusion injury?" 31(6):266-276.

Giovannoni et al. (Apr. 8, 2013) "Further studies on 2-arylacetamide pyridazin-3(2H)-ones: design, synthesis and evaluation of 4,6-disubstituted analogs as formyl peptide receptors (FPRs) agonists," Eur. J. Med. Chem. 65:512-528.

Granger et al. (2003) "Pexelizumab, an anti-O5 complement antibody, as adjunctive therapy to primary percutaneous coronary intervention in acute myocardial infarction: the COMplement inhibition in Myocardial infarction treated with Angioplasty (COMMA) trial," Circulation. 108:1184-1190.

Huynh et al. (2012) "Coenzyme Q10 attenuates diastolic dysfunction, cardiomyocyte hypertrophy and cardiac fibrosis in the db/db mouse model of type 2 diabetes," Diabetologia. 55:1544-53.

Hwang et al. (2001) "Neutralization of interleukin-1beta in the acute phase of myocardial infarction promotes the progression of left ventricular remodeling," J. Am. Call. Cardiol. 38:1546-1553.

Irvine et al. (2012) "The soluble guanylyl cyclase activator bay 58/2667 selectively limits cardiomyocyte hypertrophy," PloS One. 7:e44481. pp. 1-11.

Irvine et al. (May 31, 2013) "HNO/cGMP-dependent antihypertrophic actions of isopropylamine-NONOate in heonatal rat cardiomyocytes: potential therapeutic advantages of HNO over NO," Am. J. Physiol. 305(3):H365-377.

Kenakin et al. (2012) "A simple method for quantifying functional selectivity and agonist bias," ACS Chem. Neurosci. 3:193-203.

Keov et al. (Jul. 8, 2014) "Molecular mechanisms of bitopic ligand engagement with the M1 muscarinic acetylcholine receptor," J .Biol. Chem. 289(34):23817-37.

Langer (1990) "New methods of drug delivery," Science. 249:1527-1533.

Le et al. (1999) "Utilization of two seven-transmembrane, G protein-coupled receptors, formyl peptide receptor-like 1 and formyl peptide receptor, by the synthetic hexapeptide WKYMVm for human phagocyte activation," J. Immunol. 163 (12):6777-84.

Lefer et al. (2000) "Oxidative stress and cardiac disease," Am. J. Med. 109:315-323.

Mahaffey et al. (2003) "Effect of pexelizumab, an anti-C5 complement antibody, as adjunctive therapy to fibrinolysis in acute myocardial infarction: the COMPlement inhibition in myocardial infarction treated with thromboLYtics (COMPLY) trial," Circulation. 108:1176-1183.

MNasoudi et al. (2008) "ACC/AHA 2008 statement on Performance Measurement and Reperfusion Therapy: a report of the ACC/AHA Task Force on Performance Measures (Work Group to address the challenges of Performance Measurement and Reperfusion Therapy)," J. Am. Coll. Cardiol. 52(24):2100-12.

May et al. (2010) "The effect of allosteric modulators on the kinetics of agonist-G protein-coupled receptor interactions in single living cells," Mol. Pharmacol. 78:511-23.

Monden et al. (2007) "Soluble TNF receptors prevent apoptosis in infiltrating cells and promote ventricular rupture and remodeling after myocardial infarction," Cardiovasc. Res. 73:794-805.

Prossnitz et al. (1997) "The N-formyl peptide receptor: a model for the study of chemoattractant receptor structure and function," Pharmacal. Ther. 74(1):73-102.

Stewart et al. (2009) "NO-sulindac inhibits the hypoxia response of PC-3 prostate cancer cells via the Akt signalling pathway," Int. J. Cancer. 124(1):223-232.

Sun et al. (2004) "Excessive tumor necrosis factor activation after infarction contributes to susceptibility of myocardial rupture and left ventricular dysfunction," Circulation. 110:3221-3228.

Suzuki et al. (2001) "Overexpression of interleukin-1 receptor antagonist provides cardioprotection against ischemia-reperfusion injury associated with reduction in apoptosis," Circulation. 104:I308-I313.

Tavener et al. (2006) "Cellular and molecular mechanisms underlying LPS-associated myocyte impairment," Am. J. Physiol. Heart Circ. Physiol. 290(2):H800-6.

Timmers et al. (2009) "Exenatide reduces infarct size and improves cardiac function in a porcine model of ischemia and reperfusion injury," J. Am. Call. Cardiol. 53:501-510.

Valant et al. (Mar. 11, 2014) "Separation of on-target efficacy from adverse effects through rational design of a bitopic adenosine receptor agonist," Proc. Natl. Acad. Sci. USA. 111(12):4614-19.

Ye et al. (2009) "International Union of Basic and Clinical Pharmacology. LXXIII. Nomenclature for the formyl peptide receptor (FPR) family," Pharmacal. Rev. 61(2):119-161.

International Search Report with Written Opinion corresponding to International Patent Application No. PCT/AU2016/050065, dated Mar. 16, 2016.

Qin et al. (2012) "Role of FPR1 Formyl Peptide Receptors in the Cardioprotective Actions of Annexin-A1 Against Ischaemia-Reperfusion (I-R) Injury," Heart, Lung and Circulation, vol. 21, Abstract 223, S92.

Extended European Search Report for European Patent Application No. 16746007.0, dated Oct. 19, 2018.

FIGURE 2
(A)
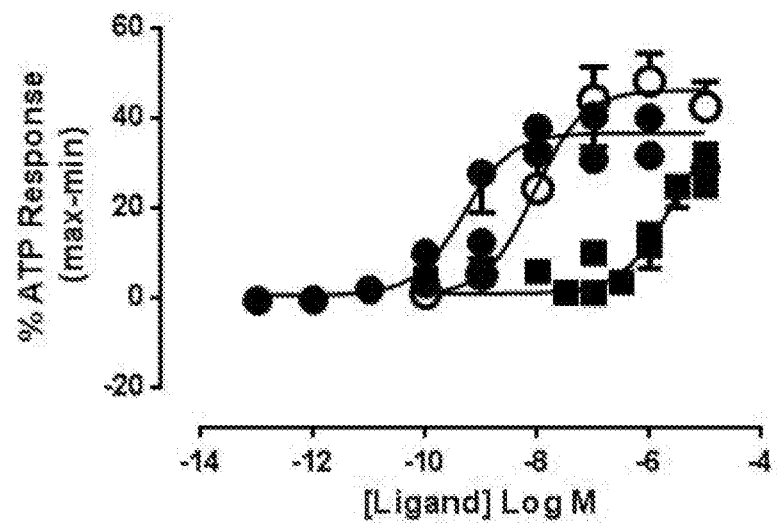
(B)
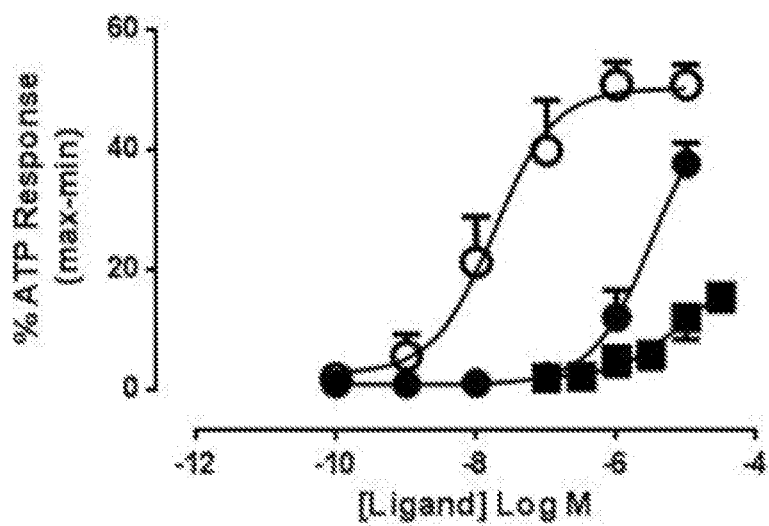

FIGURE 3
(A)
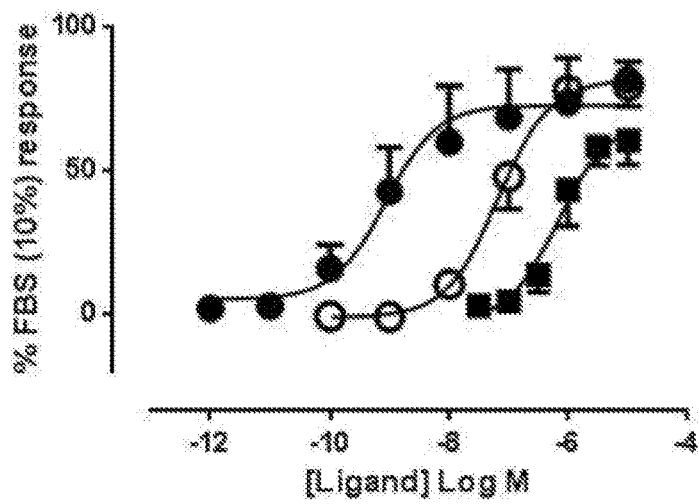
(B)
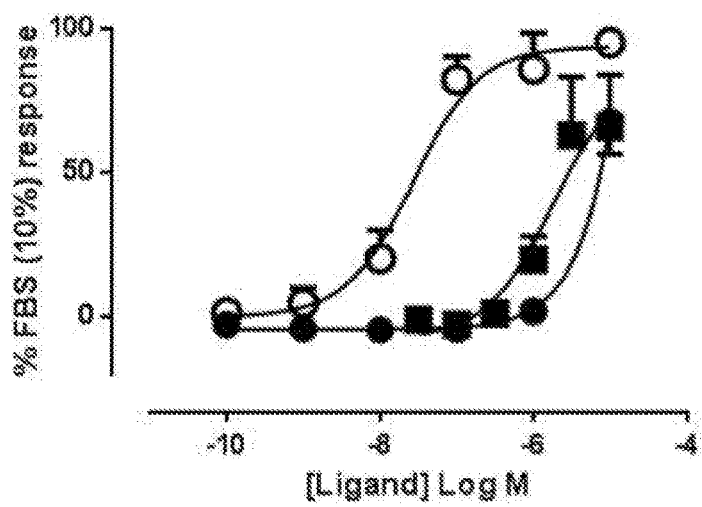

FIGURE 5
(A)
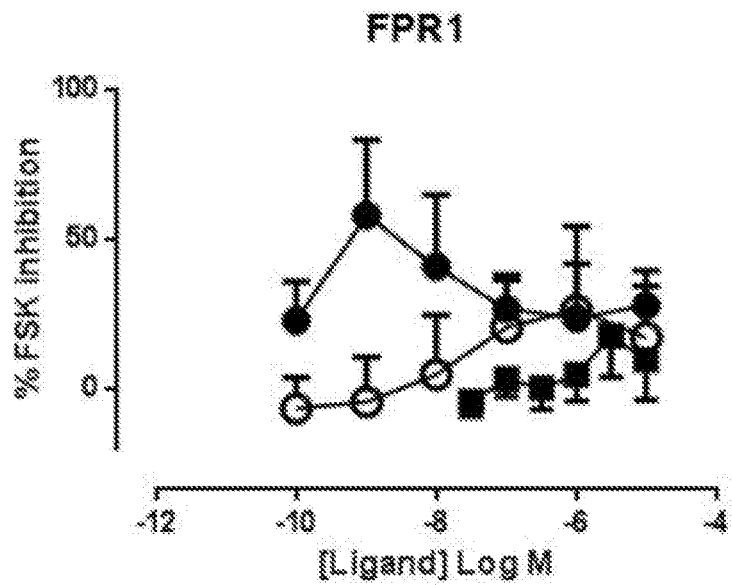
(B)
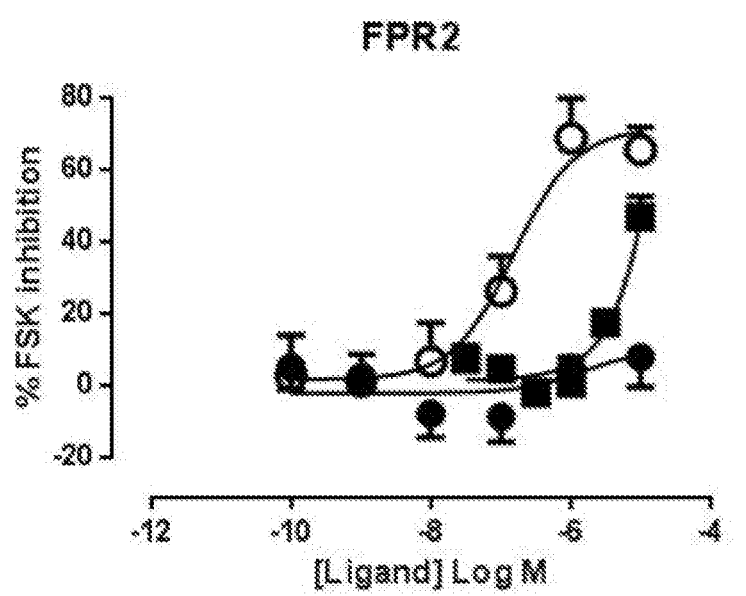

FIGURE 6
(A) FPR1
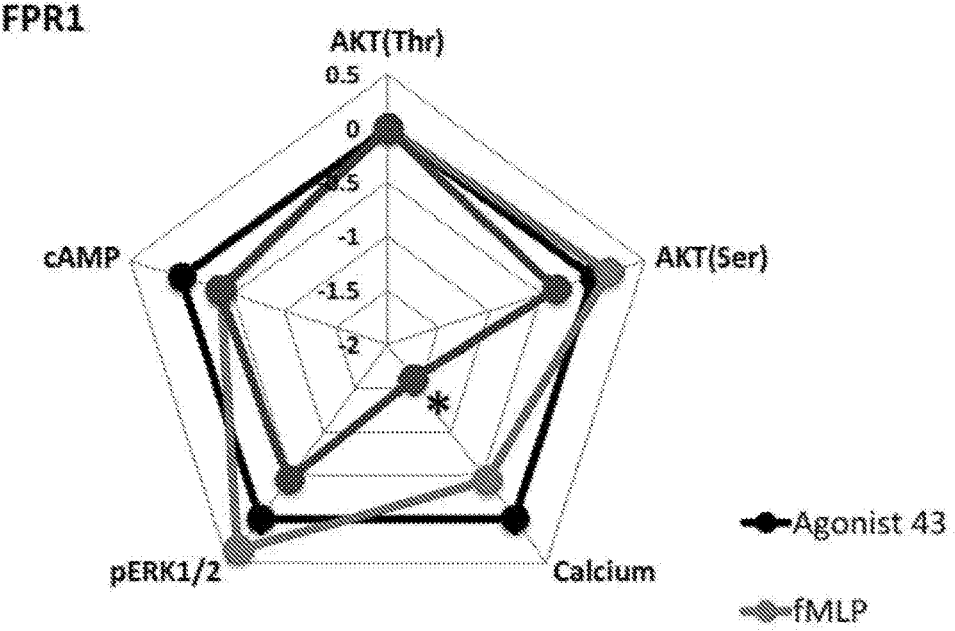
(B) FPR2
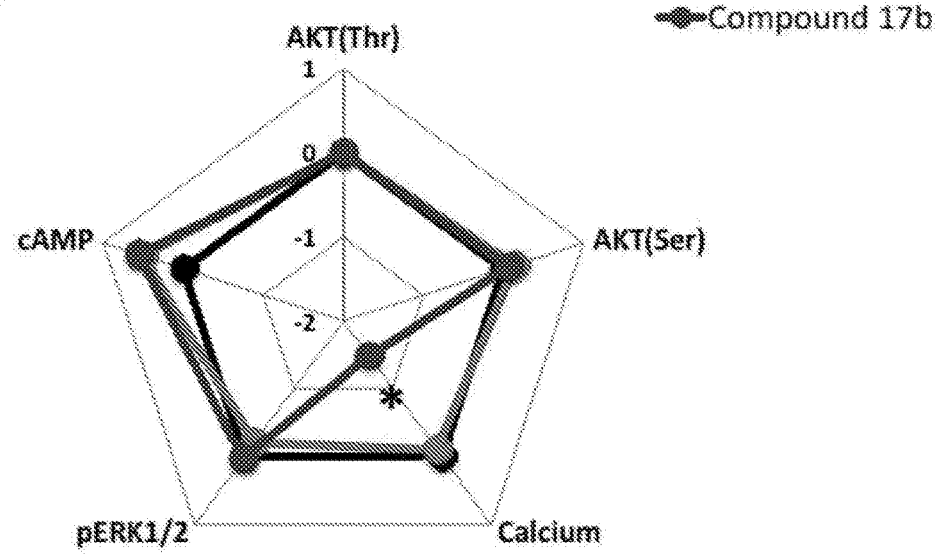

FIGURE 7
A)
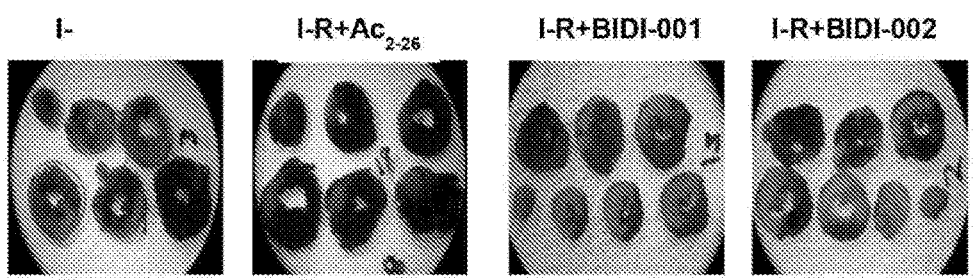
B)
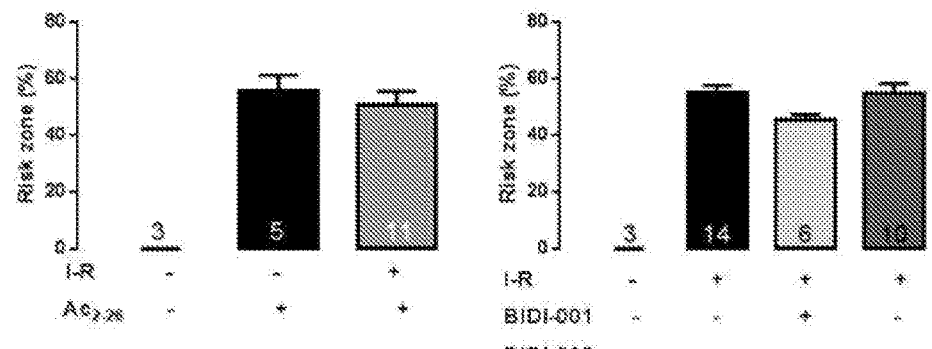
C)
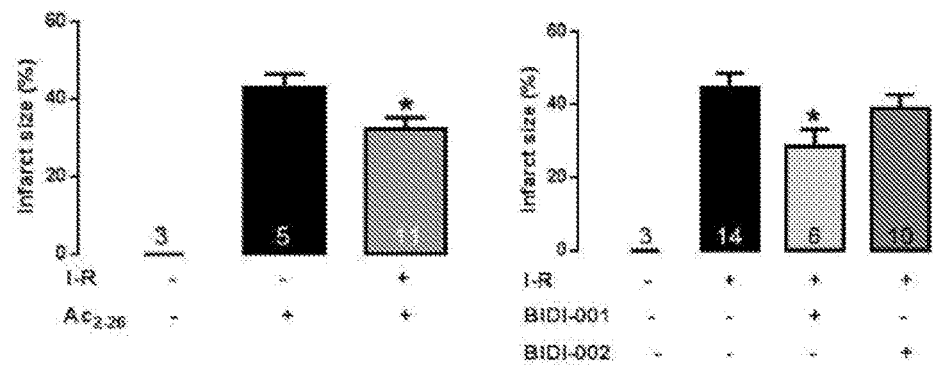
D)
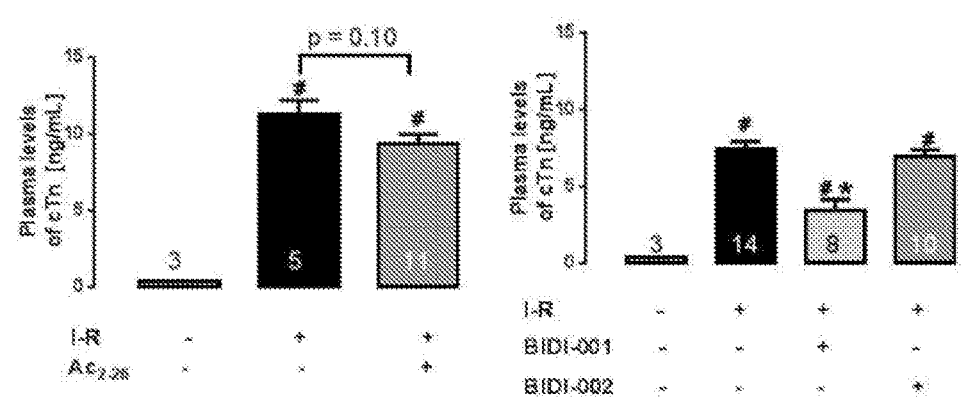

FIGURE 21
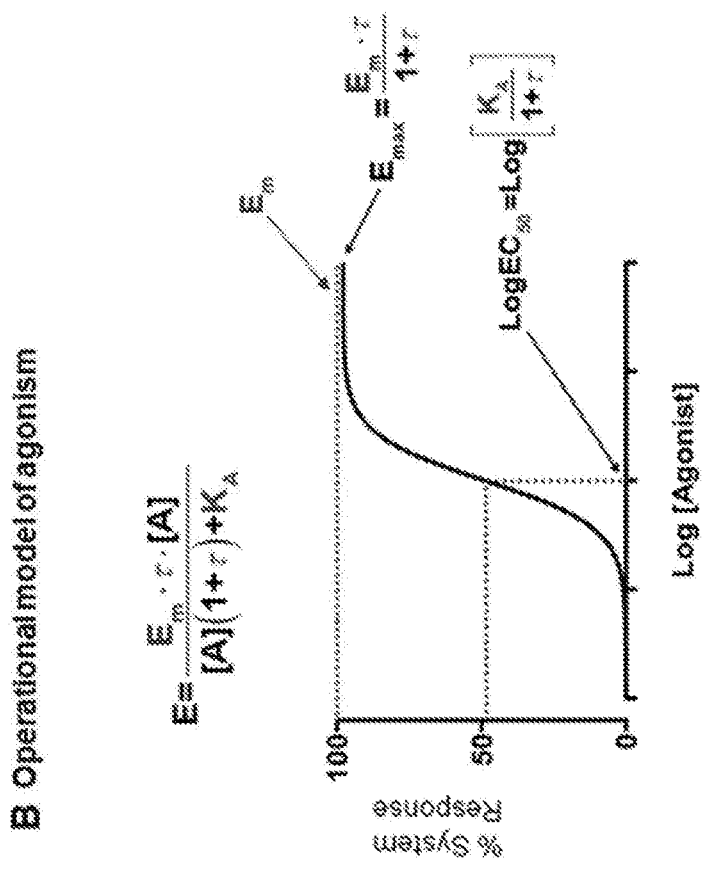
B Operational model of agonism
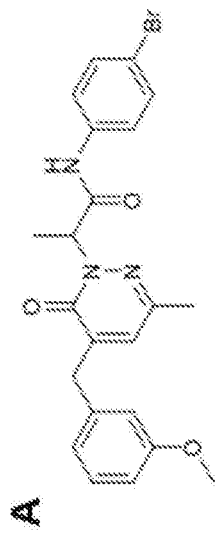
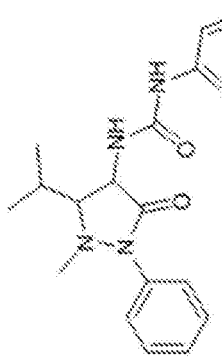

FIGURE 25
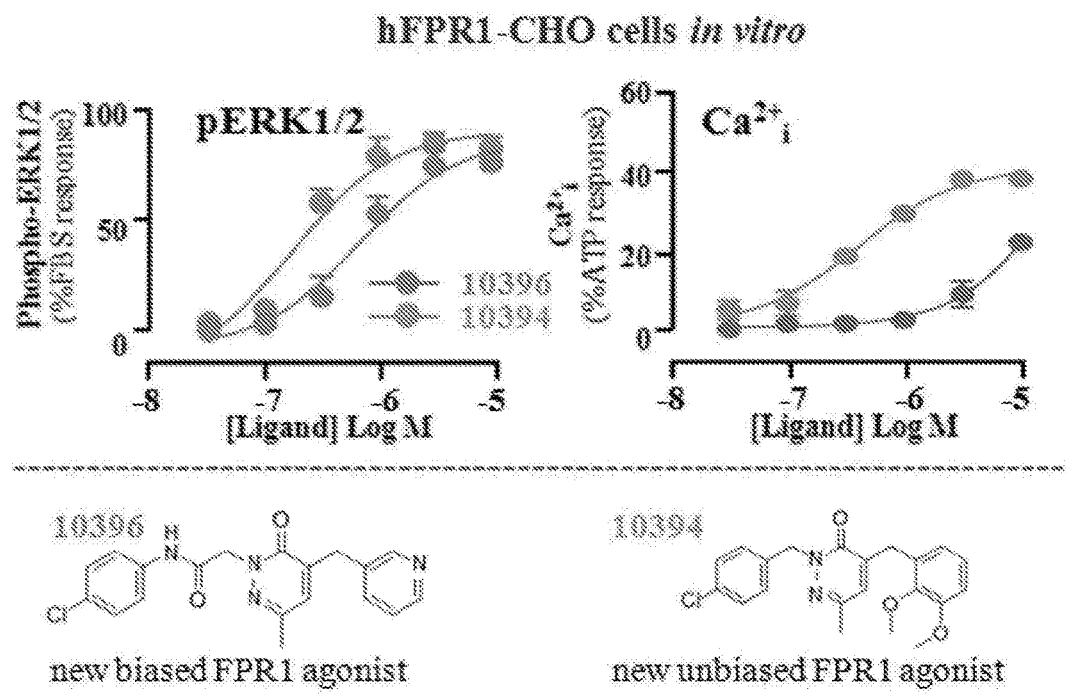
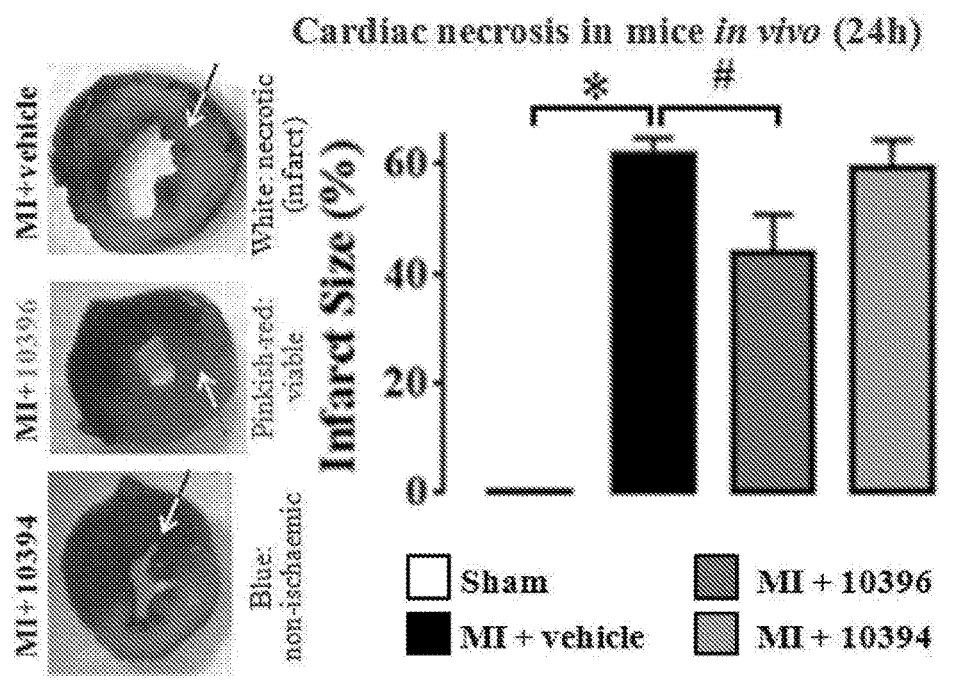

METHOD OF TREATMENT AND COMPOUNDS FOR USE THEREIN

FIELD OF THE INVENTION

This application is a 35 U.S.C. § 371 filing of International Application No. PCT/AU2016/050065, filed on Feb. 4, 2016, which claims priority to Australian Patent Application No. 2015900336, filed on Feb. 4, 2015, the contents of each of which are incorporated herein by reference in their entirety.

The present invention relates generally to a method of therapeutically or prophylactically treating ischaemia-induced myocardial tissue damage, in particular ischaemia-reperfusion-induced myocardial tissue damage. More particularly, the present invention relates to a method of reducing the extent of ischaemia-induced myocardial tissue damage in a mammal by selectively upregulating FPR1-mediated ERK signalling. The method of the present invention is useful, inter alia, in reducing the extent and/or severity of myocardial tissue damage associated with conditions characterised by myocardial ischaemia or myocardial ischaemia and reperfusion, such as acute myocardial infarction caused by atherosclerotic artery occlusion or blood clot-induced artery occlusion.

BACKGROUND OF THE INVENTION

Bibliographic details of the publications referred to by author in this specification are collected alphabetically at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Acute myocardial infarction (AMI) following coronary artery occlusion is the single largest cause of death in developed countries. Approximately 10% of patients die suddenly in the first few days due to arrhythmias or cardiac rupture, while 50% will develop heart failure within 2 years.

Occlusion of a coronary artery results in hypoxia and leads to cardiomyocyte necrosis, which initiates a complex response that can be considered in 3 phases: an initiation phase, an acute inflammatory phase and a repair phase (Frangogiannis, *Pharmacol Res.* 2008, 58:88-111). Ultimately, this process leads to fibrosis with left ventricular (LV) remodelling, a compensatory mechanism to maintain cardiac output. The deleterious effect of AMI on LV function is dependent not only on the size of the infarct but also on the balance of inflammation and repair.

Within minutes of ischaemia, the innate immune system is initiated by complement activation, expression of the Toll-like receptor 4 (TLR4) and generation of reactive oxygen species (ROS). In animal models, inhibition of complement reduces the inflammatory reaction and improves LV function, however these benefits have not been reproduced in human trials (Armstrong et al. 2007, *Jana* 297:43-51; Granger et al. *Circulation.* 2003, 108:1184-1190; Mahaffey et al. *Circulation.* 2003, 108:1176-1183). Prevention of the initiating phase by inhibition of TLR4 is also effective in animal models but not yet tested in humans (Timmers et al. 2009, *J Am Coll Cardiol.* 53:501-510). Targeting ROS is unlikely to be useful because ROS is generated within minutes of ischaemia (Lefer and Granger, *Am J Med.* 2000, 109:315-323).

The acute inflammatory phase begins within hours of ischaemia and is characterised by a cellular infiltrate of neutrophils and M1-like macrophages, together with a large number of 'pro-inflammatory' chemokines and cytokines. Neutrophils, which accumulate rapidly within the first 24 hours, are a rich source of matrix metalloproteinases (MMP) that assist clearance of dead cells and debris. M1-like macrophages are the other major cell type present during the acute inflammatory phase. Migration to the site of ischaemia is mediated by binding of CCR2 to high levels of MCP-1 (CCL2). Granulocyte-macrophage colony stimulating factor (GM-CSF) promotes production of inflammatory cytokines (TNF-α, IL-6 and IL-1β) by M1-like cells (Fleetwood et al. 2007, *J Immunol.* 178:5245-5252).

Several strategies to inhibit the inflammatory phase have been tested with varying success. Targeting specific inflammatory cytokines has produced mixed results. TNF-α-deficient mice had improved LV function after AMI, however, administration of an inhibitory soluble TNF receptor impaired LV function (Monden et al. 2007, *Cardiovasc Res.* 73:794-805; Sun et al. 2004, *Circulation.* 110:3221-3228). Similarly, inhibition of IL-1 has shown either beneficial or deleterious effects (Hwang et al. 2001, *J Am Coll Cardiol.* 38:1546-1553; Suzuki et al. 2001, *Circulation.* 104:I308-I303). These results suggest that targeting individual cytokines may not be useful.

The current treatments for patients with myocardial infarction are revascularization with thrombolytic agents or interventional procedures. These treatments have focused on restoring blood flow to the ischemic tissue to prevent tissue necrosis and preserve organ function. The most recent recommendations from the American Heart Association for patients presenting with myocardial infarction include fibrinolysis within the subsequent 30 minutes and primary percutaneous coronary intervention (PCI) by 90 minutes after patient presentation (Masoudi et al., 2008; Anderson et al., 2011). The introduction of therapies including aspirin, anti-platelet drugs, ACE inhibitors, ARBs, β-adrenoceptors antagonists, $Ca^{2+}$-channel antagonists, anti-thrombolytics, and glycoprotein (GP) IIb/IIIa inhibitors has improved outcomes post myocardial infarction. Although the majority of these pharmacotherapies remain in clinical use, myocardial infarction and resultant heart failure remains a major cause of death and disability.

The restoration of blood flow after a period of ischaemia, however, may elicit further myocardial damage, known as reperfusion injury. The manifestations of reperfusion injury include arrhythmias, myocardial stunning, microvascular dysfunction and incomplete recovery of contractile function, in addition to significant cardiomyocyte loss. It has been suggested that an overproduction of reactive oxygen species (ROS), intracellular $Ca^{2+}$ overload and inflammatory cell infiltration are the most important features of myocardial ischaemia-reperfusion (I-R) injury.

During reperfusion of ischemic myocardium, myocardial necrosis triggers a sterile inflammatory response through the release of endogenous molecules that have been designated as Damage-Associated Molecular Patterns (DAMPS) (Chen, G. Y. and G. Nunez, *Sterile inflammation: sensing and reacting to damage.* Nat Rev Immunol, 2010. 10(12): p. 826-37). These molecules are sensed by receptors that are also involved in microbial pathogen recognition and inflammatory response. One such group of receptors that have been implicated in myocardial ischaemia reperfusion injury are the Toll-like receptors (TLRs) (Arumugam, T. V., et al.,

*Toll-like receptors in ischemia-reperfusion injury.* Shock, 2009. 32(1): p. 4-16; Chao, W., *Toll-like receptor signaling: a critical modulator of cell survival and ischemic injury in the heart.* Am J Physiol Heart Circ Physiol, 2009. 296(1): p. H1-12). TLR4, the receptor for Gram negative bacterial cell wall component lipopolysaccharide (LPS), is expressed on cardiomyocytes and is responsible for LPS-induced myocardial dysfunction in endotoxaemia (Cha, J., et al., *Cytokines link Toll-like receptor 4 signaling to cardiac dysfunction after global myocardial ischemia.* Ann Thorac Surg, 2008. 85(5): p. 1678-85; Tavener, S. A. and P. Kubes, *Cellular and molecular mechanisms underlying LPS-associated myocyte impairment.* Am J Physiol Heart Circ Physiol, 2006. 290(2): p. H800-6).

Despite the understanding of the physiology of cardiac ischaemia-reperfusion injury, and even though there are interventions based on the basic pathogenesis of myocardial ischaemic-reperfusion injury, such as antioxidants and $Ca^{2+}$ channel blockers, clinical studies have shown limited success. Accordingly, methods of treating this condition both effectively and reproducibly, so as to reduce cardiac injury, have remained elusive. There is therefore an ongoing need to develop methods of treating patients who experience a myocardial ischaemia episode so as to minimise the myocardial tissue damage which is triggered by prolonged ischaemia, and which damage can be rendered still more severe when reperfusion occurs. The objective is to maintain and/or restore myocardial functionality both in terms of cardiomyocyte viability and contractile function.

To this end, the therapeutic potential of the glucocorticoid (GC)-regulated anti-inflammatory mediator annexin-A1 (ANX-A1) has recently been recognised in a range of systemic inflammatory disorders. ANX-A1 binds to and activates the family of formyl peptide receptors (FPRs), which are members of the seven transmembrane G protein-coupled receptor (GPCR) family, to inhibit neutrophil activation, migration and infiltration.

The FPR2 member of the human FPR family (also comprising FPR1, and FPR3) is now identified as the receptor responsible for some of the biological activities of ANX-A1, its N-terminal peptide and $LxA_4$ (Ye et al., 2009) and a large number of other ligands. The FPR1 and FPR2 receptors are widely distributed in tissues and different cell types, being most prominently expressed on cell types involved with inflammatory processes, whereas FPR3 is thought to be highly expressed only in dendritic cells. FPR2 and FPR3 however share ≥70% level of sequence homolog (Ye et al, 2009). Studies on the cardioprotective actions of ANX-A1 and its peptide mimetics (Ac2-26, CGEN-855A) have largely focused on its anti-inflammatory effects as a mechanism of preserving myocardial viability following I-R injury. However, there is also now evidence of the direct protective action of ANX-A1 on myocardium, independently of inflammatory cells in vitro. The ability of ANX-A1 to preserve both cardiomyocyte viability and contractile function, in addition to reducing neutrophil infiltration (anti-inflammation) has therefore highlighted the potential therapeutic utility of ANX-A1 as a clinical approach to improving outcomes after myocardial infarction. Nevertheless, this approach is still undergoing extensive research and its approach is not yet deployed in the clinic. Accordingly, the need for development of new treatment regimes for use with myocardial I-R injury is ongoing.

It has been observed that although the ANX-A1-FPR2 interaction exemplifies one possible means of treating myocardial infarction patients, there are still unwanted side effects associated with this interaction. In particular, FPR-mediated signalling can lead to localised $Ca^{2+}$ overload in a reperfused tissue and thereby the induction of cell death. In work leading up to the present invention, however, an FPR agonist has been identified which unexpectedly exhibits highly selective functionality in terms of inducing FPR-mediated signalling. Specifically, in addition to selectively inducing FPR1 signalling (as opposed to FPR2 signalling), the compounds of the present invention also effect a functional bias in that only the FPR1-ERK/Akt mediated signalling pathways are upregulated, which, surprisingly, selectively activates cardiomyocyte survival mechanisms without the concomittant activation of intracellular $Ca^{2+}$ mobilisation that is usually observed with FPR activation. Still further, FPR1 mediated signalling has been determined to effect not just the restoration of cardiomyocyte contractile function, but also the preservation of cardiomyocyte viability thereby providing not just an effective alternative to ANX-A1/FPR2-related cardiomyocyte survival effects, but, in fact, a significantly improved effector mechanism which, unlike FPR2 activation, permits selective upregulation of only ERK/Akt signalling and not intracellular $Ca^{2+}$ mobilisation. Accordingly, the present invention provides unexpected and superior outcomes relative to what was previously known in relation to treating myocardial infarction, and in particular ischaemia-reperfusion injury, via the selective upregulation of FPR1-ERK/Akt signalling. The present invention has therefore enabled the development of a treatment method in respect of which the undesirable side effect of $Ca^{2+}$ overload and potentially also Ca2+-triggered pro-inflammatory effects have been minimised, while nevertheless upregulating myocardial contractile function and viability, using a single compound which both selectively upregulates FPR1 activity and also skews the induced receptor signal to a cytoprotective ERK/Akt-mediated response.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The symbol "—" means a single bond, and "=" means a double bond. When chemical structures are depicted or described, unless explicitly stated otherwise, all carbons are assumed to have hydrogen substitution to conform to a valence of four. It is understood by one of ordinary skill in the art that the aforementioned descriptive techniques are common in the chemical arts to provide brevity and simplicity to description of otherwise complex structures.

If a group "R" is depicted as "floating" on a ring system, as for example in the formula:

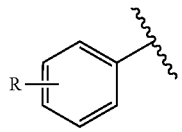

then, unless otherwise defined, a substituent "R" may reside on any atom of the ring system, assuming replacement of a depicted, implied, or expressly defined hydrogen from one of the ring atoms, so long as a stable structure is formed.

One aspect of the present invention is directed to a method of minimising the extent of ischaemia-induced myocardial tissue damage in a mammal, said method comprising administering to said mammal an effective amount of a compound of structure (I):

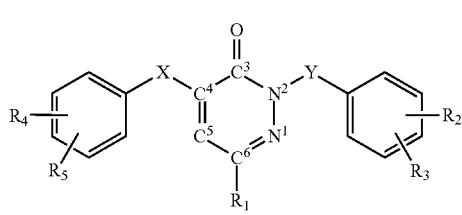

(I)

or a pharmaceutically acceptable salt, solvate or stereoisomer thereof, wherein
(a) X is $CH_2$;
  Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
    wherein $R_6$ is H;
    $R_7$ is $CH_3$, $C_2H_5$, n-$C_3H_7$, i-$C_3H_7$, n-$C_4H_9$, or $C_6H_5$;
    or
    $R_6$ is $CH_3$;
    $R_7$ is $C_2H_5$ or $CH_3$; and
  $R_1$ is $CH_3$;
or
(b) X is $CH_2$;
  Y is $CH_2CONH$; and
  $R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or
(c) X is NHCO or NHCONH;
  Y is $CH_2$; and
  $R_1$ is $CH_3$;
or
(d) X is NH;
  Y is $CH_2CONH$; and
  $R_1$ is $CH_3$;
or
(e) X is NHCO or CO;
  Y is $CH_2CONH$; and
  $R_1$ is $CH_3$;
or
(f) X is $CH_2$;
  Y is $CH_2CO$;
    wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and
  $R_1$ is $CH_3$;
or
(g) X is NHCONH, NHCO, or NH;
  Y of structure (I) is not present and instead the phenyl group substituted with $R_2$ and $R_3$ is directly bonded to the N2 of the pyridazinone ring; and
  $R_1$ is $CH_3$;
or
(h) X is $CH_2$;
  Y is $CH_2CONH$ or $CH(CH_3)CONH$;
    the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and
  $R_1$ is $CH_3$;
or
(i) X and the phenyl group substituted with $R_4$ and $R_5$ are not present;
  Y is $CH_2CONH$; and
  $R_1$ is $CH_3$;
or
(j) X and the phenyl group substituted with $R_4$ and $R_5$ are not present;
  Y is $CH_2CONH$;
  $R_1$ is $CH_3$; and
    the bond between C4 and C5 of the pyridazinone ring is a single bond;
or
(k) X is $NH_2$ and the phenyl group substituted with $R_4$ and $R_5$ is not present;
  Y is $CH_2CONH$; and
  $R_1$ is $CH_3$;
or
(l) X of structure (I) is not present and instead the phenyl group substituted with $R_4$ and $R_5$ is directly bonded to C4 of the pyridazinone ring;
  Y is $CH_2CONH$; and
  $R_1$ is $CH_3$;
or
(m) X is NH;
  Y is $CH_2CONH$;
  $R_1$ is $CH_3$; and
    C5 is additionally substituted with $COCH_3$;
  wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group; and
wherein said compound is administered for a time and under conditions sufficient for said agent to induce cardiomyocyte FPR1 activation.

In another aspect there is provided a method of minimising the extent of ischaemia-induced myocardial tissue damage in a mammal, said method comprising administering to said mammal an effective amount of a compound of structure (I):

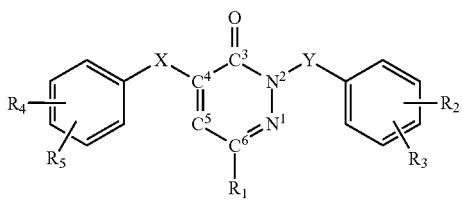

or a pharmaceutically acceptable salt, solvate or stereoisomer thereof, wherein (a) X is $CH_2$;
Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
wherein $R_6$ is H;
$R_7$ is $CH_3$, $C_2H_5$, n-$C_3H_7$, i-$C_3H_7$, n-$C_4H_9$, or $C_6H_5$;
or
$R_6$ is $CH_3$;
$R_7$ is $C_2H_5$ or $CH_3$; and
$R_1$ is $CH_3$;
or
(b) X is $CH_2$;
Y is $CH_2CONH$; and
$R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or
(c) X is NHCO or NHCONH;
Y is $CH_2$; and
$R_1$ is $CH_3$;
or
(d) X is NH;
Y is $CH_2CONH$; and
$R_1$ is $CH_3$;
or
(e) X is NHCO or CO;
Y is $CH_2CONH$; and
or
(f) X is $CH_2$;
Y is $CH_2CO$;
wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and
$R_1$ is $CH_3$;
or
(g) X is NHCONH, NHCO, or NH;
Y of structure (I) is not present and instead the phenyl group substituted with $R_2$ and $R_3$ is directly bonded to the N2 of the pyridazinone ring; and
$R_1$ is $CH_3$;
or
(h) X is $CH_2$;
Y is $CH_2CONH$ or $CH(CH_3)CONH$;
the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and $R_1$ is $CH_3$;
or
(i) X and the phenyl group substituted with $R_4$ and $R_5$ are not present;
Y is $CH_2CONH$; and
$R_1$ is $CH_3$;
or
(j) X and the phenyl group substituted with $R_4$ and $R_5$ are not present;
Y is $CH_2CONH$;
$R_1$ is $CH_3$; and
the bond between C4 and C5 of the pyridazinone ring is a single bond;
or
(k) X is $NH_2$ and the phenyl group substituted with $R_4$ and $R_5$ is not present;
Y is $CH_2CONH$; and
$R_1$ is $CH_3$;
or
(l) X of structure (I) is not present and instead the phenyl group substituted with $R_4$ and $R_5$ is directly bonded to C4 of the pyridazinone ring;
Y is $CH_2CONH$; and
$R_1$ is $CH_3$;
or
(m) X is NH;
Y is $CH_2CONH$;
$R_1$ is $CH_3$; and
C5 is additionally substituted with $COCH_3$;
wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group; and
wherein said compound is administered for a time and under conditions sufficient for said agent to induce cardiomyocyte FPR1 activation and wherein said tissue damage is loss of cellular viability and contractile function.

Yet another aspect of the present invention provides a method of minimising the extent of myocardial infarction related tissue damage in a mammal, said method comprising administering to said mammal an effective amount of a compound of structure (I):

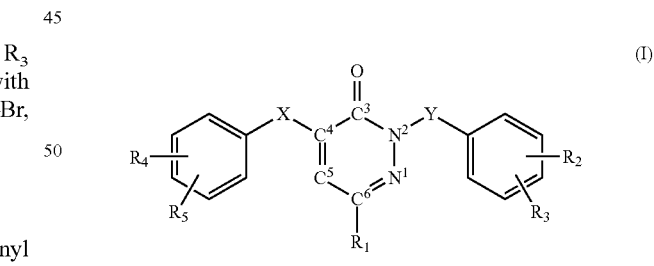

or a pharmaceutically acceptable salt, solvate or stereoisomer thereof, wherein
(a) X is $CH_2$;
Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
wherein $R_6$ is H;
$R_7$ is $CH_3$, $C_2H_5$, n-$C_3H_7$, i-$C_3H_7$, n-$C_4H_9$, or $C_6H_5$;
or
$R_6$ is $CH_3$;
$R_7$ is $C_2H_5$ or $CH_3$; and $R_1$ is $CH_3$;
or
(b) X is $CH_2$;
Y is $CH_2CONH$; and
$R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or
(c) X is NHCO or NHCONH;
Y is $CH_2$; and
$R_1$ is $CH_3$;
or
(d) X is NH;
Y is $CH_2CONH$; and
$R_1$ is $CH_3$;
or
(e) X is NHCO or CO;
Y is $CH_2CONH$; and
$R_1$ is $CH_3$;
or
(f) X is $CH_2$;
Y is $CH_2CO$;
wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and
$R_1$ is $CH_3$;
or
(g) X is NHCONH, NHCO, or NH;
Y of structure (I) is not present and instead the phenyl group substituted with $R_2$ and $R_3$ is directly bonded to the N2 of the pyridazinone ring; and
$R_1$ is $CH_3$;
or
(h) X is $CH_2$;
Y is $CH_2CONH$ or $CH(CH_3)CONH$;
the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and
$R_1$ is $CH_3$;
or
(i) X and the phenyl group substituted with $R_4$ and $R_5$ are not present;
Y is $CH_2CONH$; and
$R_1$ is $CH_3$;
or
(j) X and the phenyl group substituted with $R_4$ and $R_5$ are not present;
Y is $CH_2CONH$;
$R_1$ is $CH_3$; and
the bond between C4 and C5 of the pyridazinone ring is a single bond;
or
(k) X is $NH_2$ and the phenyl group substituted with $R_4$ and $R_5$ is not present;
Y is $CH_2CONH$; and
$R_1$ $CH_3$;
(l) X of structure (I) is not present and instead the phenyl group substituted with $R_4$ and $R_5$ is directly bonded to C4 of the pyridazinone ring;
Y is $CH_2CONH$; and
$R_1$ is $CH_3$;
or
(m) X is NH;
Y is $CH_2CONH$;
$R_1$ is $CH_3$; and
C5 is additionally substituted with $COCH_3$;
wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group; and
wherein said compound is administered for a time and under conditions sufficient for said agent to induce cardiomyocyte FPR1 activation.

Still another aspect of the present invention is directed to a method of minimising the extent of ischaemia-reperfusion-induced myocardial tissue damage in a mammal, said method comprising administering to said mammal an effective amount of a compound of structure (I):

$$\text{(I)}$$

or a pharmaceutically acceptable salt, solvate or stereoisomer thereof, wherein
(a) X is $CH_2$;
Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
wherein $R_6$ is H;
$R_7$ is $CH_3$, $C_2H_5$, n-$C_3H_7$, i-$C_3H_7$, n-$C_4H_9$, or $C_6H_5$;
or
$R_6$ is $CH_3$;
$R_7$ is $C_2H_5$ or $CH_3$; and
$R_1$ is $CH_3$;
or
(b) X is $CH_2$;
Y is $CH_2CONH$; and
$R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or
(c) X is NHCO or NHCONH;
Y is $CH_2$; and
$R_1$ is $CH_3$;
or
(d) X is NH;
Y is $CH_2CONH$; and
$R_1$ is $CH_3$;
or
(e) X is NHCO or CO;
Y is $CH_2CONH$; and
$R_1$ is $CH_3$;
or
(f) X is $CH_2$;
Y is $CH_2CO$;
wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and $R_1$ is $CH_3$;

or (g) X is NHCONH, NHCO, or NH;
Y of structure (I) is not present and instead the phenyl group substituted with $R_2$ and $R_3$ is directly bonded to the N2 of the pyridazinone ring; and
$R_1$ is $CH_3$;

or (h) X is $CH_2$;
Y is $CH_2CONH$ or $CH(CH_3)CONH$;
the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and
$R_1$ is $CH_3$;

or (i) X and the phenyl group substituted with $R_4$ and $R_5$ are not present;
Y is $CH_2CONH$; and
$R_1$ is $CH_3$;

or (j) X and the phenyl group substituted with $R_4$ and $R_5$ are not present;
Y is $CH_2CONH$;
$R_1$ is $CH_3$; and
the bond between C4 and C5 of the pyridazinone ring is a single bond;

or (k) X is $NH_2$ and the phenyl group substituted with $R_4$ and $R_5$ is not present;
Y is $CH_2CONH$; and
$R_1$ is $CH_3$;

or (l) X of structure (I) is not present and instead the phenyl group substituted with $R_4$ and $R_5$ is directly bonded to C4 of the pyridazinone ring;
Y is $CH_2CONH$; and
$R_1$ is $CH_3$;

or (m) X is NH;
Y is $CH_2CONH$;
$R_1$ is $CH_3$; and
C5 is additionally substituted with $COCH_3$;

wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group; and wherein said compound is administered for a time and under conditions sufficient for said agent to induce cardiomyocyte FPR1 activation.

In yet still another aspect there is provided a method of therapeutically or prophylactically treating a condition characterised by ischaemia-induced myocardial tissue damage or ischaemia-reperfusion-induced myocardial tissue damage in a mammal, said method comprising administering to said mammal an effective amount of a compound of structure (I):

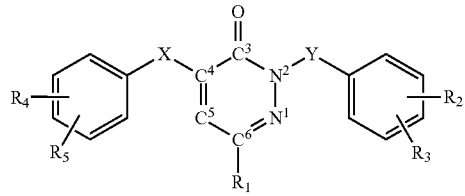

or a pharmaceutically acceptable salt, solvate or stereoisomer thereof, wherein (a) X is $CH_2$;
Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
wherein $R_6$ is H;
$R_7$ is $CH_3$, $C_2H_5$, n-$C_3H_7$, n-$C_4H_9$, or $C_6H_5$;
or
$R_6$ is $CH_3$;
$R_7$ is $C_2H_5$ or $CH_3$; and
$R_1$ is $CH_3$;

or (b) X is $CH_2$;
Y is $CH_2CONH$; and
$R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;

or (c) X is NHCO or NHCONH;
Y is $CH_2$; and
$R_1$ is $CH_3$;

or (d) X is NH;
Y is $CH_2CONH$; and
$R_1$ is $CH_3$;

or (e) X is NHCO or CO;
Y is $CH_2CONH$; and
$R_1$ is $CH_3$;

or (f) X is $CH_2$;
Y is $CH_2CO$;
wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and
$R_1$ is $CH_3$;

or (g) X is NHCONH, NHCO, or NH;
Y of structure (I) is not present and instead the phenyl group substituted with $R_2$ and $R_3$ is directly bonded to the N2 of the pyridazinone ring; and
$R_1$ is $CH_3$;

or (h) X is $CH_2$;
Y is $CH_2CONH$ or $CH(CH_3)CONH$;
the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and $R_1$ is $CH_3$;
or
(i) X and the phenyl group substituted with $R_4$ and $R_5$ are not present;
  Y is $CH_2CONH$; and
  $R_1$ is $CH_3$;
or
(j) X and the phenyl group substituted with $R_4$ and $R_5$ are not present;
  Y is $CH_2CONH$;
  $R_1$ is $CH_3$; and
    the bond between C4 and C5 of the pyridazinone ring is a single bond;
or
(k) X is $NH_2$ and the phenyl group substituted with $R_4$ and $R_5$ is not present;
  Y is $CH_2CONH$; and
  $R_1$ is $CH_3$;
or
(l) X of structure (I) is not present and instead the phenyl group substituted with $R_4$ and $R_5$ is directly bonded to C4 of the pyridazinone ring;
  Y is $CH_2CONH$; and
  $R_1$ is $CH_3$;
or
(m) X is NH;
  Y is $CH_2CONH$;
  $R_1$ is $CH_3$; and
  C5 is additionally substituted with $COCH_3$;
    wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group; and
wherein said compound is administered for a time and under conditions sufficient for said agent to induce cardiomyocyte FPR1 activation.

In accordance with the preceding aspects and embodiments, the compound of structure (I) may be:

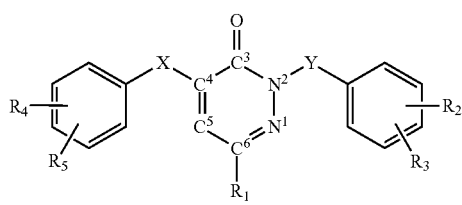

(I)

wherein
(a) X is $CH_2$;
  Y is $CH_2CONH$; and
  $R_1$ is $CH_3$;
or
(b) X and the phenyl group substituted with $R_4$ and $R_5$ are not present;
  Y is $CH_2CONH$; and
  $R_1$ is $CH_3$;
or
(c) X and the phenyl group substituted with $R_4$ and $R_5$ are not present;
  Y is $CH_2CONH$;
  $R_1$ is $CH_3$; and
    the bond between C4 and C5 of the pyridazinone ring is a single bond;
or
(d) X is $NH_2$ and the phenyl group substituted with $R_4$ and $R_5$ is not present;
  Y is $CH_2CONH$; and
  $R_1$ is $CH_3$;
or
(e) X of structure (I) is not present and instead the phenyl group substituted with $R_4$ and $R_5$ is directly bonded to C4 of the pyridazinone ring;
  Y is $CH_2CONH$; and
  $R_1$ is $CH_3$;
or
(f) X is $CH_2$;
  Y is $C(R_6R_7)CONH$;
    wherein $R_6$ is H;
    $R_7$ is $CH_3$, $C_2H_5$, $n-C_3H_7$, $i-C_3H_7$, $n-C_4H_9$, or $C_6H_5$;
    or
    $R_6$ is $CH_3$;
    $R_7$ is $C_2H_5$ or $CH_3$; and
  $R_1$ is $CH_3$;
or
(g) X is $CH_2$;
  Y is $CH(CH_3)CONH$
  $R_1$ is $CH_3$;
or
(h) X is $CH_2$;
  Y is $CH_2CONH$ or $CH(CH_3)CONH$;
    the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and
  $R_1$ is $CH_3$;
  wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group;
or
(i) X is $CH_2$;
  Y is $CH(CH_3)CONH$
  $R_1$ is $CH_3$;
  wherein $R_2$ is hydrogen and $R_3$ is para-bromine, and $R_4$ and $R_5$ are independently hydrogen, halogen, alkyl, alkoxy, haloalkyl, haloalkoxy, alkylsulfide, cyano, or nitro;
or
(j) X is $CH_2$;
  Y is $CH(CH_3)CONH$
  $R_1$ is $CH_3$;
  wherein $R_2$ and $R_3$ are independently hydrogen, halogen, alkyl, alkoxy, haloalkyl, haloalkoxy, alkylsulfide, cyano, or nitro, and $R_4$ is hydrogen and $R_5$ is meta-methoxy;
or
(k) X is $CH_2$;
  Y is $CH(CH_3)CONH$
  $R_1$ is $CH_3$;
  wherein $R_2$ is hydrogen and $R_3$ is para-bromine, and $R_4$ is hydrogen and $R_5$ is meta-methoxy;
or a pharmaceutically acceptable salt, solvate or stereoisomer thereof.

Compounds of structure (I) include, but are not limited to:

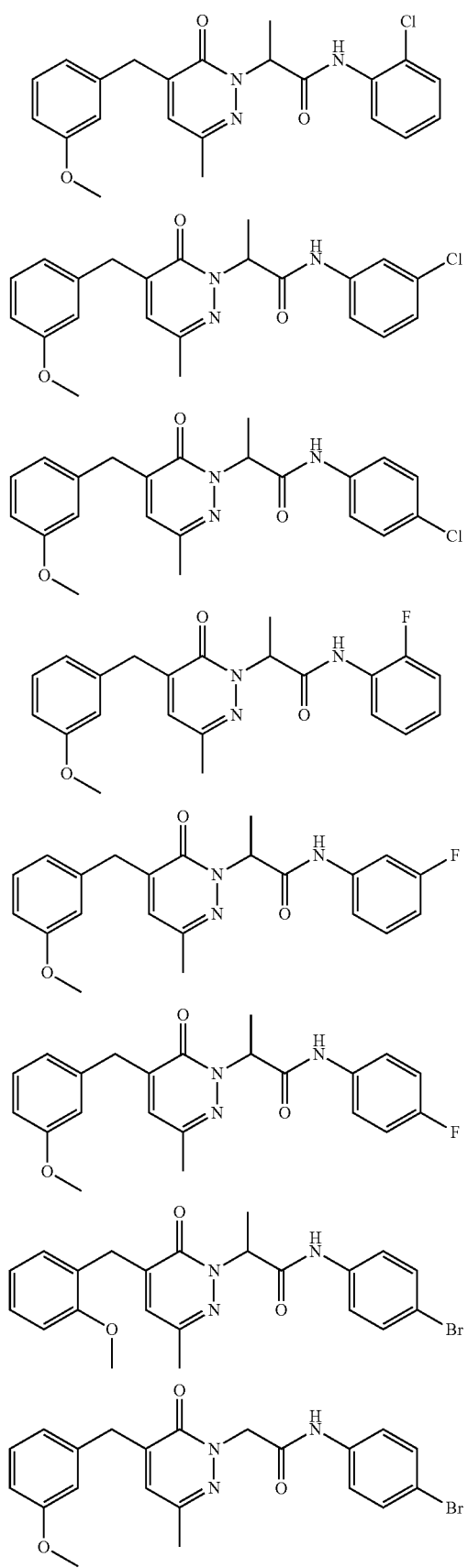
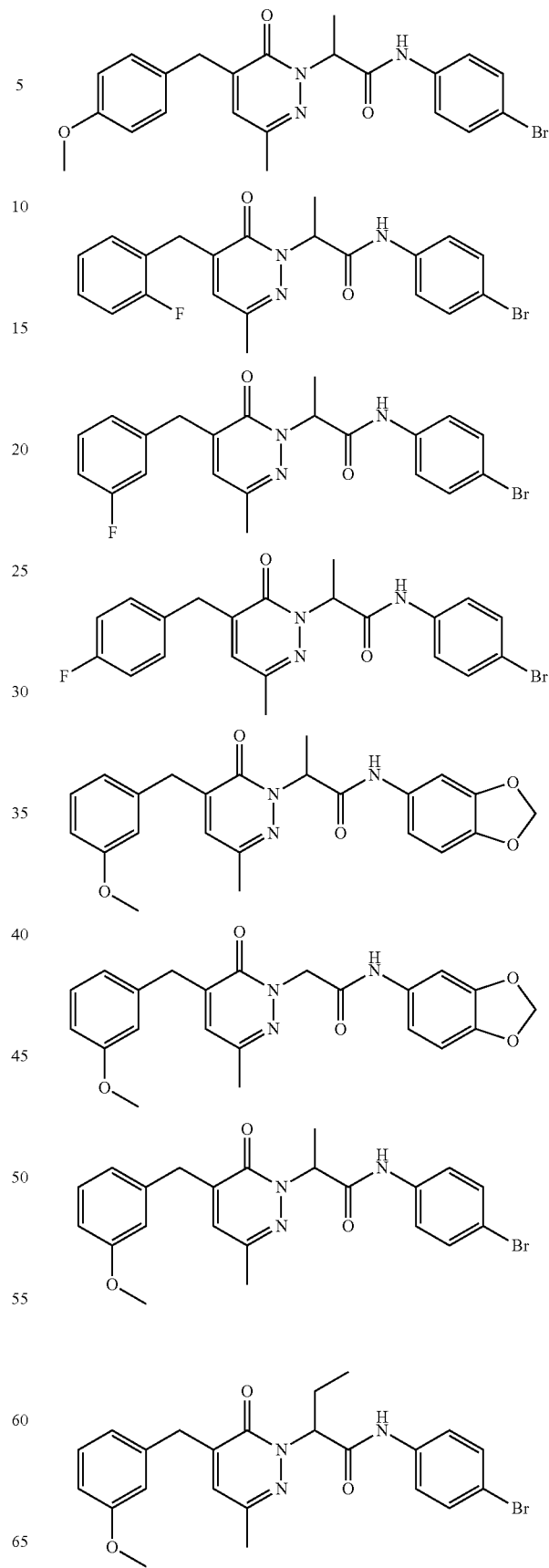

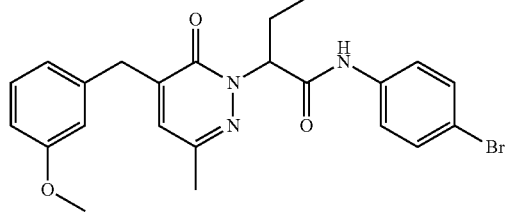
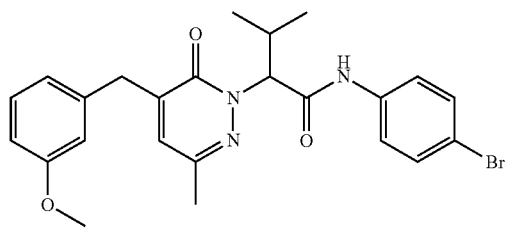
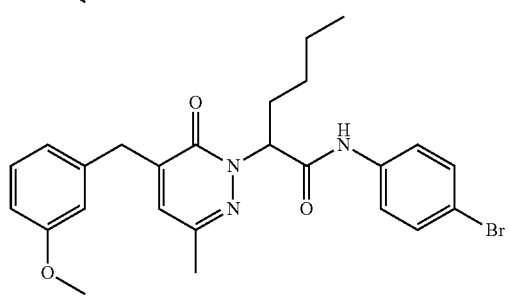
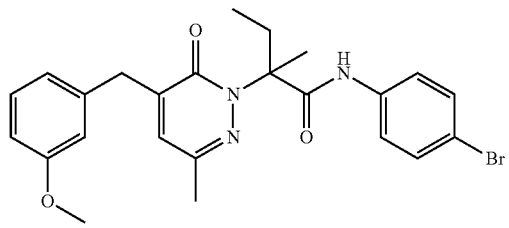
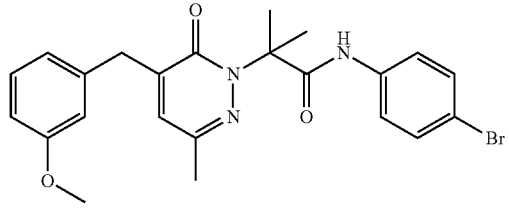
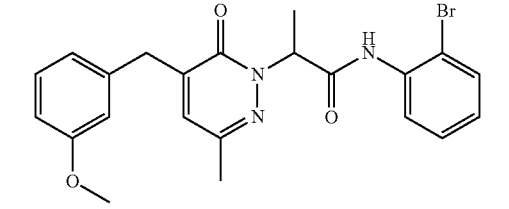
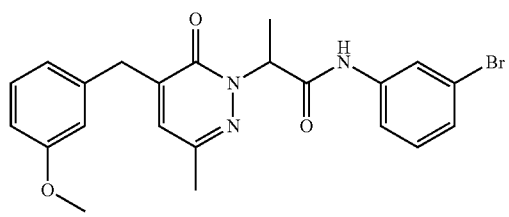
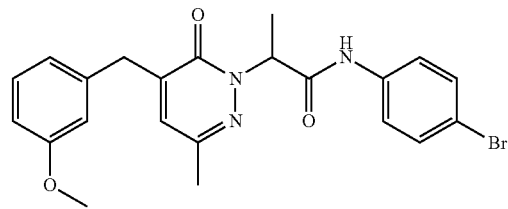
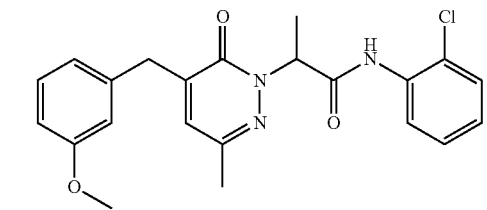
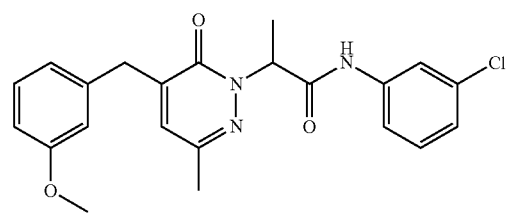
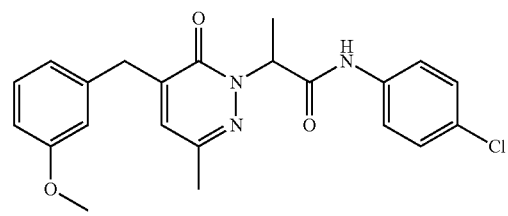
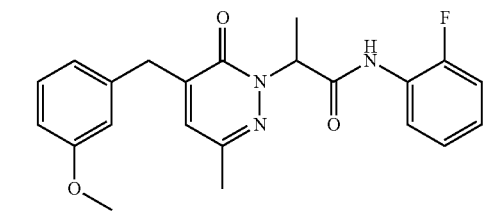
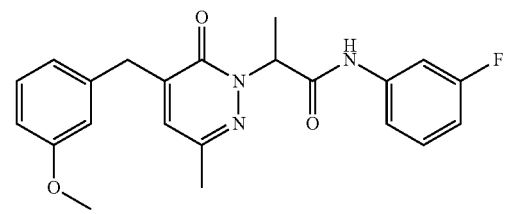
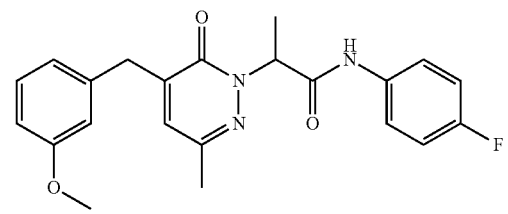
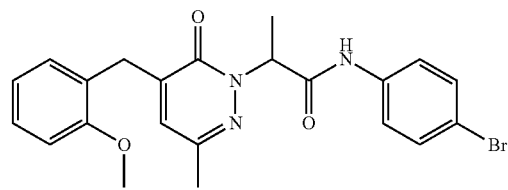

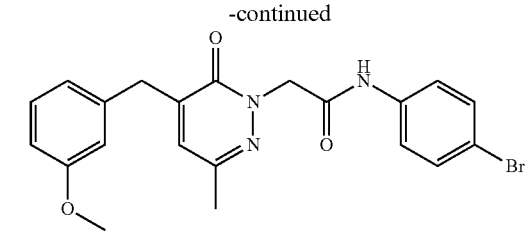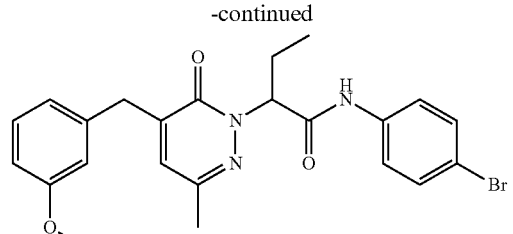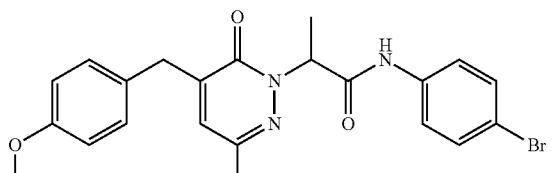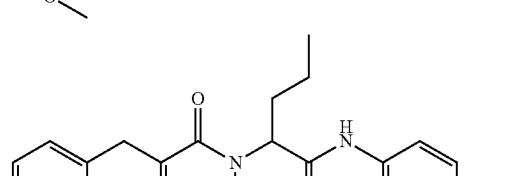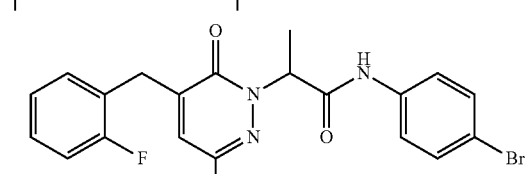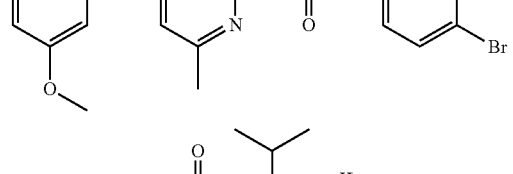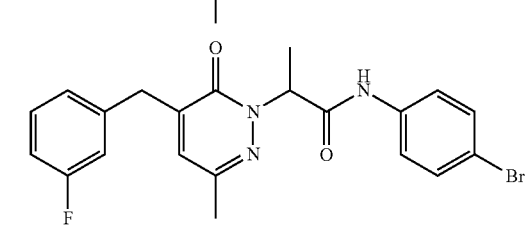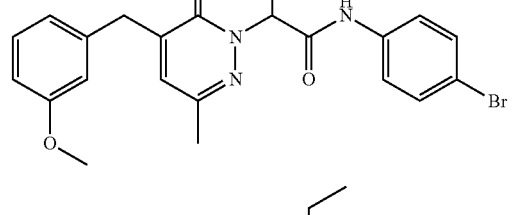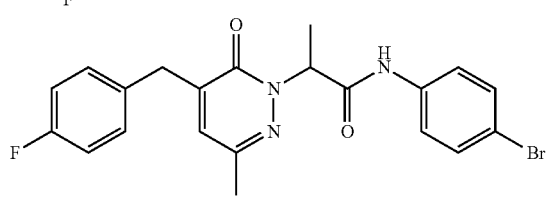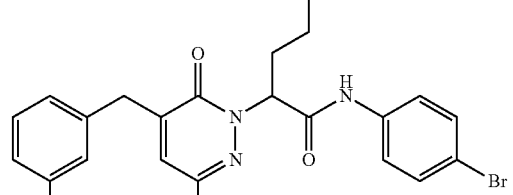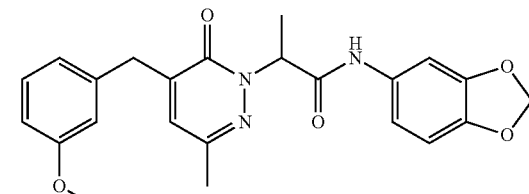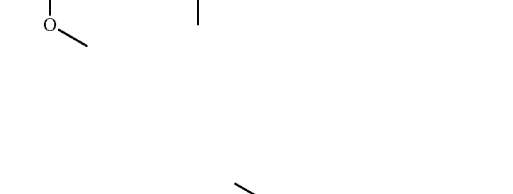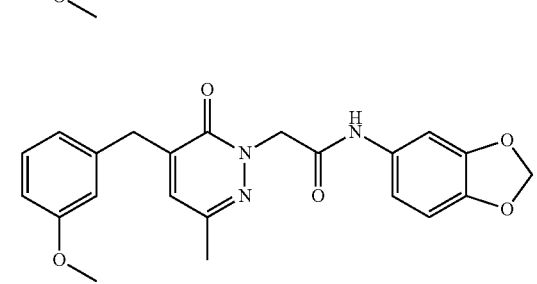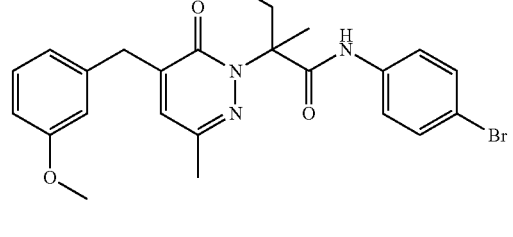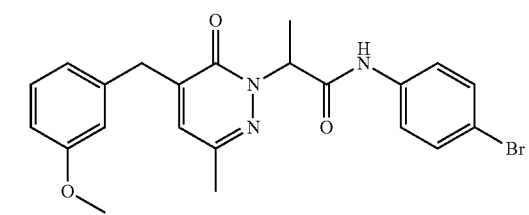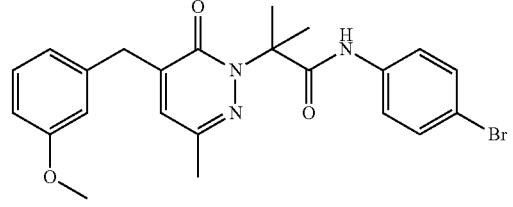

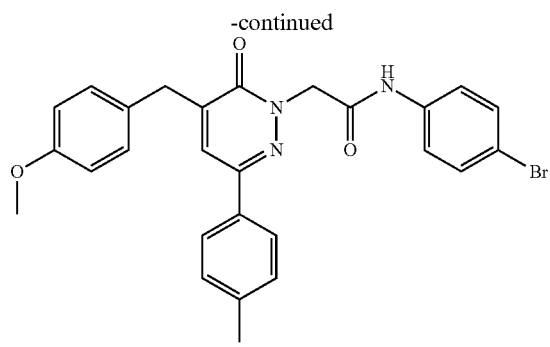
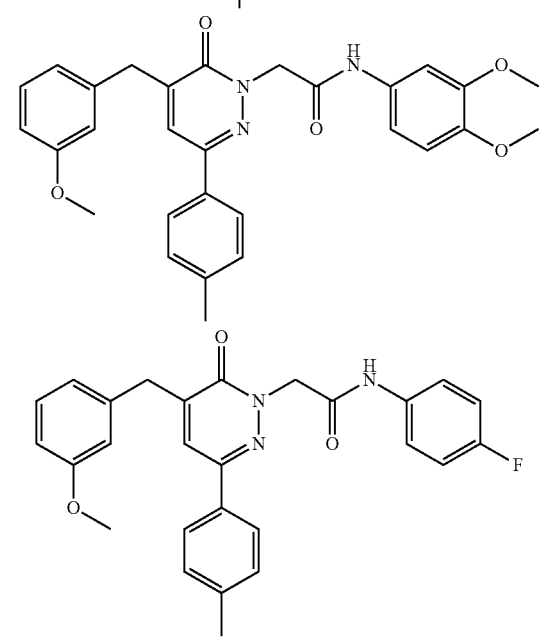
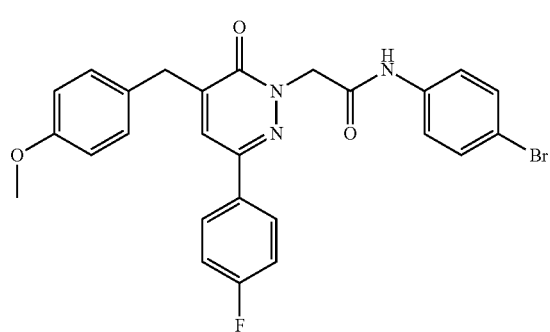
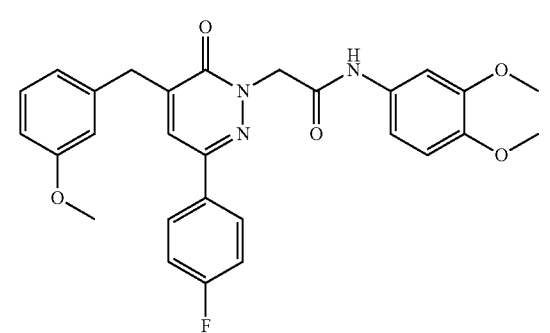
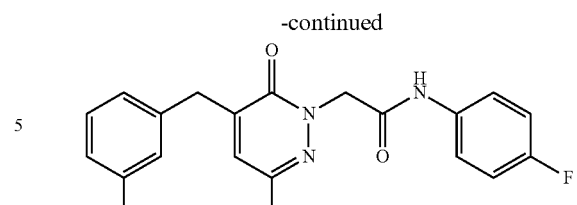
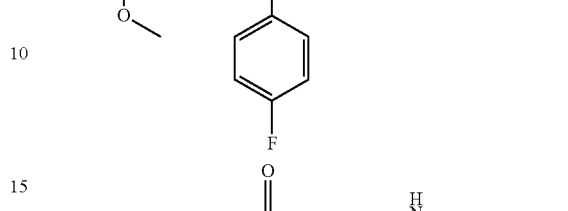
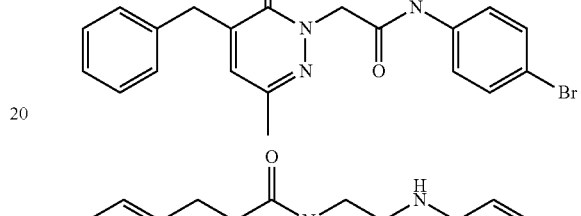
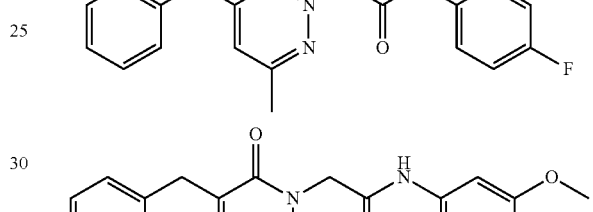
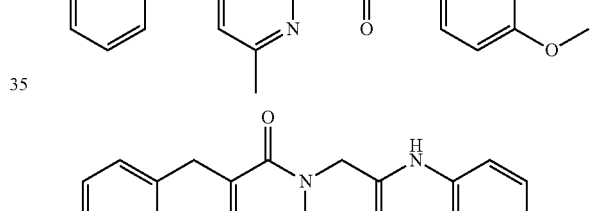

-continued
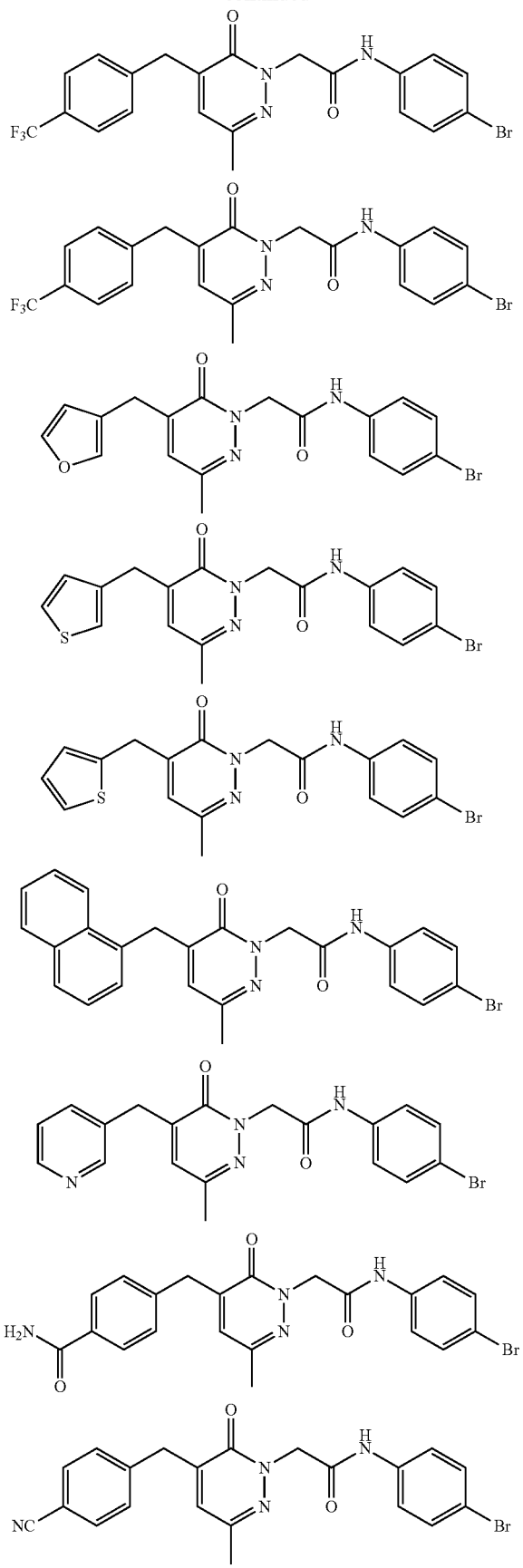
-continued
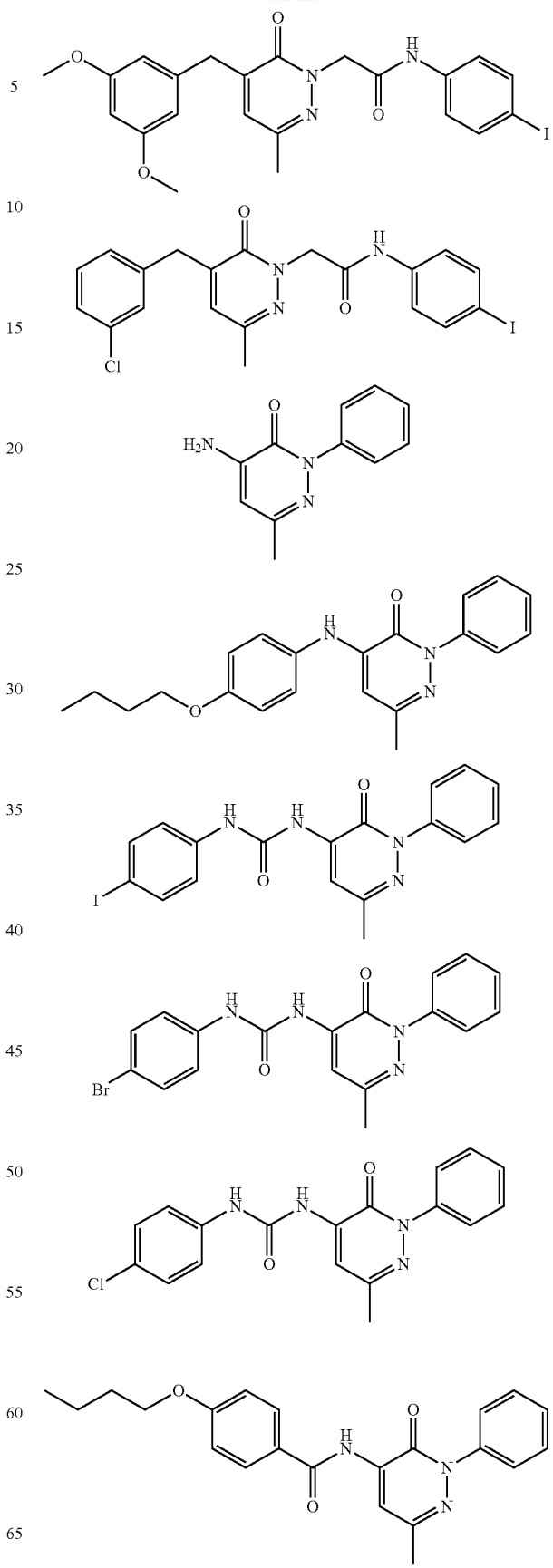

-continued
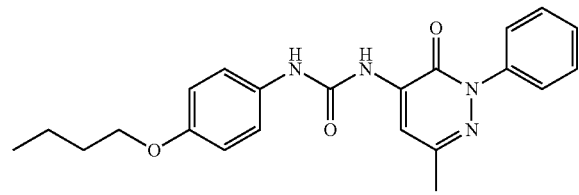
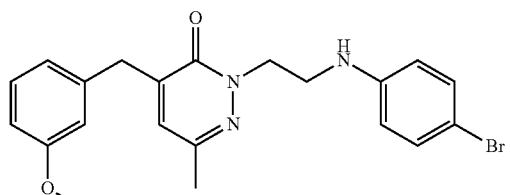
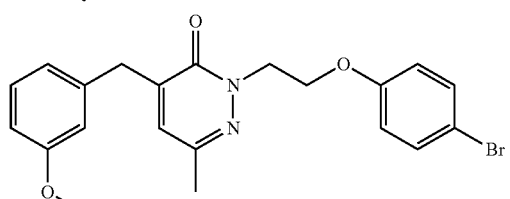
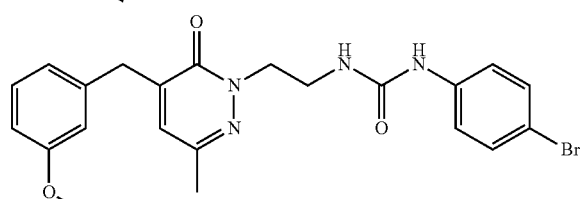
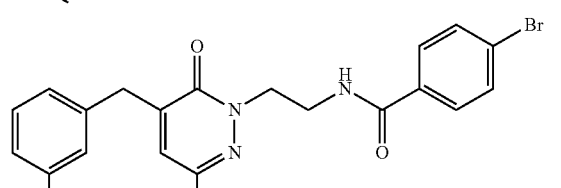
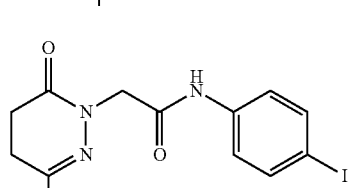
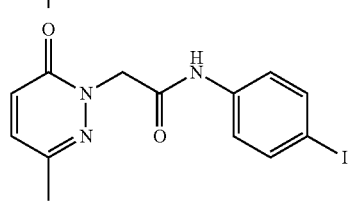
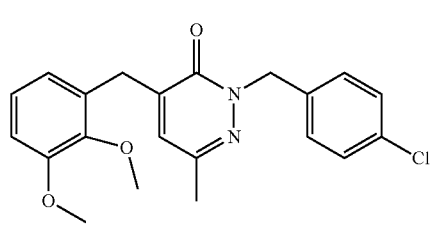
-continued
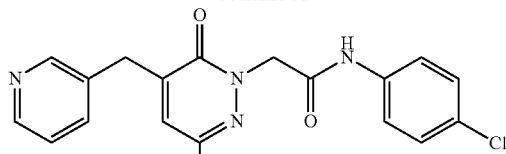
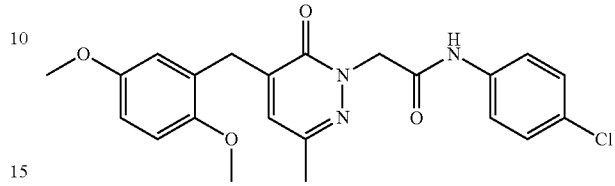
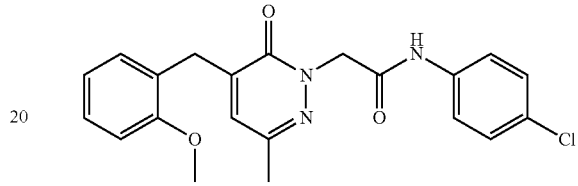
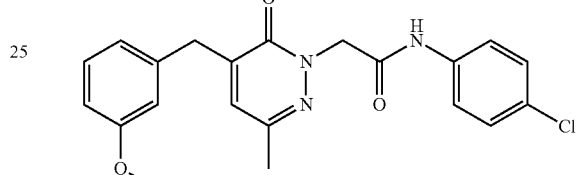
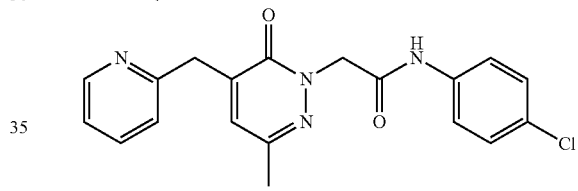
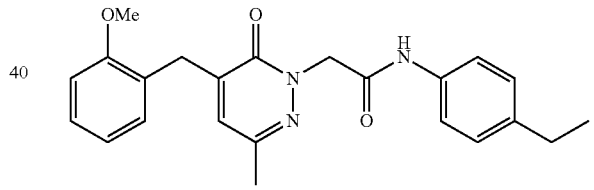
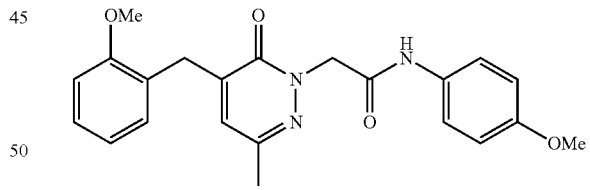
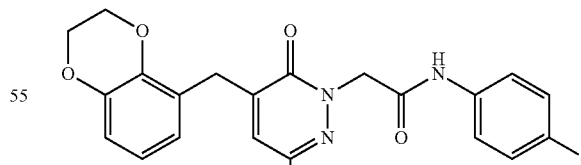
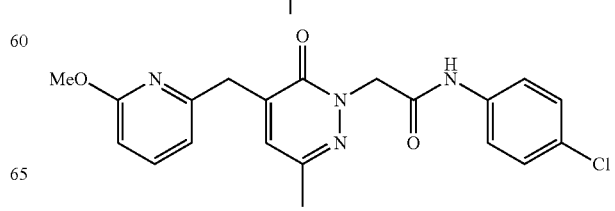

-continued

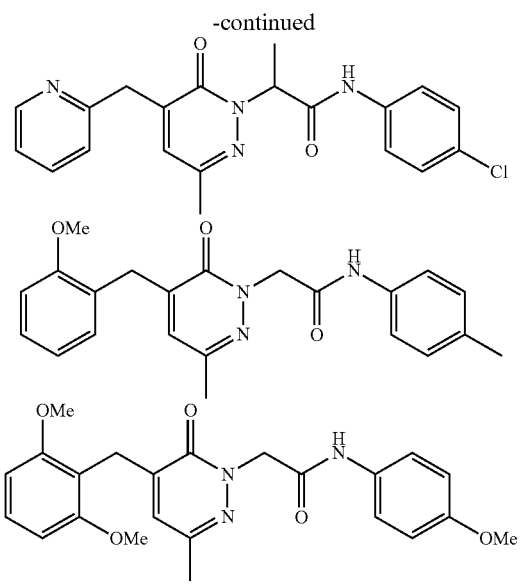

and pharmaceutically acceptable salts, solvates or stereoisomers thereof.

Yet another aspect of the present invention is directed to the use of the compounds as hereinbefore defined in the manufacture of a medicament for minimising the extent of ischaemia-induced myocardial tissue damage in a mammal.

In still yet another aspect, there is provided the use of the compounds as hereinbefore defined in the manufacture of a medicament for minimising the extent of ischaemia-reperfusion-induced myocardial tissue damage in a mammal.

A further aspect of the present invention is directed to a method of identifying a candidate compound that modulates the activity of a target receptor comprising:
a) contacting receptor with a candidate compound,
b) determining the binding of the candidate compound to the receptor;
c) selecting for candidate compounds which activate the receptor;

wherein the target receptor is formyl peptide receptor subtype FPR1; and the candidate compound activates the FPR1 subtype to a greater degree than the activation by an endogenous ligand or substrate for the FPR1 subtype.

Preferably, said compound selectively activates ERK/Akt signalling.

BRIEF DESCRIPTION OF THE DRAWINGS

FIG. 2 is a graphical representation of the effect of agonist stimulation (fMLP, BIDI-001 and BIDI-002) on FPR mediated $[Ca^{2+}]_i$ mobilization in Flpln-CHO cells stably expressing the human FPR1 (A) or FPR2 (B) receptors. Data points represent a percentage of the mean±SEM of $[Ca^{2+}]_i$ mobilization elicited by ATP from 3-7 experiments performed in triplicate.

FIG. 3 is a graphical representation of the effect of agonist stimulation (fMLP, BIDI-001 and BIDI-002) on FPR-mediated pERK1/2 in Flpln-CHO cells stably expressing the human FPR1 (A) or FPR2 (B) receptors. Data points represent a percentage of the mean±SEM of ERK1/2 phosphorylation elicited by 10% FBS±SEM collected from 4-6 experiments performed in triplicate.

FIG. 5 is a graphical representation of the effect of agonist stimulation (fMLP, BIDI-001 and BIDI-002) on FPR-mediated inhibition of forkskolin-stimulated cAMP accumulation in Flpln-CHO cells stably expressing the human FPR1 (A) or FPR2 (B) receptors. Data points represent a percentage of the mean±SEM of forkskolin response collected from 3-4 experiments performed in triplicate.

FIG. 6 is a schematic representation of the effect of agonist stimulation (fMLP, BIDI-001 and BIDI-002) on FPR-mediated biased signalling in $[Ca^{2+}]_i$ mobilization, pERK1/2, pAkt1/2/3, and inhibition of cAMP accumulation in Flpln-CHO cells stably expressing the human FPR1 (A) or FPR2 (B) receptors.

FIG. 7 is an image depicting the effect of peptide and small molecule ANX-A1 mimetics on cardiac necrosis after 24 h I-R injury. A) LV transverse slices from representative mice subjected to 40 min ischaemia followed by 24 h reperfusion in different treatment groups: vehicle, $AC_{2-26}$, or small molecule mimetics (BIDI-001, BIDI-002). Three different zones are visible after staining with Evans blue and then TTC. The area stained dark blue, white and red represented non-risk zones, infarct zones and ischaemic but non-infarcted zones, respectively. The risk zone includes red and white areas. B) Pooled data of area-at-risk in mice subjected to myocardial I-R in the different treatment groups. C) Pooled data of infarct size in different treatment groups. D) Pooled data of plasma levels of cardiac troponin (cTnI) in different treatment groups subjected to I-R. Numbers indicate n/group. #$P<0.05$ versus sham, *$P<0.05$ versus vehicle treated mice. One-way ANOVA with Tukey post-hoc test. Data were represented as mean±SEM.

2/3Ser473), whilst sparing pathways that may contribute undesirable consequences (e.g. Ca2+i).

FIG. 21 is an image and graphical representation of (A) Chemical structures of small molecule FPR agonists N-(4-bromophenyl)-2-[5-(3-methoxybenzyl)-3-methyl-6-oxo-6H-pyridazin-1-yl]-propionamide, identified as compound 17b (Cmpd17b or BIDI-001) and the Amgen pyrazolone derivative, identified as compound 43 (Cmpd43 or BIDI-002). B) To quantify signaling bias, agonist concentration—response curves were analyzed by nonlinear regression using an operational model of agonism to define the τ/KA "transduction ratio" for each agonist for each pathway, where Em is the maximal possible response of the system (not the agonist), KA denotes the functional equilibrium dissociation constant of the agonist for the receptor, and τ the efficiency of coupling of the receptor its subsequent cellular stimulus-response transduction mechanism.

Figure 22:
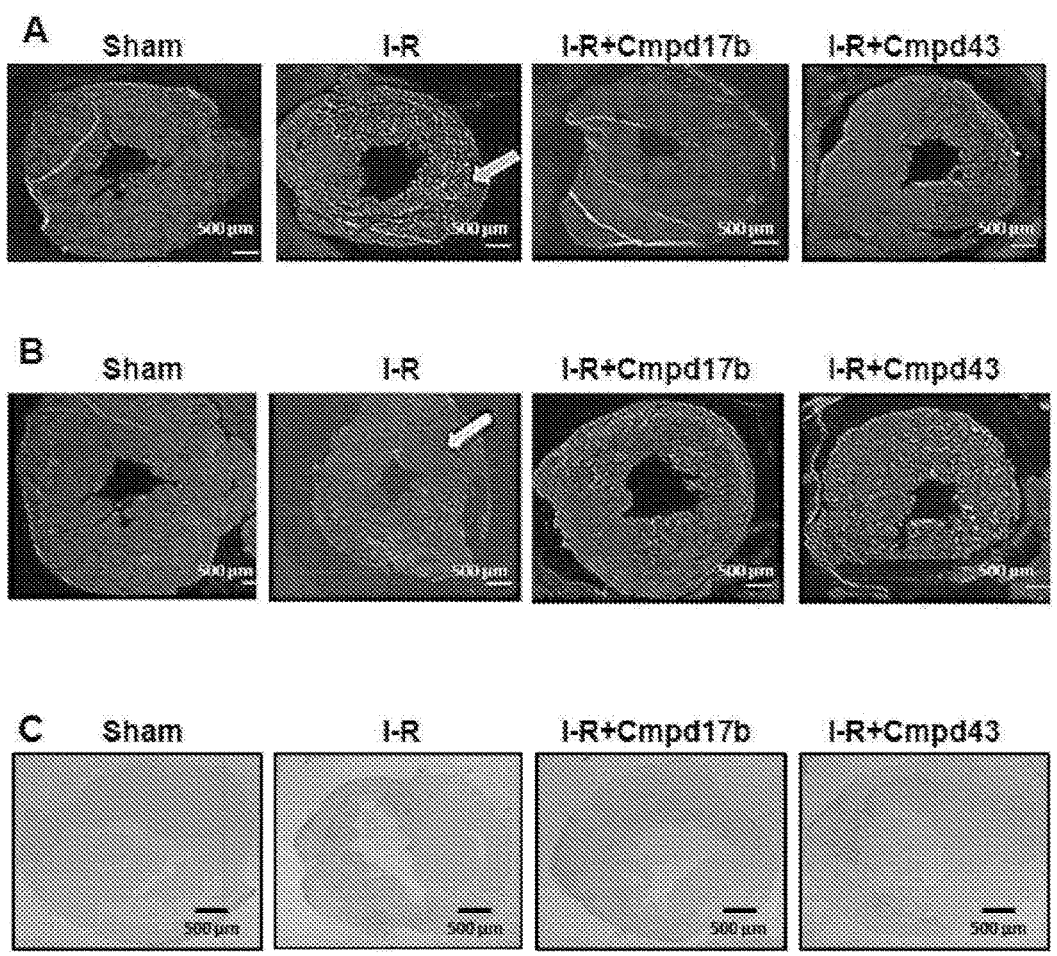

FIG. 22 is an image of FPR-agonist Cmpd17b reduces cardiac inflammation and fibrosis post I-R injury in vivo. A) Representative immunofluorescent images of LV neutrophil content (using an anti-Ly-6B.2 antibody) and B) Representative immunofluorescent images of LV macrophage content (using an anti-CD68 antibody) from sham, vehicle-, and FPR-agonist-treated (Cmpd17b or Cmpd43, 50 mg/kg, i.p.) mice, 48 h post I-R. Scale bars: 500 μm (stitched 9×9 single images under 20× magnification). C) Representative picrosirius red-stained LV cross-sections from sham, vehicle- and FPR-agonist (Cmpd17b or Cmpd43, 50 mg/kg i.p.)-treated mice, 7-days post I-R. Scale bars: 500 μm (magnification ×12.5).

Figure 23:
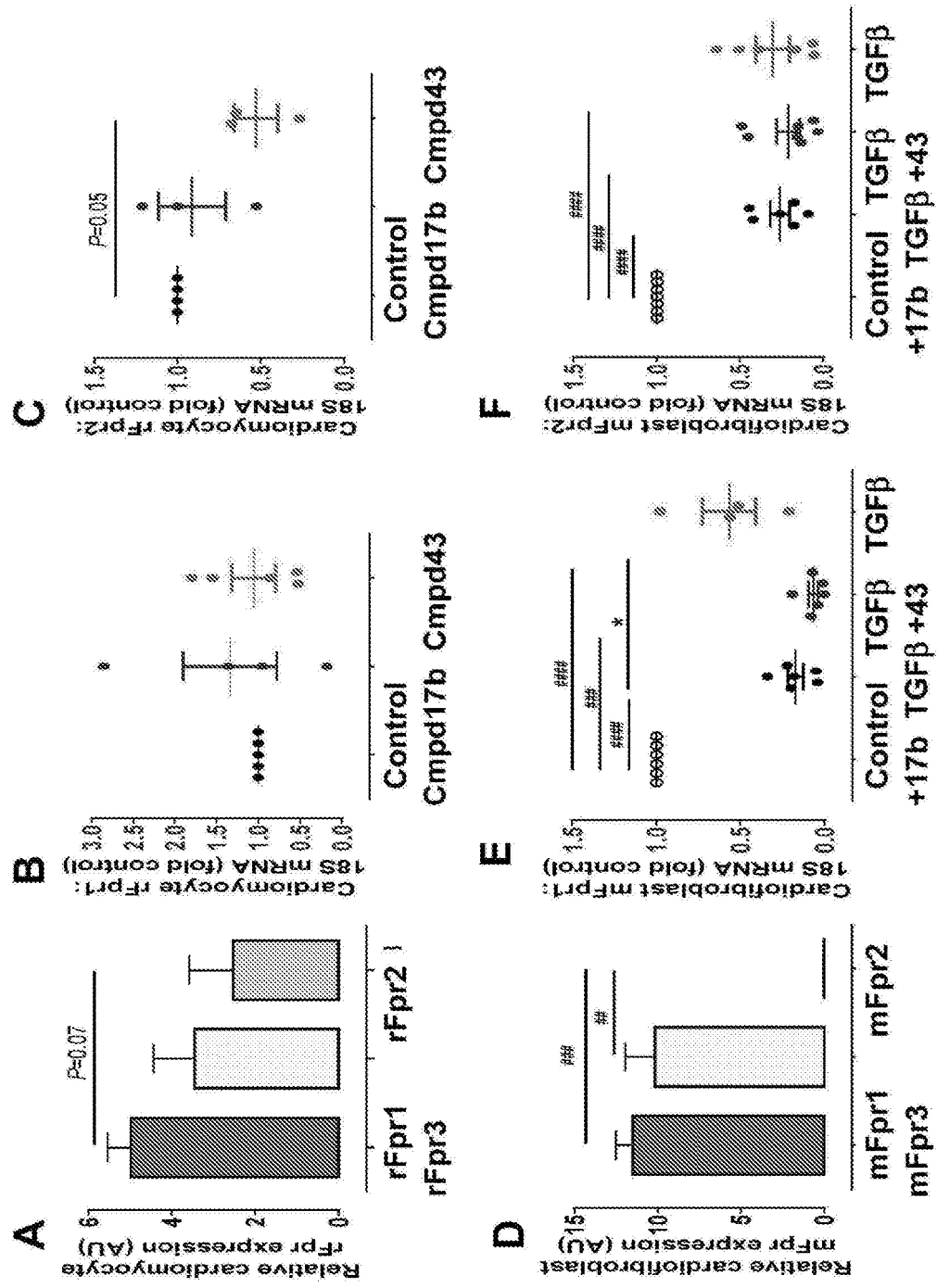

FIG. 23 is a graphical representation of cardiomyocyte expression of Fprs in vitro. A) Relative expression of rat Fprs (rFpr1, rFpr2 and rFpr3) in untreated NRCM determined via real-time PCR (expressed as the threshold cycle number Ct subtracted from the maximum cycle number utilized, 40). Impact of 48 h incubation with Cmpd17b and Cmpd43 (both 1 μM) on NRCM expression of B) rFpr1 and C) rFpr2, expressed as fold change vs vehicle-treated cells. D Relative expression of mouse Fprs (mFpr1 and mFpr2) in AMCF determined via real-time PCR. Impact of 24 h incubation with Cmpd17b and Cmpd43 (both 10 μM) on AMCF expression of E mFpr1 and F mFpr2, fold vehicle-treated cells. #P<0.05, ##P<0.01, ###P<0.001 and ####P<0.0001 vs vehicle, *P<0.05 vs TGF-β, One-way ANOVA with Tukey's post-hoc test. Data represented as mean±SEM.

Figure 24:
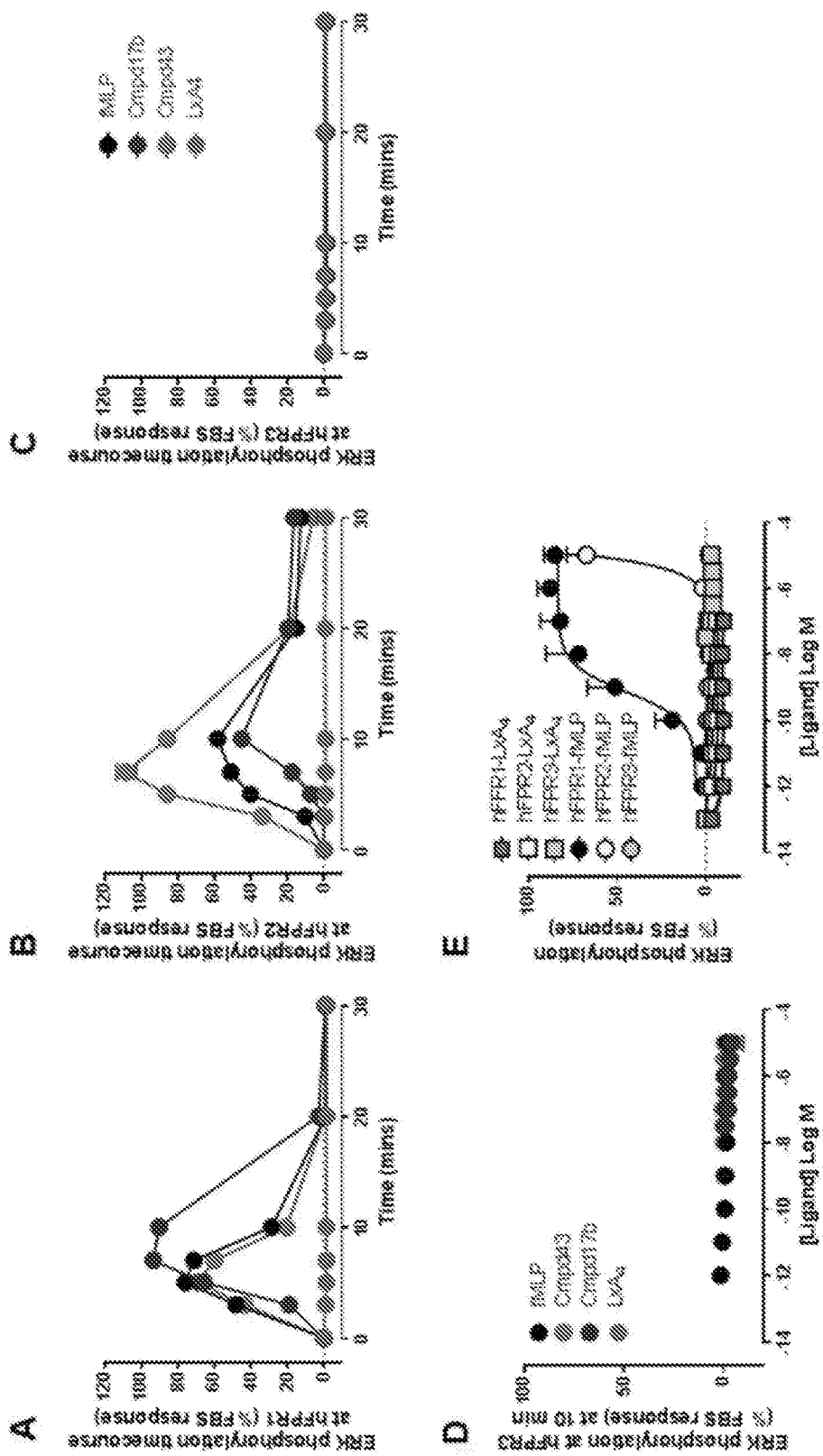

FIG. 24 is a graphical representation of ERK1/2 phosphorylation in hFPR subtypes and description of the quantitative framework of GPCR agonism. Pilot timecourse study of ERK1/2 phosphorylation in response to fMLP, Cmpd17b, Cmpd43 and LxA4 (each 10 μM, n=1) in hFPR-transfected CHO cells: A) hFPR1; B) hFPR2; C) FPR3. D) Concentration-response curves for each FPR agonist in hFPR3-CHO cells (results expressed as mean±SEM of 3-4 experiments each performed in triplicate). E) Concentration-response curves to LxA4 (with fMLP shown for comparison) on ERK1/2 phosphorylation in hFPR subtypes.

FIG. 25 is an image and graphical representation of BIDI-001 biased signalling away from Ca2+i at FPR1 in CHO cells in vitro.

DETAILED DESCRIPTION OF THE INVENTION

The present invention is predicated, in part, on the unexpected identification of compounds that can both selectively activate FPR1 expressed on cardiomyocytes and, still further, selectively activate FPR1-ERK/Akt-mediated signalling, which acts to maintain cardiomyocyte viability and upregulate contractile functioning. This finding is particularly significant, however, since it provides a means of upregulating cardiomyocyte viability and contractile functionality without the concomitant adverse outcome of inducing intracellular $Ca^{2+}$ mobilisation. Accordingly, despite the fact that the prior art methods have largely focussed on the cardioprotective capabilities of annexin-mediated FPR2 activation, the selective activation of FPR1 has now been determined to also achieve both maintenance of cardiomyocyte viability and restoration of contractile function, albeit without the side effect of intracellular $Ca^{2+}$ mobilisation which, in the context of cardiac ischaemia-reperfusion injury, is extremely undesirable and can lead to tissue death. The present inventors have, for the first time, identified molecules which can achieve this highly selective functional outcome.

Accordingly, one aspect of the present invention is directed to a method of minimising the extent of ischaemia-induced myocardial tissue damage in a mammal, said method comprising administering to said mammal an effective amount of a compound of structure (I):

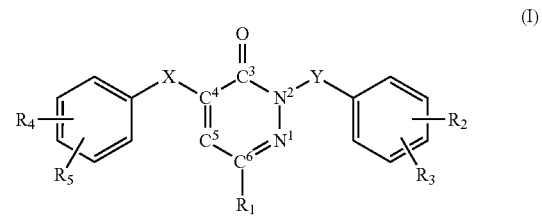

or a pharmaceutically acceptable salt, solvate or stereoisomer thereof, wherein (a) X is $CH_2$;
  Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
    wherein $R_6$ is H;
    $R_7$ is $CH_3$, $C_2H_5$, n-$C_3H_7$, i-$C_3H_7$, n-$C_4H_9$, or $C_6H_5$;
    or
    $R_6$ is $CH_3$;
    $R_7$ is $C_2H_5$ or $CH_3$; and
  $R_1$ is $CH_3$;
or
(b) X is $CH_2$;
  Y is $CH_2CONH$; and
  $R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or
(c) X is NHCO or NHCONH;
  Y is $CH_2$; and
  $R_1$ is $CH_3$;
or
(d) X is NH;
  Y is $CH_2CONH$; and
  $R_1$ is $CH_3$;
or
(e) X is NHCO or CO;
  Y is $CH_2CONH$; and
  $R_1$ is $CH_3$;
or (f) X is CH$_2$;
   Y is CH$_2$CO;
      wherein the phenyl group substituted with R$_2$ and R$_3$ and bonded to Y of structure (I) is replaced with N-methyl piperazine, N(CH$_3$)—C$_6$H$_4$—Br, NHCH$_2$—C$_6$H$_4$—Br, or O—C$_6$H$_4$—Br; and
   R$_1$ is CH$_3$;
or
(g) X is NHCONH, NHCO, or NH;
   Y of structure (I) is not present and instead the phenyl group substituted with R$_2$ and R$_3$ is directly bonded to the N2 of the pyridazinone ring; and
   R$_1$ is CH$_3$;
or
(h) X is CH$_2$;
   Y is CH$_2$CONH or CH(CH$_3$)CONH;
      the phenyl group substituted with R$_4$ and R$_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and
   R$_1$ is CH$_3$;
or
(i) X and the phenyl group substituted with R$_4$ and R$_5$ are not present;
   Y is CH$_2$CONH; and
   R$_1$ is CH$_3$;
or
(j) X and the phenyl group substituted with R$_4$ and R$_5$ are not present;
   Y is CH$_2$CONH;
   R$_1$ is CH$_3$; and the bond between C4 and C5 of the pyridazinone ring is a single bond;
or
(k) X is NH$_2$ and the phenyl group substituted with R$_4$ and R$_5$ is not present;
   Y is CH$_2$CONH; and
   R$_1$ is CH$_3$;
or
(l) X of structure (I) is not present and instead the phenyl group substituted with R$_4$ and R$_5$ is directly bonded to C4 of the pyridazinone ring;
   Y is CH$_2$CONH; and
   R$_1$ is CH$_3$;
or
(m) X is NH;
   Y is CH$_2$CONH;
   R$_1$ is CH$_3$; and
      C5 is additionally substituted with COCH$_3$;
   wherein R$_2$, R$_3$, R$_4$ and R$_5$ are independently hydrogen, halogen, alkyl, alkoxy, haloalkyl, haloalkoxy, alkylsulfide, cyano, nitro, or R$_2$ and R$_3$ and/or R$_4$ and R$_5$ is a bridged di-alkoxy group; and
wherein said compound is administered for a time and under conditions sufficient for said agent to induce cardiomyocyte FPR1 activation.

Reference to "myocardial tissue" should be understood as a reference to the tissue of the heart. This tissue is comprised of a heterogeneous population of cells and reference to "myocardial tissue" therefore includes reference to all of these cells. This includes, for example, the myocardium, being the striated, involuntary muscle of the heart, as well as the other cell types present in the heart such as blood vessels, nerves, connective tissue and the like.

Reference to myocardial tissue "damage" should be understood as a reference to any form of structural, functional or metabolic damage which occurs to one or more subpopulations of cells that form part of the heart. Without limiting the present invention to any one theory or mode of action, myocardial ischaemia is characterised by a restriction in blood supply to the myocardial tissue. Due to the resultant reduction in delivery of oxygen (hypoxia) and other metabolites, myocyte necrosis occurs, this also being known as a myocardial infarction. This event then initiates a complex response, sometimes termed an ischaemia cascade, which occurs in 3 basic phases, as follows:
(i) an initiation phase;
(ii) an acute inflammatory phase; and
(iii) a repair phase.

More specifically, within minutes of ischaemia, the innate immune system is initiated by complement activation, expression of the TLR4 and the generation of reactive oxygen species (ROS). The acute inflammatory phase begins within hours of ischaemia and is characterised by a cellular infiltrate of neutrophils and M1-like macrophages, together with a large number of 'pro-inflammatory' chemokines and cytokines. Neutrophils, which accumulate rapidly within the first 24 hours, are a rich source of matrix metalloproteinases (MMP) that assist clearance of dead cells and debris. M1-like macrophages are a major cell type present during the acute inflammatory phase. Migration to the site of ischaemia is mediated by binding of CCR2 to high levels of MCP-1 (CCL2). Granulocyte-macrophage colony stimulating factor (GM-CSF) promotes production of inflammatory cytokines (TNF-α, IL-6 and IL-1β) by M1-like cells (Fleetwood 2007, supra). After 2-3 days, there is a gradual switch from M1-like to M2-like macrophages associated with a change in cytokine profile from pro-inflammatory to anti-inflammatory such that new vessel formation (angiogenesis) and fibrosis occurs. Macrophage colony stimulating factor (M-CSF) promotes differentiation of monocytes to M2-like cells, leading to secretion of anti-inflammatory cytokines such as IL-10 (Fleetwood 2007, supra). The cardiac fibrosis and remodelling, however, although occurring as a compensatory mechanism to maintain cardiac output is nevertheless ultimately deleterious to left ventricular functioning. The tissue damage of the present invention therefore, includes but is not limited to, myocardial inflammation, loss of contractile functioning, cellular necrosis, cellular apoptosis, fibrosis, collagen, scar formation, tissue remodelling, infarct formation (this latter phrase commonly being used to describe the mass of myocardial tissue which is damaged) and left ventricular functioning.

In one embodiment, said myocardial tissue damage is the loss of cellular viability and contractile functioning.

According to this embodiment there is provided a method of minimising the extent of ischaemia-induced myocardial tissue damage in a mammal, said method comprising administering to said mammal an effective amount of a compound of structure (I):

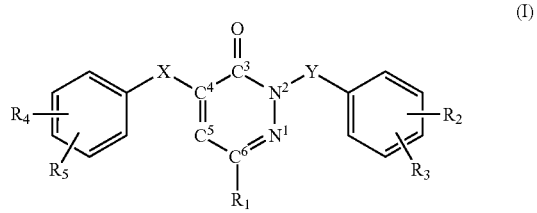

or a pharmaceutically acceptable salt, solvate or stereoisomer thereof, wherein
(a) X is $CH_2$;
  Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
    wherein $R_6$ is H;
      $R_7$ is $CH_3$, $C_2H_5$, $n-C_3H_7$, $i-C_3H_7$, $n-C_4H_9$, or $C_6H_5$;
    or
      $R_6$ is $CH_3$;
      $R_7$ is $C_2H_5$ or $CH_3$; and
    $R_1$ is $CH_3$;
or
(b) X is $CH_2$;
  Y is $CH_2CONH$; and
  $R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or
(c) X is NHCO or NHCONH;
  Y is $CH_2$; and
  $R_1$ is $CH_3$;
or
(d) X is NH;
  Y is $CH_2CONH$; and
  $R_1$ is $CH_3$;
or
(e) X is NHCO or CO;
  Y is $CH_2CONH$; and
  $R_1$ is $CH_3$;
or
(f) X is $CH_2$;
  Y is $CH_2CO$;
    wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and
  $R_1$ is $CH_3$;
or
(g) X is NHCONH, NHCO, or NH;
  Y of structure (I) is not present and instead the phenyl group substituted with $R_2$ and $R_3$ is directly bonded to the N2 of the pyridazinone ring; and
  $R_1$ is $CH_3$;
or
(h) X is $CH_2$;
  Y is $CH_2CONH$ or $CH(CH_3)CONH$;
    the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and
  $R_1$ is $CH_3$;
or
(i) X and the phenyl group substituted with $R_4$ and $R_5$ are not present;
  Y is $CH_2CONH$; and
  $R_1$ is $CH_3$;
or
(j) X and the phenyl group substituted with $R_4$ and $R_5$ are not present;
  Y is $CH_2CONH$;
  $R_1$ is $CH_3$; and
  the bond between C4 and C5 of the pyridazinone ring is a single bond;
or
(k) X is $NH_2$ and the phenyl group substituted with $R_4$ and $R_5$ is not present;
  Y is $CH_2CONH$; and
  $R_1$ is $CH_3$;
or
(l) X of structure (I) is not present and instead the phenyl group substituted with $R_4$ and $R_5$ is directly bonded to C4 of the pyridazinone ring;
  Y is $CH_2CONH$; and
  $R_1$ is $CH_3$;
or
(m) X is NH;
  Y is $CH_2CONH$;
  $R_1$ is $CH_3$; and
  C5 is additionally substituted with $COCH_3$;
    wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group; and
wherein said compound is administered for a time and under conditions sufficient for said agent to induce cardiomyocyte FPR1 activation, and wherein said tissue damage is loss of cellular viability and contractile function.

Reference to "minimising the extent of" said tissue damage should be understood as a reference to inhibiting, retarding or otherwise reducing the severity or extent of any one or more aspects of said tissue damage relative to the severity or extent of tissue damage which would occur in an untreated mammal. Accordingly, said "minimisation" may be partial (in that some level of damage does occur but is not as extensive as would otherwise have occurred) or complete (in that the damage is completely prevented) and may refer to all or only some of the forms of tissue damage which are contemplated herein.

In one embodiment said ischaemia-induced myocardial tissue damage is myocardial infarction induced tissue damage and, more particularly, acute myocardial infarction induced tissue damage.

Accordingly, the present invention provides a method of minimising the extent of myocardial infarction related tissue damage in a mammal, said method comprising administering to said mammal an effective amount of a compound of structure (I):

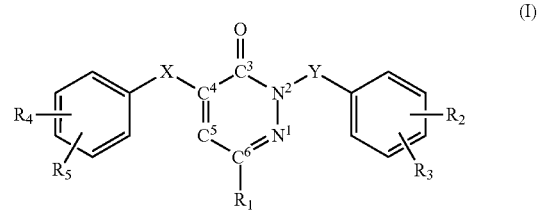

or a pharmaceutically acceptable salt, solvate or stereoisomer thereof, wherein
(a) X is $CH_2$;
  Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
    wherein $R_6$ is H;
      $R_7$ is $CH_3$, $C_2H_5$, $n-C_3H_7$, $i-C_3H_7$, $n-C_4H_9$, or $C_6H_5$;

or
$R_6$ is $CH_3$;
$R_7$ is $C_2H_5$ or $CH_3$; and
$R_1$ is $CH_3$;
or
(b) X is $CH_2$;
Y is $CH_2CONH$; and
$R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or
(c) X is NHCO or NHCONH;
Y is $CH_2$; and
$R_1$ is $CH_3$;
or
(d) X is NH;
Y is $CH_2CONH$; and
$R_1$ is $CH_3$;
or
(e) X is NHCO or CO;
Y is $CH_2CONH$; and
$R_1$ is $CH_3$;
or
(f) X is $CH_2$;
Y is $CH_2CO$;
wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and
$R_1$ is $CH_3$;
or
(g) X is NHCONH, NHCO, or NH;
Y of structure (I) is not present and instead the phenyl group substituted with $R_2$ and $R_3$ is directly bonded to the N2 of the pyridazinone ring; and
$R_1$ is $CH_3$;
or
(h) X is $CH_2$;
Y is $CH_2CONH$ or $CH(CH_3)CONH$;
the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and
$R_1$ is $CH_3$;
or
(i) X and the phenyl group substituted with $R_4$ and $R_5$ are not present;
Y is $CH_2CONH$; and
$R_1$ is $CH_3$;
or
(j) X and the phenyl group substituted with $R_4$ and $R_5$ are not present;
Y is $CH_2CONH$;
$R_1$ is $CH_3$; and
the bond between C4 and C5 of the pyridazinone ring is a single bond;
or
(k) X is $NH_2$ and the phenyl group substituted with $R_4$ and $R_5$ is not present;
Y is $CH_2CONH$; and
$R_1$ is $CH_3$;
or (l) X of structure (I) is not present and instead the phenyl group substituted with $R_4$ and $R_5$ is directly bonded to C4 of the pyridazinone ring;
Y is $CH_2CONH$; and
$R_1$ is $CH_3$;
or
(m) X is NH;
Y is $CH_2CONH$;
$R_1$ is $CH_3$; and
C5 is additionally substituted with $COCH_3$;
wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group; and
wherein said compound is administered for a time and under conditions sufficient for said agent to induce cardiomyocyte FPR1 activation.

Preferably, said myocardial infarction is acute myocardial infarction.

Without limiting the present invention to any one theory or mode of action, the formyl peptide receptors (FPR) belong to a class of G protein-coupled receptors involved in chemotaxis. These receptors were originally identified by their ability to bind N-formyl peptides such as N-formyl-methionine produced by the degradation of either bacterial or host cells. The formyl peptide receptor (FPR) belongs to the class of receptors possessing seven hydrophobic transmembrane domains. The conformation of the FPR is stabilized by several interactions. These include potential salt bridge formation between Arg84-Arg205, Lys85-Arg205, and Lys85-Asp284 which help to determine the three-dimensional structure of transmembrane domains, as well as positively charged residues (Arg, Lys) which interact with negatively charged phosphates. Furthermore, residue Arg163 may interact with the ligand binding pocket of the second extracellular loop of the FPR. The FPR2 member of the human formyl peptide receptor FPR family (also comprising FPR1 and FPR3) is now identified as the receptor responsible for some of the biological activities of ANX-A1, its N-terminal peptide and $LxA_4$ (Ye et al., 2009) and a large number of other ligands. The FPR1 and FPR2 receptors are widely distributed in tissues and on different cell types, being most prominently expressed on cell types involved with inflammatory processes, whereas FPR3 is thought to be highly expressed only on dendritic cells. FPR2 and FPR3 however share ≥70% level of sequence homology (Ye et al., 2009). Reports of the expression of FPR2s on different types of tumour cells are growing in number. Reference to "FPR1" should be understood as a reference to all forms of FPR1 and any isoforms which may arise from alternative splicing of FPR1 mRNA or mutant or polymorphic forms thereof.

As detailed hereinbefore, the myocardial tissue damage which is the subject of the present invention is induced by ischaemia. By "ischaemia" it is meant a myocardial ischemic event, more specifically a reduction in oxygenated blood flow to the myocardial tissue. This reduction is usually due to the occurrence of a restriction in blood supply, usually due to the partial or complete blockage of one or more arteries around the heart. The restriction to blood flow may be to all or just some of the myocardial tissue. It may also be a transient restriction, which naturally rectifies itself, or it may be non-transient in that it requires medical intervention to be partially or fully cleared. The ischaemia of the present invention is of a type (in terms of its duration and the level of occlusion) that leads to some degree of myocardial tissue damage (myocardial infarction) occurring in a region of the myocardial tissue. Without limiting the present invention to any one theory or mode of action, restriction of blood flow to the myocardial tissue can result from any of a wide range of events including, but not limited to, atherosclerotic plaque formation which progressively narrows the coronary arteries (coronary atherosclerosis), disruption of an atherosclerotic plaque in an epicardial coronary artery which leads to a clotting cascade sometimes resulting in total occlusion of the artery, rupture of an atherosclerotic plaque which also promotes a thrombus (blot clot formation), obstruction by a blood clot which has dislodged from its original site and has travelled through the arteries and become lodged in an artery which services the heart, diffuse narrowing of arterioles and other small vessels within the heart, surgical clamping of an artery or angioplasty.

Still without limiting the present invention to any one theory or mode of action, in many cases of myocardial ischaemia, some level of blood supply will be restored to the myocardial tissue. This may occur as a result of a naturally occurring event or it may occur as a result of medical intervention such as chemical dissolution of an occluding thrombus, administration of vasodilator drugs, angioplasty, catheterisation, insertion of an arterial stent or artery bypass graft surgery. However, restoration of blood flow after a period of ischaemia, although ultimately necessary, can actually cause more damage than the ischaemia itself. The reintroduction of oxygen to the myocardial tissue causes, inter alia, the production of oxygen free radicals. It is thought that the absence of oxygen and nutrients from the blood, during the period of ischaemia, creates a condition in which the restoration of circulation results in still further inflammation and oxidative damage through the induction of oxidative stress. This is termed "reperfusion injury" and is additive to the damage which occurs at the time of the initial hypoxia and subsequent ischaemia cascade as hereinbefore discussed. The types of damage which may be observed to occur at the sites of reperfusion include, but are not limited to, oedema with cellular swelling and disintegration, sarcolemma disruption, fragmentation of mitochondria, contraction bound necrosis, enzyme washout, calcium overload, haemorrhage or ventricular arrhythmias.

It has been determined that the method of the present invention is effective in minimising the extent of both ischaemia-induced myocardial tissue damage and the potentially more severe ischaemia-reperfusion-induced myocardial tissue damage. As detailed hereinbefore, one of the particularly unexpected and highly significant aspects of the present invention relates to the fact that the molecules of the present invention not only selectively activate cardiomyocyte FPR1 functionality, but they also selectively activate ERK/Akt-mediated signalling, which selectively facilitates cardioprotection but not intracellular $Ca^{2+}$ mobilisation thereby avoiding the extremely adverse side effect of cardiac tissue death caused by $Ca^{2+}$ overload.

Accordingly, in a related aspect the present invention is directed to a method of minimising the extent of ischaemia-reperfusion induced myocardial tissue damage in a mammal, said method comprising administering to said mammal an effective amount of a compound of structure (I):

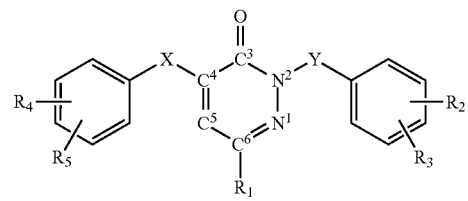

or a pharmaceutically acceptable salt, solvate or stereoisomer thereof, wherein
(a) X is $CH_2$;
   Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
     wherein $R_6$ is H;
      $R_7$ is $CH_3$, $C_2H_5$, $n-C_3H_7$, $i-C_3H_7$, $n-C_4H_9$, or $C_6H_5$;
     or
     $R_6$ is $CH_3$;
     $R_7$ is $C_2H_5$ or $CH_3$; and
   $R_1$ is $CH_3$;
or
(b) X is $CH_2$;
   Y is $CH_2CONH$; and
   $R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or
(c) X is NHCO or NHCONH;
   Y is $CH_2$; and
   $R_1$ is $CH_3$;
or
(d) X is NH;
   Y is $CH_2CONH$; and
   $R_1$ is $CH_3$;
or
(e) X is NHCO or CO;
   Y is $CH_2CONH$; and
   $R_1$ is $CH_3$;
or
(f) X is $CH_2$;
   Y is $CH_2CO$;
     wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and
   $R_1$ is $CH_3$;
or
(g) X is NHCONH, NHCO, or NH;
   Y of structure (I) is not present and instead the phenyl group substituted with $R_2$ and $R_3$ is directly bonded to the N2 of the pyridazinone ring; and
   $R_1$ is $CH_3$;
or
(h) X is $CH_2$;
   Y is $CH_2CONH$ or $CH(CH_3)CONH$;
     the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and $R_1$ is $CH_3$;
or
(i) X and the phenyl group substituted with $R_4$ and $R_5$ are not present;
  Y is $CH_2CONH$; and
  $R_1$ is $CH_3$;
or
(j) X and the phenyl group substituted with $R_4$ and $R_5$ are not present;
  Y is $CH_2CONH$;
  $R_1$ is $CH_3$; and
    the bond between C4 and C5 of the pyridazinone ring is a single bond;
or
(k) X is $NH_2$ and the phenyl group substituted with $R_4$ and $R_5$ is not present;
  Y is $CH_2CONH$; and
  $R_1$ is $CH_3$;
or
(l) X of structure (I) is not present and instead the phenyl group substituted with $R_4$ and $R_5$ is directly bonded to C4 of the pyridazinone ring;
  Y is $CH_2CONH$; and
  $R_1$ is $CH_3$;
or
(m) X is NH;
  Y is $CH_2CONH$;
  $R_1$ is $CH_3$; and
    C5 is additionally substituted with $COCH_3$;
  wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group; and
wherein said compound is administered for a time and under conditions sufficient for said agent to induce cardiomyocyte FPR1 activation.

In one embodiment of this aspect, said myocardial tissue damage is the loss of cellular viability and contractile functioning.

In another embodiment, said ischaemia-reperfusion-induced tissue damage is myocardial infarction-induced tissue damage and, more particularly, acute myocardial infarction-induced tissue damage.

In terms of compounds of structure (I) and without limiting the present invention to any one theory or mode of action, within a particular substituent or term defined herein, as used throughout the specification, there may be two or more groups of the same type (e.g., two alkyl groups or two aryl groups). Unless specifically stated to the contrary, each of these groups can be the same or different from every other of the same type.

The term "substituted" should be understood to mean that the specified group or moiety bears one or more substituents. Where any group can carry multiple substituents and a variety of possible substituents is provided, the substituents are independently selected and need not be the same. The term "unsubstituted" means that the specified group bears no substituents. The term "optionally substituted" means that the specified group is unsubstituted or substituted by one or more substituents.

Any asymmetric carbon atoms may be present in the (R)-, (S)-, or (R,S)-configuration, preferably in the (R)- or (S)-configuration, whichever is most active. Substituents at a double bond or a ring may be present in cis-(Z) or trans-(E) form.

The presently disclosed compounds may contain asymmetric centres on the molecule, depending upon the nature of the various substituents. In certain instances, asymmetry may also be present due to restricted rotation about the central bond adjoining the two aromatic rings of the specified compounds. It is intended that all isomers (including enantiomers and diastereomers), either by nature of asymmetric centres or by restricted rotation as described above, as separated, pure or partially purified isomers or racemic mixtures thereof, be included within the ambit of the present disclosure.

The term "halogen" or "halo" refers to fluorine (F, Fluoro-), bromine (Br, Bromo-), chlorine, (Cl, Chloro-), and iodine (I, Iodo-) atoms.

The terms "dihalogen", "trihalogen" and "perhalogen" refer to two, three and four substituents, respectively, each individually selected from the group consisting of fluorine, bromine, chlorine, and iodine atoms.

The term "alkyl" means a linear saturated monovalent hydrocarbon radical or branched (with single or multiple branching) saturated monovalent hydrocarbon radical, e.g., methyl, ethyl, propyl, 2-propyl, butyl (including all isomeric forms), or pentyl (including all isomeric forms), and the like.

The term "$C_1$-$C_6$ alkyl" means a linear saturated monovalent hydrocarbon radical of one to six carbon atoms or branched (with single or multiple branching) saturated monovalent hydrocarbon radical of three to six carbon atoms, e.g., methyl, ethyl, propyl, 2-propyl, butyl (including all isomeric forms), or pentyl (including all isomeric forms), and the like.

The term "alkoxy" means an —OR group where R is an alkyl group as defined herein, e.g., methoxy, ethoxy, propoxy, isopropoxy, and the like.

The term "haloalkyl" means an alkyl group substituted with one or more halogen, specifically one to five halogen atoms, e.g., trifluoromethyl, 2-chloroethyl, 2,2-difluoroethyl, and the like.

The term "haloalkoxy" means an —OR' group where R' is haloalkyl as defined herein, e.g., trifluoromethoxy, 2,2,2-trifluoroethoxy, and the like.

The word "compound" should be understood to cover any and all isomers (e.g., enantiomers, stereoisomers, diastereomers, rotamers, and tautomers), racemates or any mixture of isomers, prodrugs, and any pharmaceutical acceptable salt of said compound. Where the plural form is used for compounds, salts, and the like, this is taken to mean also a single compound, salt, or the like.

A "pharmaceutically acceptable salt" of a compound disclosed herein means a salt that is pharmaceutically acceptable and that possesses the desired pharmacological activity of the parent compound. It is understood that the pharmaceutically acceptable salts are non-toxic. Additional information on pharmaceutically acceptable salts can be found in *Remington's Pharmaceutical Sciences*, 17$^{th}$ ed., Mack Publishing Company, Easton, Pa., 1985, or S. M. Berge et al., "Pharmaceutical Salts", *J. Pharm. Sci.,* 1977, 66, 1-19, both of which are incorporated herein by reference.

Examples of pharmaceutically acceptable acid addition salts include those formed with inorganic acids such as hydrochloric acid, hydrobromic acid, sulphuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulphuric acid, gluconic acid, glutamic acid, hydroxynaphthoic acid, salicyclic acid, stearic acid, muconic acid, p-toluenesulfonic acid, and the like.

Examples of pharmaceutically acceptable base addition salts include those formed where an acidic proton present in the parent compound is replaced by metal ion, such as sodium, potassium, lithium, ammonium, calcium, magnesium, iron, zinc, copper, manganese, aluminium salts, and the like. Specific salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

The term "prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compound of this invention include, but are not limited to, alkyl esters (for example with between about one and about six carbons), the alkyl group is a linear or branched (with single or multiple branching) chain. Acceptable esters also include cycloalkyl esters and arylalkyl esters such as, but not limited to, benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods.

As would be appreciated by the skilled person, the method of the present invention is particularly useful for therapeutically or prophylactically treating conditions characterised by ischaemia-induced or ischaemia-reperfusion-induced myocardial tissue damage.

Accordingly, in a related aspect there is provided a method of therapeutically or prophylactically treating a condition characterised by ischaemia-induced myocardial tissue damage or ischaemia-reperfusion-induced myocardial tissue damage in a mammal, said method comprising administering to said mammal an effective amount of a compound of structure (I):

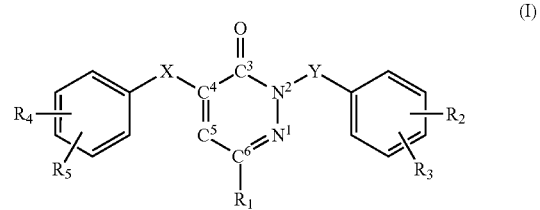

or a pharmaceutically acceptable salt, solvate or stereoisomer thereof, wherein (a) X is $CH_2$;
   Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
      wherein $R_6$ is H;
         $R_7$ is $CH_3$, $C_2H_5$, n-$C_3H_7$, n-$C_4H_9$, or $C_6H_5$;
         or
         $R_6$ is $CH_3$;
         $R_7$ is $C_2H_5$ or $CH_3$; and
      $R_1$ is $CH_3$;
or
(b) X is $CH_2$;
   Y is $CH_2CONH$; and
   $R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or
(c) X is NHCO or NHCONH;
   Y is $CH_2$; and
   $R_1$ is $CH_3$;
or
(d) X is NH;
   Y is $CH_2CONH$; and
   $R_1$ is $CH_3$;
or
(e) X is NHCO or CO;
   Y is $CH_2CONH$; and
   $R_1$ is $CH_3$;
or
(f) X is $CH_2$;
   Y is $CH_2CO$;
      wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and
   $R_1$ is $CH_3$;
or
(g) X is NHCONH, NHCO, or NH;
   Y of structure (I) is not present and instead the phenyl group substituted with $R_2$ and $R_3$ is directly bonded to the N2 of the pyridazinone ring; and
   $R_1$ is $CH_3$;
or
(h) X is $CH_2$;
   Y is $CH_2CONH$ or $CH(CH_3)CONH$;
      the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and $R_1$ is $CH_3$;
or
(i) X and the phenyl group substituted with $R_4$ and $R_5$ are not present;
  Y is $CH_2CONH$; and
  $R_1$ is $CH_3$;
or
(j) X and the phenyl group substituted with $R_4$ and $R_5$ are not present;
  Y is $CH_2CONH$;
  $R_1$ is $CH_3$; and
    the bond between C4 and C5 of the pyridazinone ring is a single bond;
or
(k) X is $NH_2$ and the phenyl group substituted with $R_4$ and $R_5$ is not present;
  Y is $CH_2CONH$; and
  $R_1$ is $CH_3$;
or
(l) X of structure (I) is not present and instead the phenyl group substituted with $R_4$ and $R_5$ is directly bonded to C4 of the pyridazinone ring;
  Y is $CH_2CONH$; and
  $R_1$ is $CH_3$;
or
(m) X is NH;
  Y is $CH_2CONH$;
  $R_1$ is $CH_3$; and
  C5 is additionally substituted with $COCH_3$;
    wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group; and
wherein said compound is administered for a time and under conditions sufficient for said agent to induce cardiomyocyte FPR1 activation.

In one embodiment, said condition is coronary atherosclerosis, coronary blood clot formation, diffuse narrowing of the cardiac arterioles, coronary artery surgical clamping, angioplasty, myocardial infarction, acute myocardial infarction, very low blood pressure, trauma, hemorrhaging or severe infection.

In still another embodiment, said tissue damage includes myocardial inflammation, loss of contractile function, cellular necrosis, cellular apoptosis, fibrosis, myocardial tissue remodelling, infarct size and/or left ventricular function.

The subject of the treatment is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably the mammal is a human or primate. Most preferably the mammal is a human.

An "effective amount" means an amount necessary to at least partly attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

Reference herein to "therapeutic" and "prophylactic" treatment is to be considered in its broadest context. The term "therapeutic" does not necessarily imply that the condition is treated until total recovery. Similarly, "prophylactic" does not necessarily mean that the patient will not develop some degree of cardiac tissue damage. Accordingly, therapeutic and prophylactic treatment includes amelioration of the symptoms of cardiac damage or preventing or otherwise reducing the risk of developing cardiac damage. The term "prophylactic" may be considered as reducing the severity or extent of damage.

In accordance with the preceding aspects and embodiments, the compound of structure (I) may be:

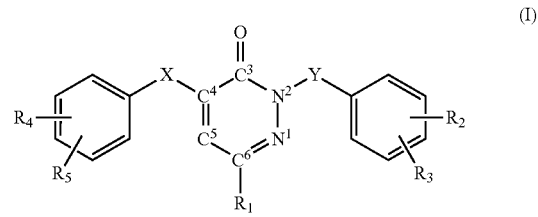

(I)

wherein
(a) X is $CH_2$;
  Y is $CH_2CONH$; and
  $R_1$ is $CH_3$;
or
(b) X and the phenyl group substituted with $R_4$ and $R_5$ are not present;
  Y is $CH_2CONH$; and
  $R_1$ is $CH_3$;
or
(c) X and the phenyl group substituted with $R_4$ and $R_5$ are not present;
  Y is $CH_2CONH$;
  $R_1$ is $CH_3$; and
    the bond between C4 and C5 of the pyridazinone ring is a single bond;
or
(d) X is $NH_2$ and the phenyl group substituted with $R_4$ and $R_5$ is not present;
  Y is $CH_2CONH$; and
  $R_1$ is $CH_3$;
or
(e) X of structure (I) is not present and instead the phenyl group substituted with $R_4$ and $R_5$ is directly bonded to C4 of the pyridazinone ring;
  Y is $CH_2CONH$; and
  $R_1$ is $CH_3$;
or
(f) X is $CH_2$;
  Y is $C(R_6R_7)CONH$;
    wherein $R_6$ is H;
    $R_7$ is $CH_3$, $C_2H_5$, n-$C_3H_7$, i-$C_3H_7$, n-$C_4H_9$, or $C_6H_5$;
    or
    $R_6$ is $CH_3$;
    $R_7$ is $C_2H_5$ or $CH_3$; and
  $R_1$ is $CH_3$;
or
(g) X is $CH_2$;
  Y is $CH(CH_3)CONH$
  $R_1$ is $CH_3$;
or
(h) X is $CH_2$;
  Y is $CH_2CONH$ or $CH(CH_3)CONH$;
    the phenyl group substituted with $R_4$ and $R_5$ and bonded to X of structure (I) is replaced with 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and $R_1$ is $CH_3$;

wherein $R_2$, $R_3$, $R_4$ and $R_5$ are independently hydrogen, halogen, alkyl, alkoxy, haloalkyl, haloalkoxy, alkylsulfide, cyano, nitro, or $R_2$ and $R_3$ and/or $R_4$ and $R_5$ is a bridged di-alkoxy group;

or (i) X is $CH_2$;

Y is $CH(CH_3)CONH$ $R_1$ is $CH_3$;

wherein $R_2$ is hydrogen and $R_3$ is para-bromine, and $R_4$ and $R_5$ are independently hydrogen, halogen, alkyl, alkoxy, haloalkyl, haloalkoxy, alkylsulfide, cyano, or nitro;

or (j) X is $CH_2$;

Y is $CH(CH_3)CONH$ $R_1$ is $CH_3$;

wherein $R_2$ and $R_3$ are independently hydrogen, halogen, alkyl, alkoxy, haloalkyl, haloalkoxy, alkylsulfide, cyano, or nitro, and $R_4$ is hydrogen and $R_5$ is meta-methoxy;

or (k) X is $CH_2$;

Y is $CH(CH_3)CONH$ $R_1$ is $CH_3$;

wherein $R_2$ is hydrogen and $R_3$ is para-bromine, and $R_4$ is hydrogen and $R_5$ is meta-methoxy;

or a pharmaceutically acceptable salt, solvate or stereoisomer thereof.

Compounds of structure (I) include, but are not limited to:

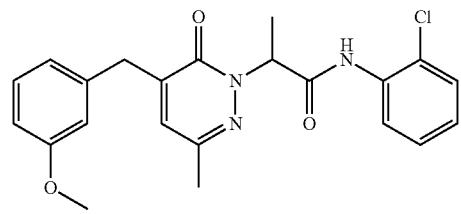

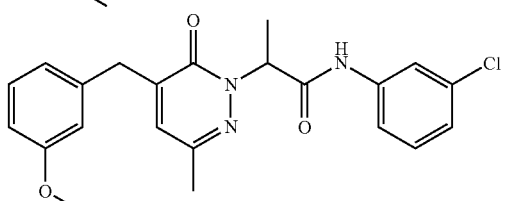

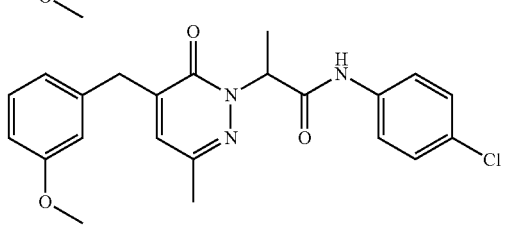

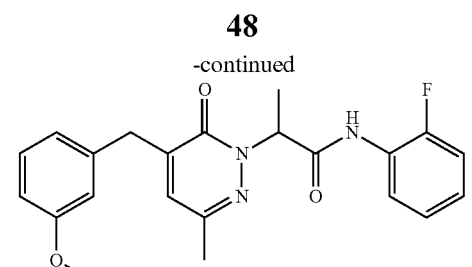

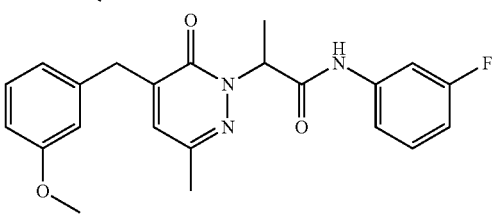

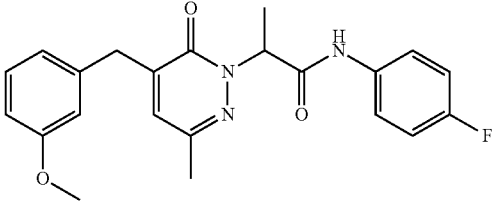

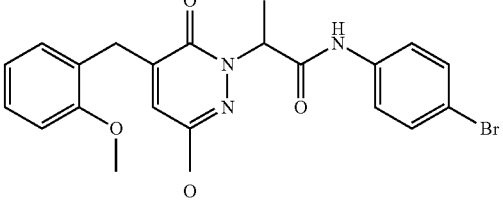

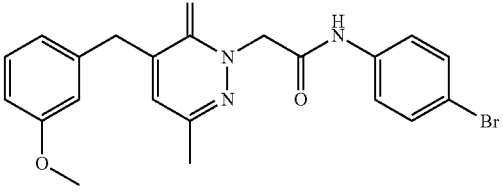

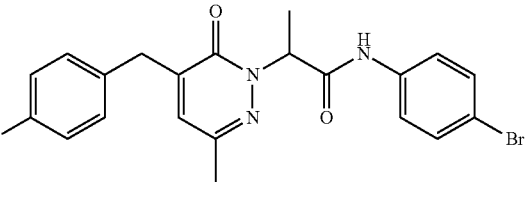

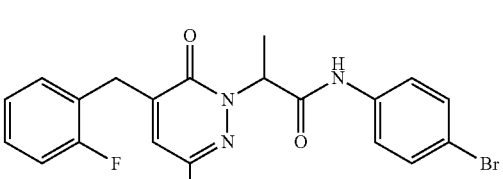

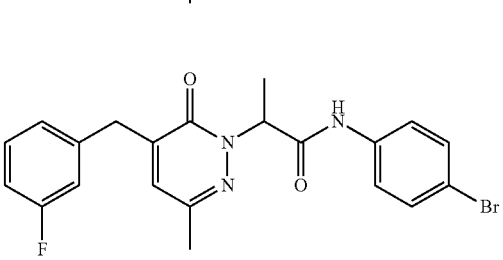

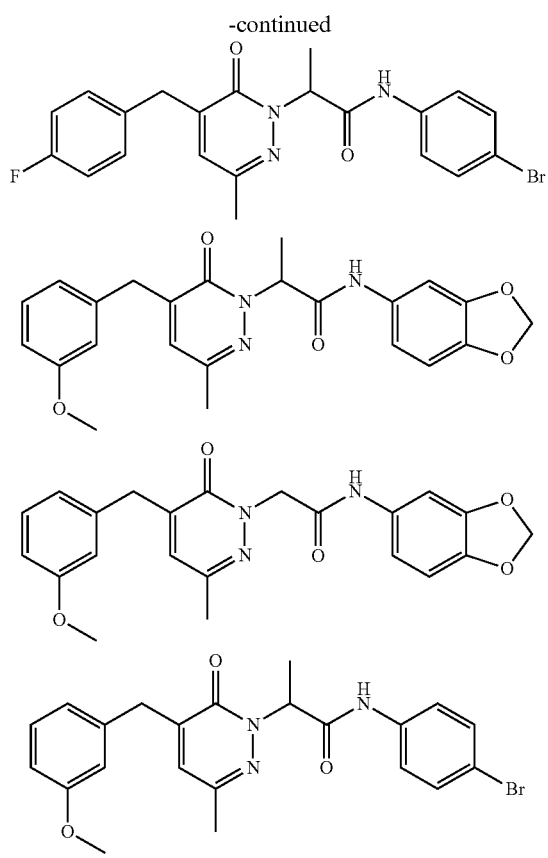
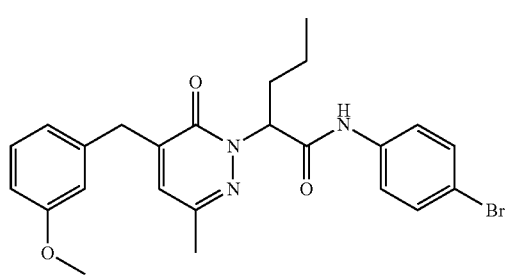
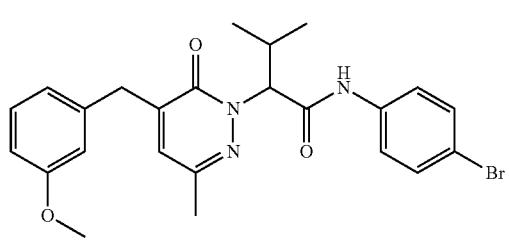
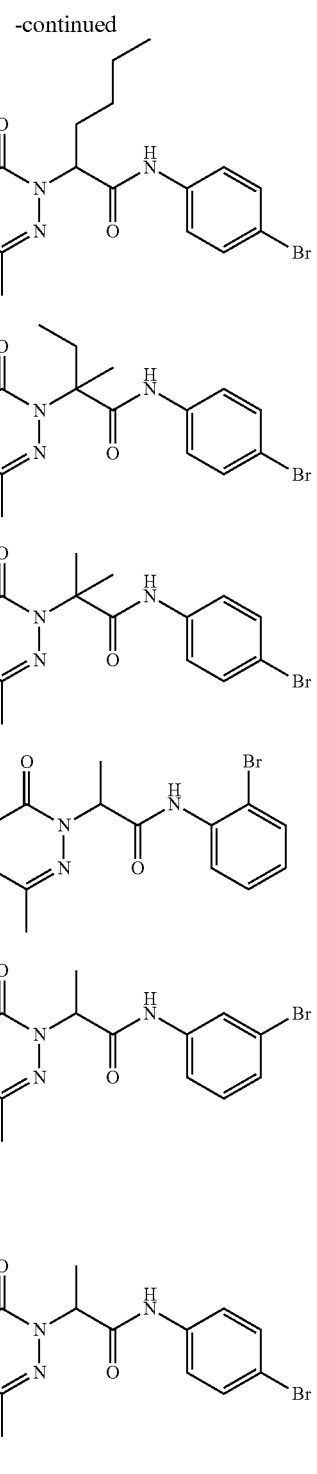
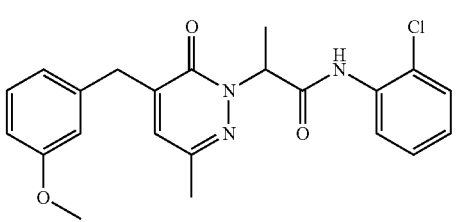

-continued
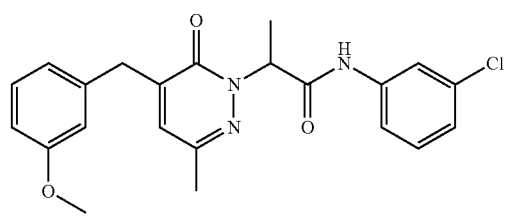
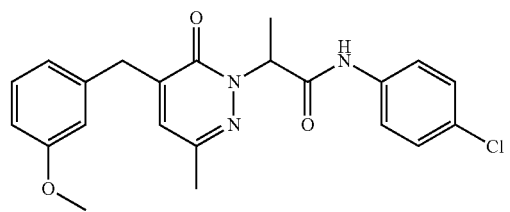
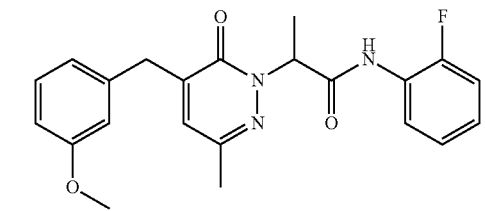
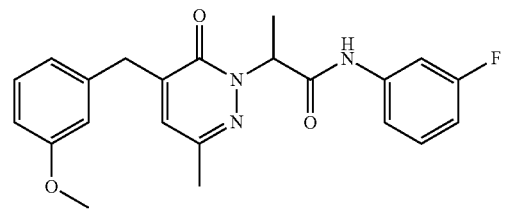
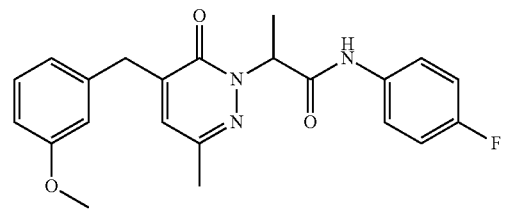
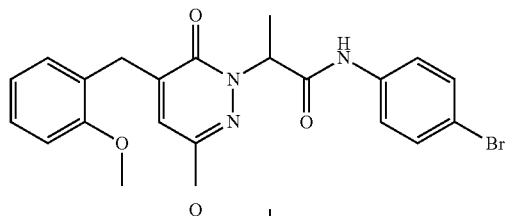
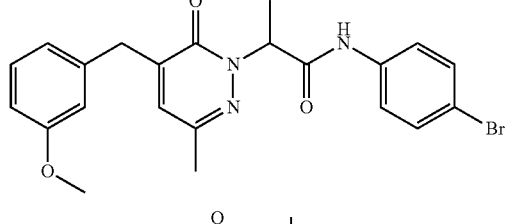
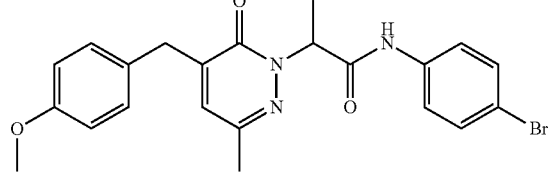
-continued
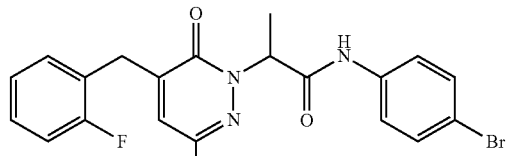
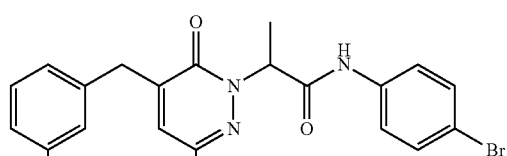
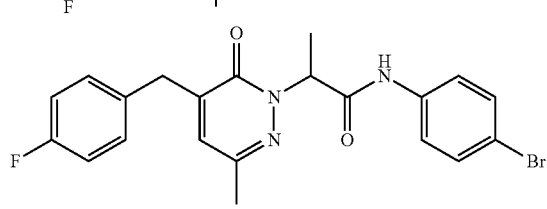
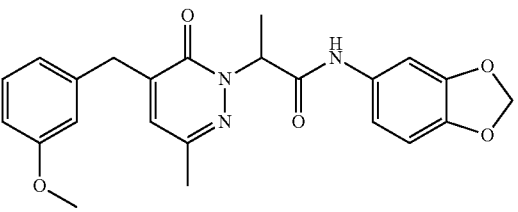
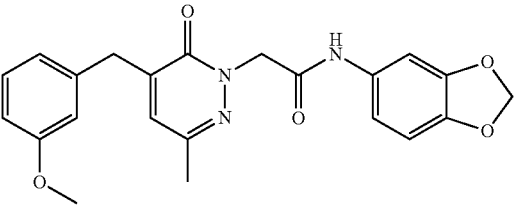
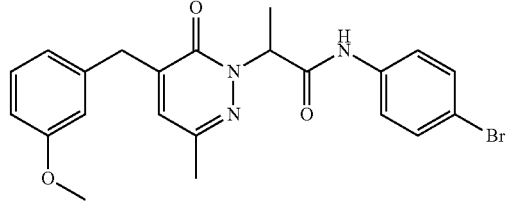
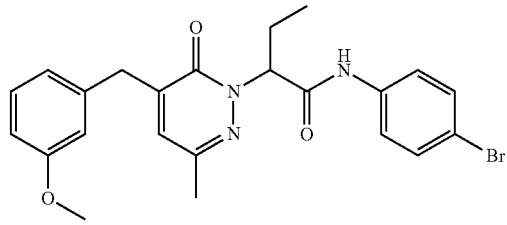
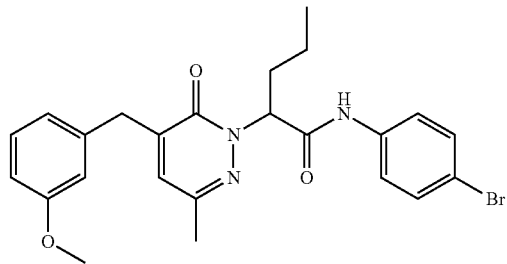

53
-continued
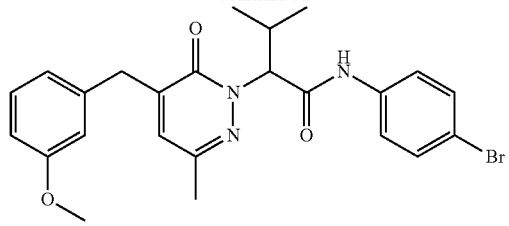
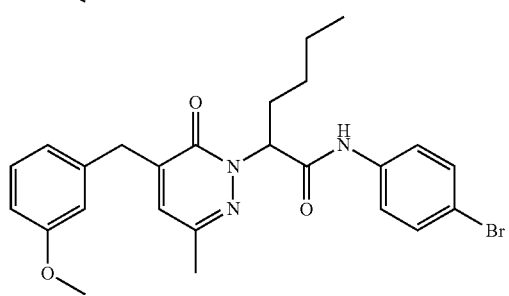
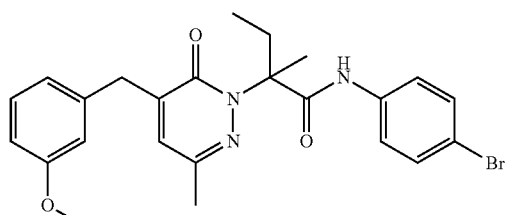
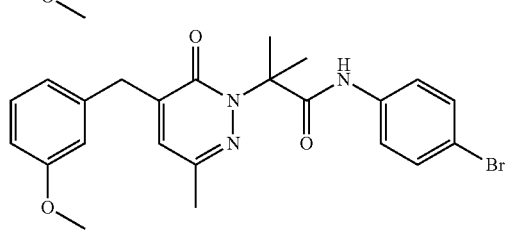
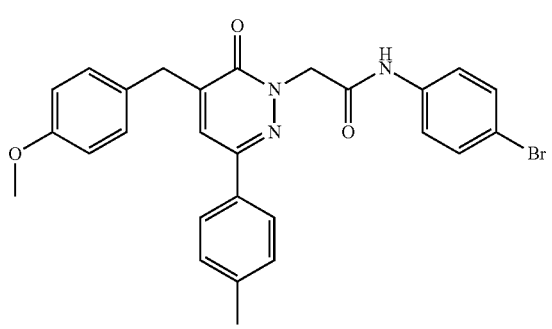
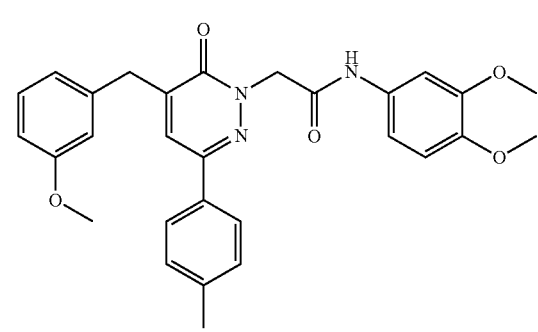
54
-continued
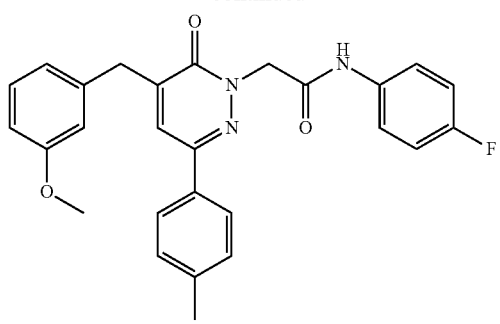
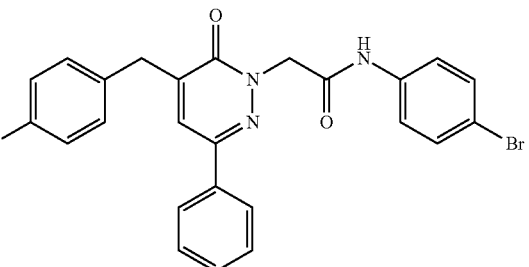
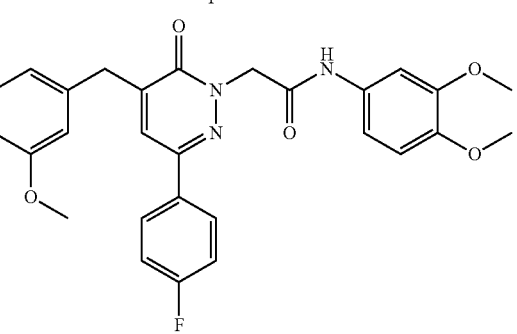
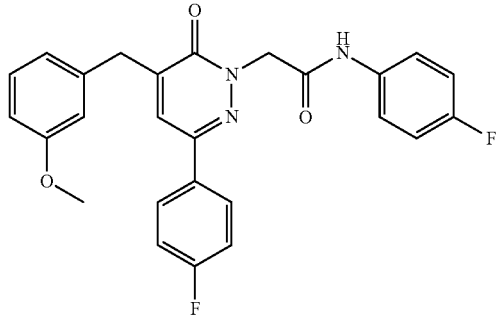
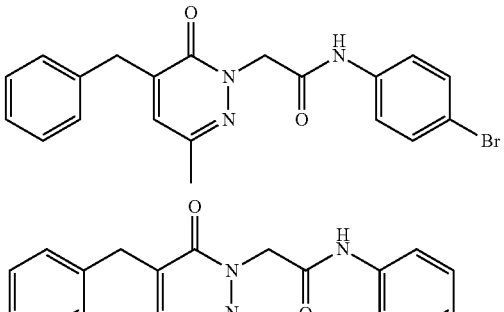
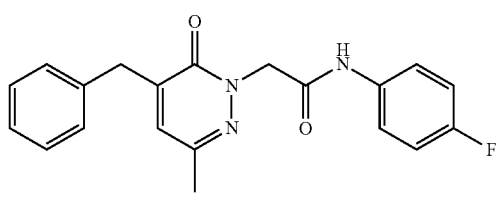

55
-continued
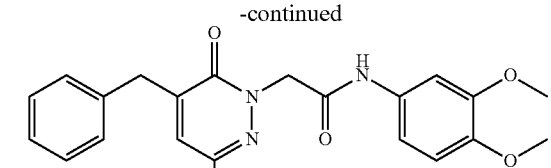
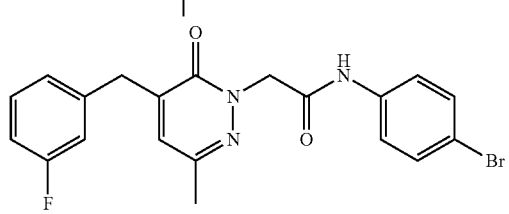
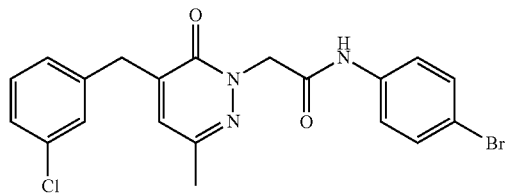
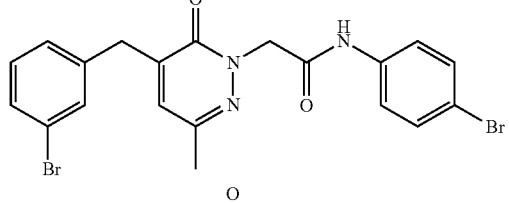
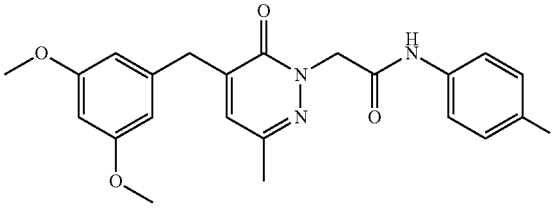
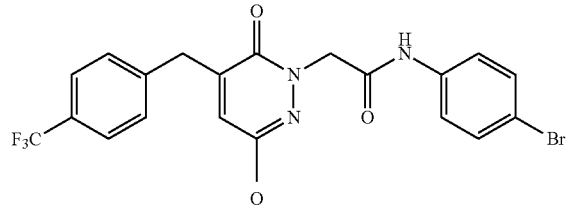
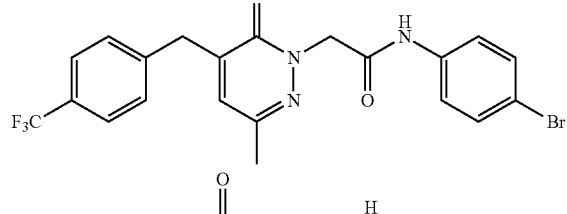
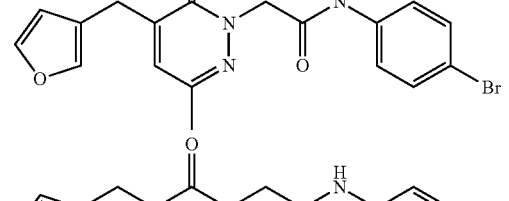
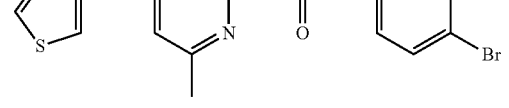
56
-continued
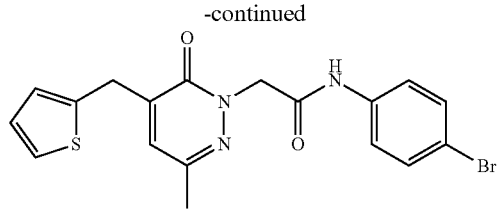
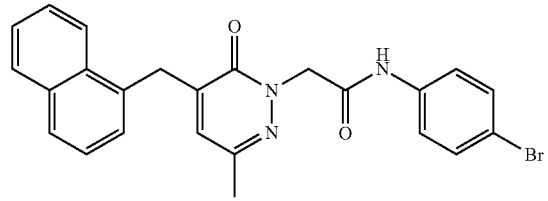
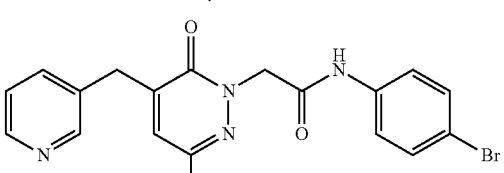
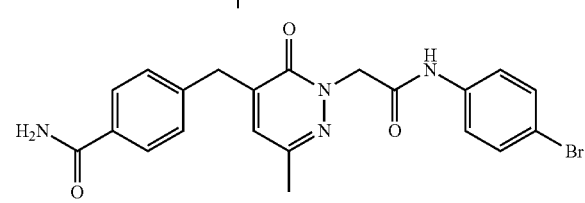
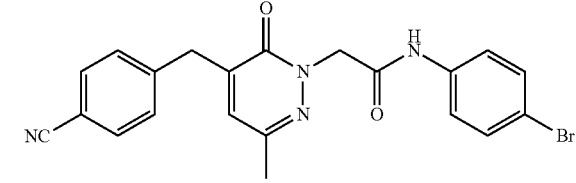
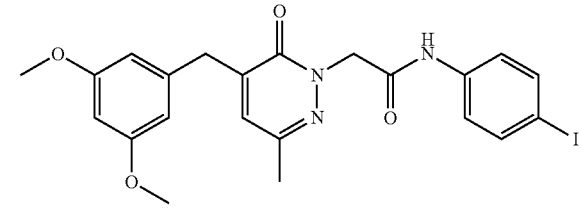
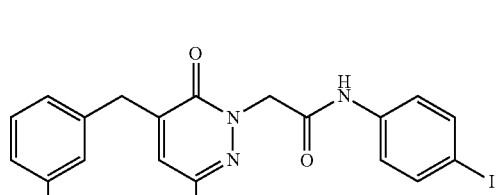
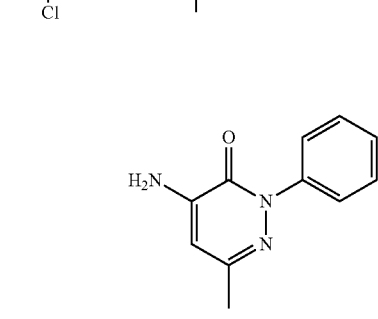

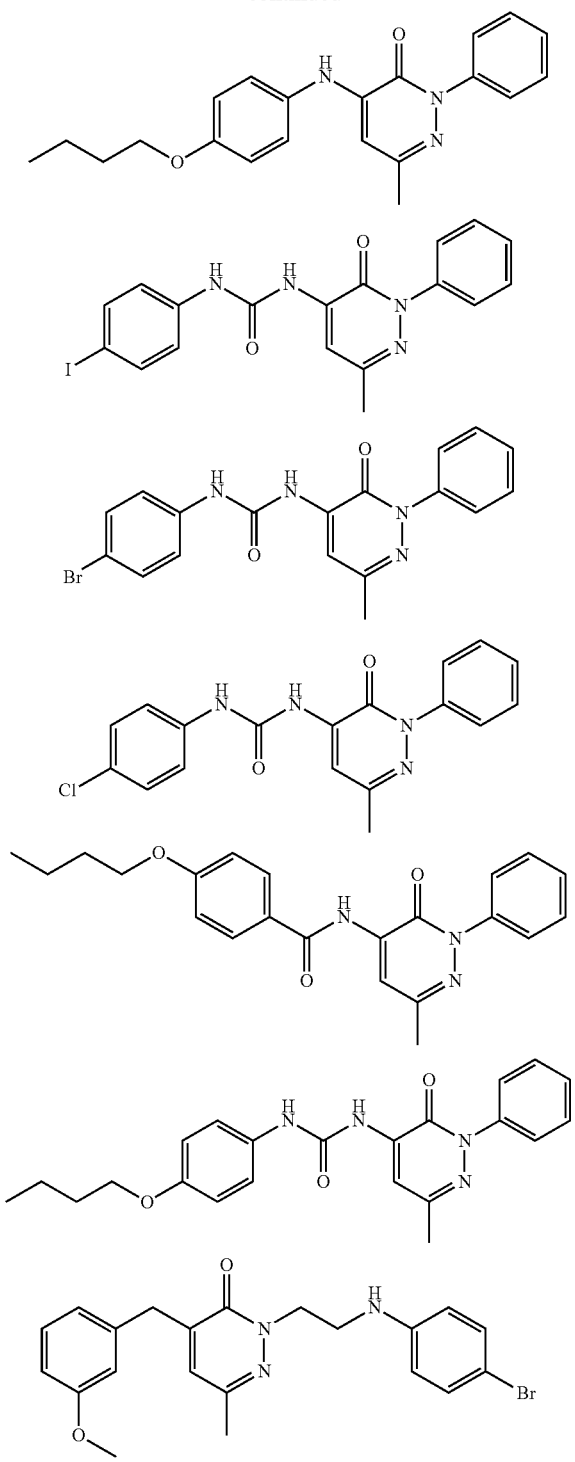
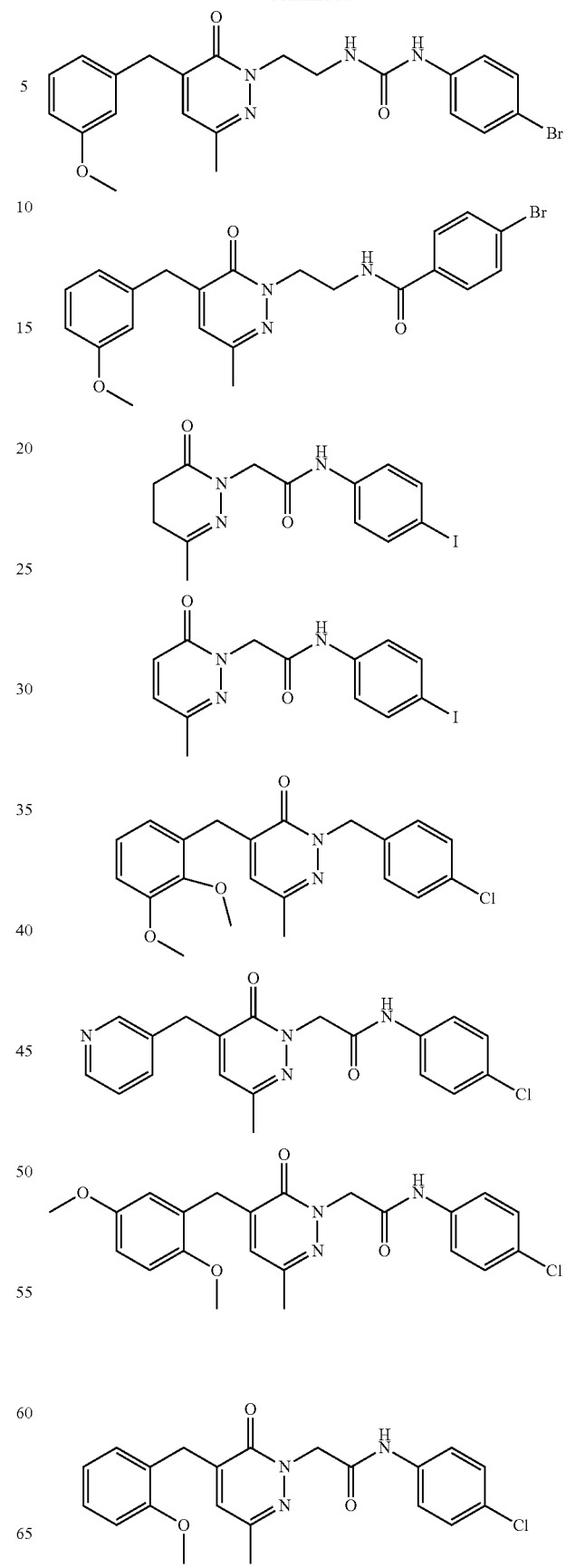

-continued

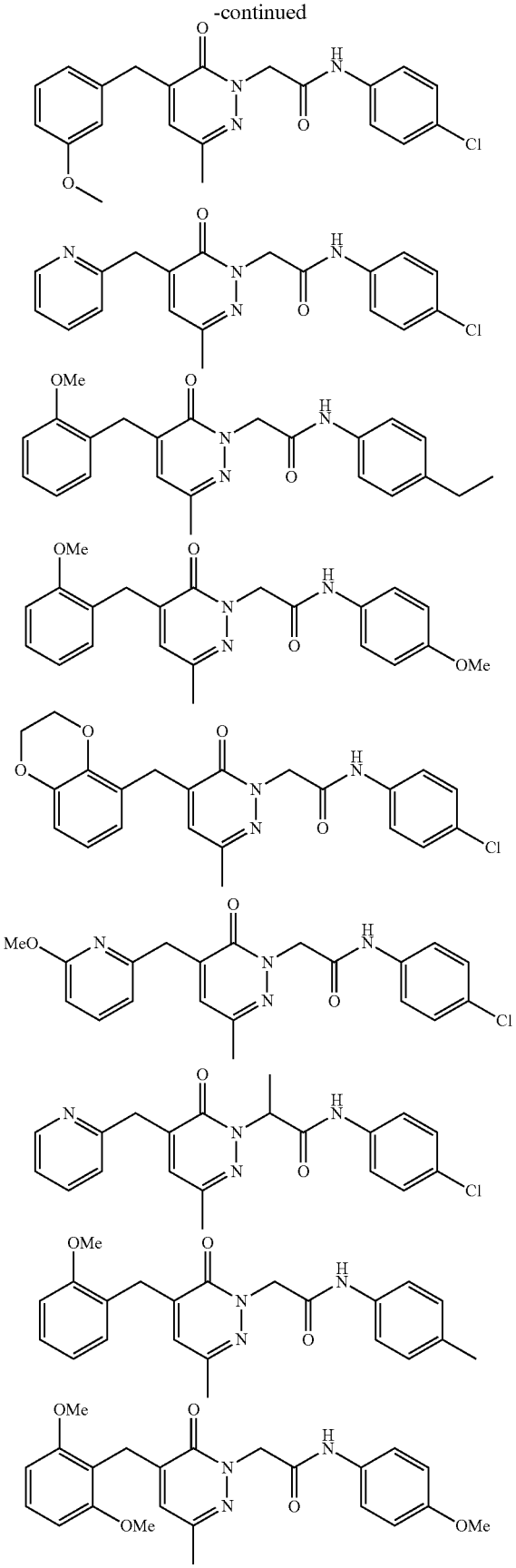

and pharmaceutically acceptable salts, solvates or stereoisomers thereof.

The compounds disclosed can be prepared in accordance with the method of Cilibrizzi et al. in *J. Med. Chem.* 2009, 52, 5044-5057, Cilibrizzi et al., *Bioorg. Med. Chem.* 2012, 20, 3781-3792, Crocetti et al., *Drug Dev. Res.* 2013, 74, 259-271, and Giovannoni et al., *Eur. J. Med. Chem.* 2013, 65, 512-528. The starting materials and intermediates used in the synthesis of compounds of this invention are generally commercially available or may be prepared by conventional methods of organic chemistry. Suitable methods for the synthesis of compounds of this invention and intermediates thereof are described, for example, in J. March, *Advanced Organic Chemistry*, 3rd Edition (John Wiley & Sons, New York, 1985); D. C. Liotta and M. Volmer, eds, *Organic Syntheses Reaction Guide* (John Wiley & Sons, Inc., New York, 1991); R. C. Larock, *Comprehensive Organic Transformations* (VCH, New York, 1989), H. O. House, *Modern Synthetic Reactions* 2nd Edition (W. A. Benjamin, Inc., Menlo Park, 1972); and N. S. Simpkins, ed. 100 *Modern Reagents* (The Royal Society of Chemistry, London, 1989).

Compounds of structure (I) of the present disclosure were prepared according to the procedures of Cilibrizzi et al., *J. Med. Chem.* 2009, 52, 5044-5057, Cilibrizzi et al., *Bioorg. Med. Chem.* 2012, 20, 3781-3792, Crocetti et al., *Drug Dev. Res.* 2013, 74, 259-271, and Giovannoni et al., *Eur. J. Med. Chem.* 2013, 65, 512-528.

Yet another aspect of the present invention is directed to the use of the compounds as hereinbefore defined in the manufacture of a medicament for minimising the extent of ischaemia-induced myocardial tissue damage in a mammal.

In still yet another aspect, there is provided the use of the compounds as hereinbefore defined in the manufacture of a medicament for minimising the extent of ischaemia-reperfusion-induced myocardial tissue damage in a mammal.

In accordance with these aspects, in one embodiment said myocardial tissue damage is the loss of cellular viability and contractile function.

In yet another aspect, said myocardial tissue damage is myocardial infarction induced tissue damage and, more particularly, acute myocardial infarction induced tissue damage.

The compounds of the invention can be administered in a variety of unit dosage forms depending upon the method of administration. Dosages for typical modulatory compounds are well known to those of skill in the art. Such dosages are typically advisory in nature and are adjusted depending on the particular therapeutic context, patient or organ tolerance, etc. The amount of agent adequate to accomplish this is defined as a "therapeutically effective dose." The dosage schedule and amounts effective for this use, i.e., the "dosing regimen," will depend upon a variety of factors, including the condition of the heart, the pre-existence or not of damage onset, the pharmaceutical formulation and concentration of active agent, and the like. In calculating the dosage regimen for an organ, the mode of administration also is taken into consideration. The dosage regimen must also take into consideration the pharmacokinetics, i.e., the compound's rate of absorption, bioavailability, metabolism, clearance, and the like. (See, e.g., the latest Remington's; Egleton and Davis 1997 *Peptides* 18:1431-1439; Langer 1990 *Science* 249:1527-1533).

The compounds may be administered by any convenient means and is contemplated to exhibit therapeutic activity when administered in an amount which depends on the particular case. The variation depends, for example, on the human or animal and the modulatory agent chosen. A broad range of doses may be applicable. Considering a patient, for example, from about 0.1 mg to about 1 mg of compound may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The compound may be administered in a convenient manner such as by the oral, intravenous (where water soluble), intraperitoneal, intramuscular, subcutaneous, intradermal or suppository routes or implanting (e.g. using slow release molecules). It may be administered in the form of pharmaceutically acceptable nontoxic salts, as described hereinbefore. If the active ingredient is to be administered in tablet form, the tablet may contain a binder such as tragacanth, corn starch or gelatin; a disintegrating agent, such as alginic acid; and a lubricant, such as magnesium stearate.

Routes of administration include, but are not limited to, intravenously, intraperitoneally, subcutaneously, intradermally, intramuscularly, intrathecally, infusion, orally, via IV drip, patch and implant.

In accordance with these methods, the compound defined in accordance with the present invention may be coadministered with one or more other compounds or molecules. By "coadministered" is meant simultaneous administration in the same formulation or in two different formulations via the same or different routes or sequential administration by the same or different routes. For example, the subject compound may be administered together with an agent in order to enhance its effects. By "sequential" administration is meant a time difference of from seconds, minutes, hours or days between the administration of the two types of molecules. These molecules may be administered in any order.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal antagonists, for example, parabens, chlorobutanol, phenol, sorbic acid, thimerosal and the like. In many cases, it will be preferable to include isotonic antagonists, for example, sugars or sodium chloride. Prolonged absorption of the injectable compositions can be brought about by the use in the compositions of antagonists delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating antagonist such as corn starch, potato starch, alginic acid and the like; a lubricant such as magnesium stearate; and a sweetening antagonist such as sucrose, lactose or saccharin may be added or a flavouring antagonist such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening antagonist, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention relates to G protein-coupled receptors (GPCRs), and more particularly to formyl peptide receptors (FPRs). Even more particularly, the present invention relates to the FPR1 subtype. The invention presented herein is based, in part, on agonism of the FPR1 subtype and in particular the selective activation of FPR1 ERK/Akt signalling. It has been determined that modulators selective for FPR1 ERK/Akt signalling provide an opportunity for the development of improved therapies related to the FPR1 subtype.

Accordingly, another aspect of the present invention is directed to a method of identifying a candidate compound that modulates the activity of a target receptor comprising:
   a) contacting receptor with a candidate compound,
   b) determining the binding of the candidate compound to the receptor;
   c) selecting for candidate compounds which activate the receptor;
wherein the target receptor is formyl peptide receptor subtype FPR1; and the candidate compound activates the FPR1 subtype to a greater degree than the activation by an endogenous ligand or substrate for the FPR1 subtype.

Preferably, said compound selectively activates ERK/Akt signalling.

In still other embodiments, the candidate compound may be a co-agonist, an irreversible agonist, or an inverse agonist.

In some embodiments, the candidate compound that modulates the activity of a target receptor may be an allosteric effector of the target receptor. An allosteric effector, in accordance with the present invention, may be an inhibitory or negative effector or may be a stimulatory or positive effector. An allosteric effect is accomplished by binding specifically to a site on the target receptor other than the native substrate binding site and thereby inhibits or stimulates the activity of the receptor.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Example 1

In Vitro Analysis

Materials and Methods

SurefireERK1/2 phosphorylation, Akt1/2/3 phosphorylation and cAMP accumulation kits were purchased from PerkinElmer Life and Analytical Science (Waltham, Mass., USA). FIp-IN Chinese hamster ovary (CHO) cells, Gateway plasmid, hygromycin B, Fluo-4M were obtained from Invitrogen (Carlsbad, Calif., USA). Dulbecco's modified eagle medium (DMEM) and fetal bovine serum (FBS) were purchased from Gibco (Gaithersburg, Md., USA) and JRH Biosciences (Lenexa, Kans., USA). $Ac_{2-26}$ was synthesized by Chemileliva (Chongqing, China), and BIDI-001 and BIDI-002 by Anthem Bioscience (Bangalore, India). All other materials were purchased from Sigma-Aldrich (St. Louis, USA) except where indicated, and were of analytic grade or higher.

Compounds: The following four compounds are referred to in the Examples.

BIDI-001

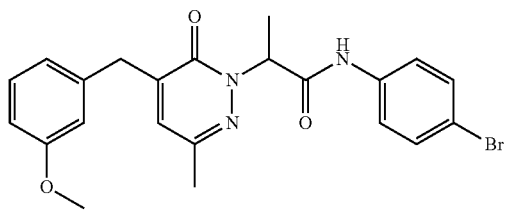

(also referred to as Cmpd 17b)

BIDI-002

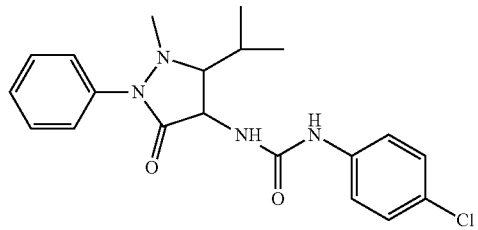

(also referred to as Cmpd 43)

Cmpd 10394

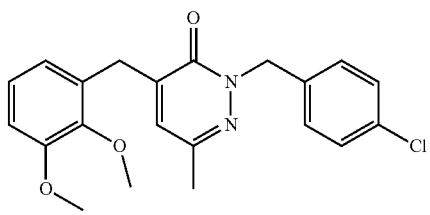

Cmpd 10396

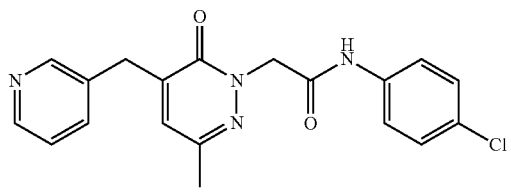

Animals: All animal research was conducted in accordance with the National Health and Medical Research of Australian guidelines, and approval was obtained from the Alfred Medical Research of Education Precinct (AMREP) Animal Ethics Committee. The neonatal (1-2 day old) Sprague-Dawley rats (mixed sex), were bred and housed in the AMREP Animal Centre.

Isolation of primary neonatal rat ventricular cardiomyocyte: All materials used for cardiomyocyte isolation were of tissue culture grade. Cardiomyocyte isolation was performed by serial enzymatic digestions, as previously described (Irvine, J C et al, AJP, 2013). Cardiomyocyte were suspended in sterile DMEM, supplemented with 100 U/mL penicillin, 100 μg/mL streptomycin, and 10% FCS. The myocyte-rich cell suspension was preplated twice (45 min at 37° C.) to reduce fibroblast contamination. Cardiomycte was then plated onto 12-well plates at $0.5 \times 10^6$ for lactate dehydrogenase (LDH) assay in the presence of 1% 5-bromo-2'-deoxyuridine (BrdU, to limit proliferation of any remaining fibroblasts).

Simulated ischaemic-reperfusion in neonatal rat cardiomyocytes: The medium for cardiomyocytes was changed to serum-free low glucose DMEM after at least 48 h after isolation. Cardiomyocytes were then subjected to 6 h hypoxia (95% $N_2$-5% $CO_2$, using a hypoxia chamber (QNA International, Melbourne, Australia) with subsequent 48 h reoxygenation, all at 37° C. to simulate ischaemia-reperfusion (I-R). The optimal concentrations of $Ac_{2-26}$, BIDI-001, BIDI-002 (over 0.3-3 μM) in hypoxic cardiomyocytes were determined initially in pilot studies; 1 μM for all agents was demonstrated most effective and was used in all subsequent cardiomyocyte studies. The culture medium of all normoxic or ischaemic cardiomyocytes were replaced with fresh drug solutions in fresh, sterile-filtered Krebs' buffer (118 mM NaCl, 4.8 mM KCl, 1.2 mM $KH_2PO_4$, 1.2 mM $MgSO_4$, 25 mM NaHCO$_3$, 50 mM EDTA, 100 mM CaCl$_2$). Agonists were dissolved in DMEM or Krebs' buffer and were present for the full duration of hypoxia and reoxygenation. At the end of 48 h reoxygenation, culture supernatant aliquots was collected on ice and stored at −80° C. for assessment of cardiomyocyte injury. Samples were thawed on ice, and cell injury assessment determined via the level of LDH released into the supernatant, using the Cyto-Tox-One™ Homogeneous Membrane Integrity Assay as per manufacture's instruction (Promega Inc, Dane Country, Wis., USA). To confirm the extent of cardiomyocyte injury, levels of cTn in the supernatant were also evaluated, using a commercially available high-sensitivity rat cTnI ELISA kit (Life Diagnostic Inc, West Chester, Pa., USA) as per manufacturer's instructions.

cDNDA construct and generation of stable cell lines: cDNA in pcDNA3.1$^+$ encoding the human formyl peptide receptors (FPR) subtypes, hFPR1, hFPR2 and hFPR3 was obtained from Invitrogen. The sequences for 3 hFPR receptors were amplified by PCR and cloned into the Gateway entry vector, pDONR202™, using the BP clonase enzyme mix, according to the manufactures' instructions (Invitrogen Inc, Carlsbad, Calif., USA). All hFPR receptors constructs in pDONR201™ were subsequently transfected into the pEF5/FRT/V5/dest vector using the LR clonase enzyme mix (Invitrogen). Receptor constructs (pEF5/FRT/V5/dest) were used to transfect Flp-In CHO cells as described previously (Valant C et al., PNAS, 2014). Cells were selected using 500 μg/mL hydromycin to generate cell lines stably expressing each receptor construct. Cells were maintained and cultured in high glucose DMEM supplemented with 10% FBS, 16 mM HEPES and 500 μg/mL hydromycin at 37° C. under a humidified atmosphere containing 5% CO$_2$.

In the various assays described below, cells were plated into 96-well transparent cell culture plates at 4×10$^4$ cells per well, cultured overnight in serum-free media at 37° C. in 5% CO$_2$.

Intracellular calcium mobilization: Intracellular calcium mobilization was assayed as described previously (Keov, P et al., 2014). Briefly, cells were washed once using HEPES buffered saline (HBS) solution [150 mM NaCl, 2.2 mM CaCl$_2$, 2.6 mM KCl, 1.2 mM MgCl2, 10 mM HEPEs, 10 mM D-Glucose, 0.5% (w/v) bovine serum albumin (BSA) and 4 mM probenecid] at pH 7.4, then treated with Fluo-4-AM (1 μM, in HBS/BSA/probenecid) for 60 min at 37° C. in 5% CO$_2$ in the dark. Cells were then further washed and placed in HBS/BSA/probenecid solution for ligation addition and assay using the FLEXstation 3 plate reader (Molecular Devices, Sunnyvale, Calif.). For all experiments, peak change in fluorescence signal was normalized to the cellular response to 100 μM ATP, which was used as an internal positive control.

Measurement of extracellular signal regulated kinase 1 and 2 phosphorylation (pERK1/2): Initial ERK1/2 phosphorylation at Thr202/Tyr204 time-course experiments were performed to determine the time at which ERK1/2 phosphorylation was maximal after stimulation by each agonist. Cells were seeded onto transparent 96-well cell culture plates at 4×10$^4$ cells per well. After 6 h, cells were washed once with PBS, and then incubated in serum-free DMEM overnight, to allow FBS-stimulated phosphorylated ERK1/2 levels to subside. Cell were then stimulated with agonist for 5 min with fMLP and BIDI-002, and 7 min for BIDI-001 (optimal maximal signal at this time point based on the initial time-course studies), and incubated at 37° C. in 5% CO$_2$. 10% (v/v) FBS was used as a positive control, with vehicle controls also included. The reaction was terminated by removal of study drugs and lysis of cells with 100 μL of SureFire lysis buffer (TGR Biosciences). Cell were lysed in SureFire lysis buffer and transferred to 384-well opaque proxiplates. Under low-light conditions, a 1:120 (v:v) dilution of AlphaScreen beads (both acceptor and donor):Surefire reaction buffer was prepared, which was mixed with the activation buffer in a ratio of 6:1 (v:v), respectively. Plates were incubated in the dark at 37° C. for 1 h before the fluorescence signal was measured by a Fusion-α plate reader (PerkinElmer Life and Analytical Sciences, Foster city, CA, USA) with standard AlphaScreen settings. Data were normalized to the maximal response elicited by 10% (v/v) FBS at the same time point.

Receptor mediated pERK1/2 levels were determined using the AlphaScreen™ ERK1/2 SureFire™ kit, as described previously (Keov, P et al., 2014). For all experiments, 10% FBS was used as internal positive control to stimulate pERK1/2, and which the maximum responses were used for normalization of data, whilst vehicle was used as negative control.

Measurement of Akt1/2/3 phosphorylation and Akt 1: The same lysate was used for measurement of Akt1/2/3 phosphorylation (Ser473) and Akt1 (Thr308). Cells were lysed in SureFire lysis buffer and transferred to 384-well opaque proxiplates. Under low-light conditions, a 1:10:40 (v:v:v) dilution of AlphaScreen acceptor beads:Surefire activation buffer:Surefire reaction buffer was prepared and the plate was incubated in the dark at RT for 2 h. Then, a 1:20 (v:v) dilution of AlphaScreen donor beads/dilution was prepared and incubated in the dark at RT for another 2 h, before the fluorescence signal was measured by used of a Fusion-α plate reader (PerkinElmer Life and Analytical Sciences) with standard AlphaScreen settings. Receptor mediated phosphorylation of Akt1/2/3 (Ser473) and Akt1 (Thr308) were determined using the AlphaScreen™ ERK1/2 SureFire™ kit, as per as per manufacturer's instructions. Data were normalized to the maximal response elicited by 10% (v:v) FBS at the same time point.

cAMP Accumulation: CHO-hFPR1, -hFPR2 and -hFPR3 stable transfected cells were plated into 96-well plates and cultured overnight at 37° C. in 5% CO$_2$. Cells were washed with PBS, and cultured overnight. Thirty minutes before assaying, the culture medium was replaced with stimulation buffer [1.4 M NaCl, 50 mM KCl, 8 mM MgSO$_4$, 2 mM Na$_2$HPO$_4$, 4.4 mM KH$_2$PO$_4$, 0.1% (w/v) BSA, 5 mM HEPES, 1.3 mM CaCl$_2$, 5.6 mM glucose)] and 10 mM rolipram (selective phosphodiesterase-4 inhibitor), and treated with forskolin (3 μM), and incubated for 30 min at 37° C. in 5% CO$_2$ Medium was aspirated and cAMP was ethanol extracted (100% ice-cold) and dried. Cells were lysed in detection buffer (dH2O, 0.3% Tween 20, 5 mM HEPES, 0.1% BSA). Lysates were transferred to a 384-well plate and mixtures of detection buffer/donor bead-conjugated anti-cAMP antibody and detection buffer: biotinylated cAMP: acceptor bead-conjugated streptavidin were added to the lysates according to the PerkinElmer cAMP Alphascreen protocol. Under low-light conditions, a 1:50 (v:v) dilution of AlphaScreen acceptor beads: stimulation buffer was prepared, 1:150 (v:v) dilution of donor beads and 50 nM biotinylated cAMP in detection buffer was prepared in a 384-well opaque optiplates. Plates were incubated in the dark at room temperature overnight before the fluorescence signal was measured by use of a Fusion-α plate reader (PerkinElmer Life and Analytical Sciences). Data were normalized to the response elicited by 10 μM forskolin at the same time point.

Data analysis: All data were analysed using GraphPad Prism 6.0 (GraphPad Software, San Deigo, Calif., USA). Where appropriate, concentration-response curves were fitted to derive the maximal agonist effect ($E_{max}$), and the ligand potency estimate ($pEC_{50}$), where $E_{max}$ is the maximal possible response of the system (not the agonist), basal is the basal level of response in the absence of agonist, and $pEC_{50}$ is the negative logarithm of the agonist concentration that gives a response halfway between $E_{max}$ and basal.

To quantify biased agonism mediated by each agonist across the various pathways ([$Ca^{2+}$], mobilization, pERK1/2, Akt1/2/3 and inhibition of cAMP accumulation), agonist concentration-response curves were refitted using the operation model normalized to the transduction ratio of a reference agonist (in this case, BIDI-002) as described previously (Stewart G D et al., 2009). Under these conditions, if the test agonist and the reference agonist activate the two pathways through a common receptor conformation, the log [bias factor] should be 0.0 (or bias factor different from 1.0), irrespective of differences in response amplification between pathways. In contrast, significant deviation of log [bias factor] from 0.0 (or bias factor different from 1.0) indicates the involvement of distinct conformations for the different agonists. All affinities, potencies, efficacies, and cooperativity parameters were estimated as logarithms (Christopoulos, 1998). Results are expressed as means±S.E. unless otherwise stated. Statistical analyses were by Student's t test, or one-way ANOVA followed by Dunnett's Comparison or Tukey's post-hoc test, as appropriate. Values of $p<0.05$ were considered statistically significant.

Results

Figure 1:
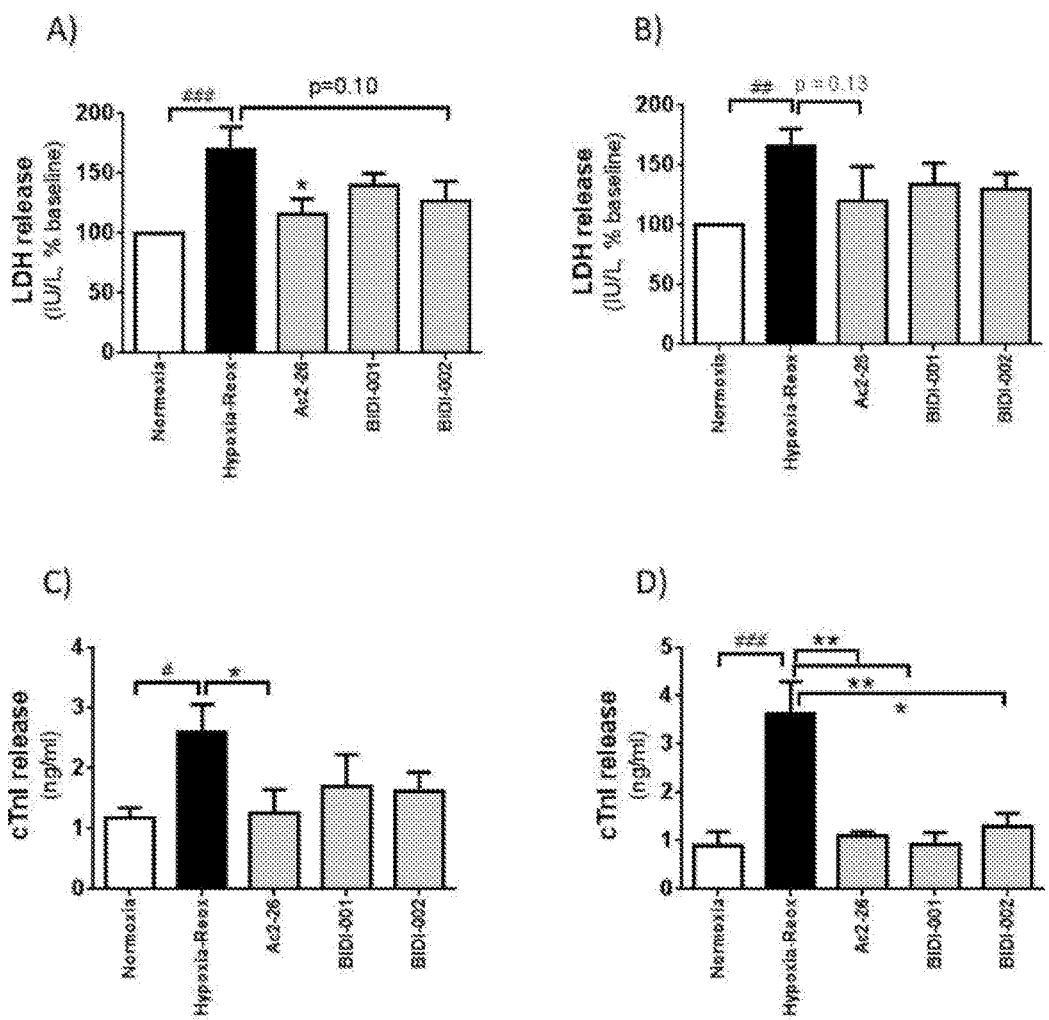
FIG. 1 is a graphical representation of the effect of Annexin-A1 mimetics on LDH (A, B) and cTnI (C,D) release on neonatal cardiomyocytes subjected to hypoxia-reoxygenation. Cardiomyocytes were subjected to 6 h hypoxia followed by 48 h reoxygenation. Treatments Annexin-A1 N-terminal peptide $Ac_{2-26}$ (1 µM) and small molecule mimetics (BIDI-001 and BIDI-002, 1 µM) were present for the full duration of hypoxia and reoxygenation (A, C) or only during reperfusion (B,D).

FPR agonists prevents hypoxia-induced cardiomyocyte injury: Hypoxia-reoxygenation significantly increased release of LDH by approximately 70%, and cTnI (a more sensitive measure of cardiomyocyte death) was almost tripled, compared to control normoxic cardiomyocytes. Cardiomyocyte LDH and cTnI release were significantly reduced when $Ac_{2-26}$ were present from 5 min prior to, and for the duration of, hypoxia-reoxygenation (1 µM, FIG. 1A, C). When present only during reoxygenation, $Ac_{2-26}$ also significantly attenuated the increase in cTnI levels, with a similar but non-significant trend in LDH (FIG. 1 B, D respectively, both p=0.13).

Similar to $Ac_{2-26}$, small molecule mimetics BIDI-001 and BIDI-002 significantly reduced cTnI, when present during reperfusion (FIG. 1D). The cTn and LDH levels in cardiomyocytes treated with small molecules were no longer different from the normoxia cells (FIG. 1A, B, C).

BIDI-001 and BIDI-002 activates hFPR receptors: To assess the functional properties of FPR agonists (fMLP, BIDI-001, and BIDI-002) in transfected CHO cells, we used a CHO cell line stable expressing the hFPR1, hFPR2, and hFPR3 and monitored intracellular $Ca^{2+}$ mobilization (FIG. 2), phosphorylation of EKR1/2 (FIG. 3), phosphorylation of Akt1/2/3 (FIG. 4) and inhibition of forskolin-stimulated cAMP accumulation (FIG. 5). None of the agonists mediated responses in CHO cells stably expressing hFPR3 (data not shown), suggesting that CHO cells have minimal basal hFPR expression.

Figure 4:
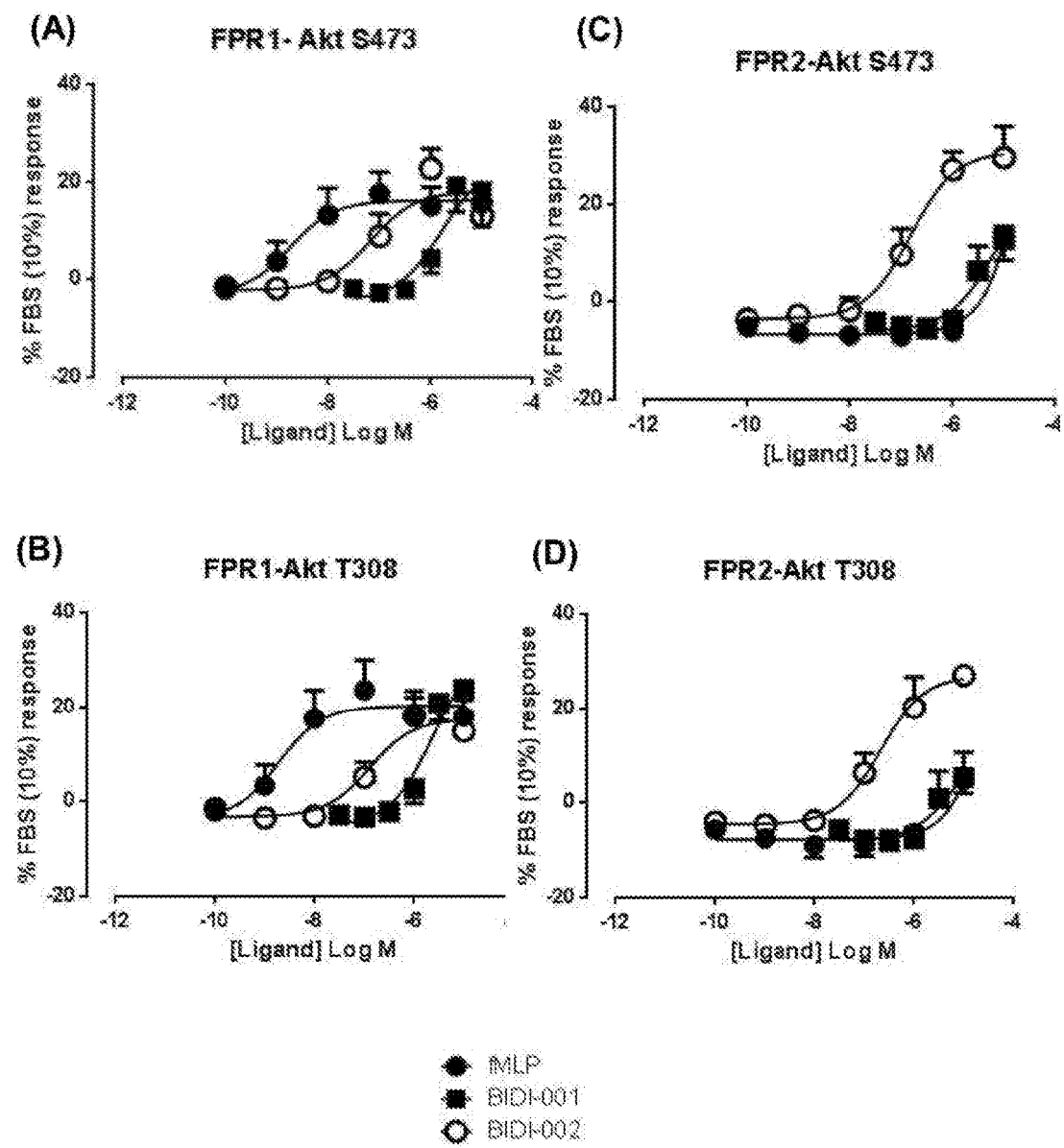
FIG. 4 is a graphical representation of the effect of agonist stimulation (fMLP, BIDI-001 and BIDI-002) on FPR-mediated pAkt 1/2/3 (Ser473) and pAkt 1 (Thr 308) in Flpln-CHO cells stably expressing the human FPR1 (A, B) or FPR2 (C,D) receptors. Data points represent a percentage of the mean±SEM of Akt phosphorylation elicited by 10% FBS±SEM collected from 4-6 experiments performed in triplicate.

Since fMLP was known to induce $Ca^{2+}$ flux through two GPCRs, the high affinity FPR1 and the low affinity FPR2, we tested the effect of BIDI-001 and BIDI-002 with overexpressed hFPR expression in CHO cells. Agonist fMLP induced a concentration-dependent $Ca^{2+}$ mobilization in hFPR1-CHO cells with a pEC in the nanomolar range, and in hFPR2-CHO cells with a $pEC_{50}$ in the micromolar range (Table 1). These results confirmed previous reports that hFPR is a high affinity for fMLP, whereas hFPR2 has a much lower affinity for fMLP (Prossnitz, E. R. and R. D. Ye 1997; Le Y. Y. et al., 1999). fMLP also had similar preferential activation for hFPR1 over hFPR2 in mediating phosphorylation of ERK (FIG. 3, Table 2) and Akt (FIG. 4, Table 3).

BIDI-001 mediated concentration dependent $Ca^{2+}$ mobilization (FIG. 2), and phosphorylation of both ERK1/2 (FIG. 3, Table 2) and Akt1/2/3 (FIG. 4, Table 3) in both hFPR1 and hFPR2 cells. Further, BIDI-001 was more effective in activating hFPR1 compared to hFPR2, by ~3 fold in the micromolar range. In contrast, BIDI-002 mediated concentration dependent responses in both hFPR1 and hFPR2 cells with similar potency (~100 µM) for $Ca^{2+}$ mobilization (FIG. 2), phosphorylation of ERK (FIG. 3, Table 2) and Akt (FIG. 4, Table 3).

Signalling through the cAMP pathway was also determined. FIG. 5A illustrated the concentration-response profile of hFPR agonists at inhibiting cAMP accumulation at the hFPR1 and hFPR2 respectively. No agonist was able to cause complete inhibition of the forskolin-stimulated responses; all effects were less than 50% maximal inhibition. Interestingly, the inhibition of forskolin-stimulated cAMP accumulation in hFPR1 by fMLP and BIDI-002 occurring at low agonist concentration is reversed at higher concentrations, yielding distinctly bell-shaped curves. The data could be fitted to an empirical model that allowed for the determination of agonist potency for the inhibitory phase. BIDI-001, on the other hand, caused cAMP accumulation in a concentration dependent manner at hFPR1. In addition, fMLP, BIDI-001 and BIDI-002 caused an inhibition of the cAMP response over the concentration range tested at the hFPR2. Table 4 summarizes the maximal responses ranges of three FPR agonists in stimulating inhibiting forskolin-stimulated cAMP, as a percentage to forskolin. Overall, BIDI-002 more potent in stimulating hFPR receptors compare to BIDI-001 with limited selectivity towards hFPR subtype.

BIDI-001 is a biased agonist: To assess the potential for our ligands to display biased agonism, the results from [$Ca^{2+}$], mobilization, ERK1/2 phosphorylation, Akt1/2/3 phosphorylation and cAMP accumulation were replotted in the form of a bias plot (FIG. 6) relative to BIDI-002, which shows the least coupling to [$Ca^{2+}$], mobilization. BIDI-001 is biased away from [$Ca^{2+}$], mobilization, indicating that it may be able to engender a different conformation of hFPR1 and hFPR2. Application of an operational model of agonism to the data allowed the quantification of the degrees of the bias relative to the preference of BIDI-002, where it was found that BIDI-002 had an approximately 20-fold preference to Akt phosphorylation, ERK phosphorylation and cAMP accumulation. These findings represent the largest degree of biased agonism thus far identified at hFPR receptors.

Example 2

In Vivo Analysis

Materials and Methods

Animals and surgery: All animal research was conducted in accordance with the National Health and Medical Research of Australian guidelines, and approval was obtained from the Alfred Medical Research of Education Precinct (AMREP) Animal Ethics Committee.

Male C57BL/6 mice were breed and housed in the AMREP Animal Centre and maintained under a 12 h light/dark cycle. After anaesthesia (i.p., ketamine 80 mg/kg, xylazine 20 mg/kg and atropine 1.2 mg/kg), mice were randomly assigned to 24 h, 48 h and 7 days reperfusion groups and underwent reversible left arterial descending (LAD) ligation as described (Gao XM, 2011; JMCC, 50; Gao XM, 2000, JMCC). Following sedation, mice were intubated and ventilated (Harvard apparatus, MA, USA) with room air mixed with oxygen (tidal volume 0.25 mL, 150 breath/min), and placed on a heating pad. A left thoractomy will be made via the ~third intercostal space, where the beating heart was located.

The LAD was reversibly ligated using 7-0 silk suture with a slipknot enclosing two releasing rings. Regional ischaemia was confirmed by pale colour of the ligated area. Air was then evacuated from the chest, the cavity was closed and normal respiration was restored. After 40-60 min of ischaemia, blood flow through the left coronary artery was re-established by releasing the slipknot. Sham-operated mice underwent identical surgical procedures except the coronary arteries were not ligated. Three cohorts of mice were scheduled. Cohort 1 was subjected to 40 min ischaemic-24 h reperfusion for the assessment of cardiac necrosis. Cohort 2 was subjected to 60 min occlusion with 48 h reperfusion for the quantification of cardiac and systemic inflammation. The last cohort was subjected to 7 d reperfusion and early cardiac fibrosis was assessed.

Treatment with study drugs: Animals were randomly assigned to different groups and all treatments were administrated 5 min prior to reperfusion of the LAD. The peptide $Ac_{2-26}$ (1 mg kg$^{-1}$) (Chemieliva, Chongqing, China) and its vehicle (10% dimethyl sulfoxide (DMSO) in saline) were intravenously (i.v.) injected via the tail vein. FPR agonists BIDI-001 (50 mg kg$^{-1}$, n=10) and BIDI-002 (50 mg kg$^{-1}$, n=7) both synthesized by Anthem Bioscience (Bangalore, India) and their vehicle control (10% DMSO containing 0.8% Tween 20 in saline) were administrated as a suspension via i.p. injection. Pilot studies indicated that 50 mg kg$^{-1}$ i.p. resulted in plasma concentrations of both compounds in the micromolar range for ~8 h after a single dose (unpublished observation). Mice then received drug or vehicle injections daily until the experimental endpoint. The two different vehicles groups reflect different study drug solubility and administration routes.

Sample collection: After the study period (24 h, 48 h or 7 d), infarcted or sham-operated mice were euthanised, blood was collected by cardiac puncture using a 25G needle and 1 mL syringe coated with heparin (500 U/mL). Plasma was collected from mice after 24 h reperfusion to assess levels of cardiac troponin I (cTnI) levels; whole blood was collected from mice after 48 h reperfusion to assess total and differential white blood cell (WBC) numbers in the circulation. Lungs, atria, left and right ventricles were dissected, blotted dry, and weighed. Left ventricles (LV) were cut in half at the occlusion site, with the upper part fixed in Neutral Buffer Formalin (NBF, Thermo Fisher Scientific, Melbourne, Australia) and the apex placed in Tissue-Tek® optimal cutting temperature (OCT) compound (Tissue-Tek, Torrance, USA) for storage at −80° C.

Assessment of cardiac necrosis: The optimal time point for assessment of cardiac necrosis is 24 h reperfusion after an ischaemic insult. Plasma levels of cTnI were determined using a commercially available, high-sensitivity rat cTnI ELISA kit (Life Diagnostic Inc., Pennsylvania, USA) as per the manufacturer's instructions. To evaluate the size of the infarction in relation to the area-at-risk (AAR), infarct size (IS) and LV size, 2,3,5-triphenyltetrazolium chloride (TTC) staining was performed. The LAD was tightly re-occluded in anaesthetised mice after 24 h of reperfusion and Evans blue dye (0.1 mL, 5%) was injected as a bolus into the LV. The heart was then excised and rinsed in cold saline to remove excess dye. The LV was isolated, frozen at −20° C. and then cut transversely into six to seven slices at 1.0 mm thickness. LV slices were incubated for 45 min with 1.5% TTC solution at 37° C. The presence of Evans blue indicated perfusion, whereas its absence indicated lack of perfusion to that region, whereas the brick red areas indicate viable myocardium, white or yellowish regions demarcate necrotic tissue. The slices were mounted between glass slides, and images were acquired digitally using Olympus microscope (Leica Wild M3B, Heerbrugg, Switzerland) coupled with digital camera (Nikon Cool-PIX4500, Tokyo, Japan). The images were analyzed using Image J analysis program (Version 1.45S, National Institute of Health, USA). The non-ischaemic zone (blue area), area-at-risk zone (AAR, red and white or yellow areas), infarct zone (white or yellow areas) and total LV were outlined and quantified blindly. Infarct size was calculated as percentage of infarct zone/risk zone.

Assessment of cardiac inflammation: LV tissue embedded in OCT compound following 60 min ischaemia and 48 h reperfusion were sectioned at 6 μm for immunofluorescent analysis. Sections were pre-incubated with 4% paraformaidehyde for 20 min and 10% normal goat serum for a further 30 min. Sections were then incubated at room temperature (RT) with either CD68+ primary antibody or Ly-6B.2 primary antibody (1:200, ABD Serotec, Raleigh, USA) for 1 h, followed 30 min incubation with the Alexa Fluor 546 secondary antibody (1:200, Invitrogen, Carlsbad, USA), to detect cardiac macrophage and neutrophil infiltration, respectively. Finally, sections were incubated with 0.001% Hoechst 33342 (Invitrogen, Melbourne, Australia) for 30 min, to elicit nuclear staining. Single images were photographed using a Nikon A1R confocal microscope (Nikon Instruments Inc., NY, USA) under 20× magnification, and 9×9 single images were then automatically stitched together using NIS-Elements AR software (version 4.10 for Windows, Nikon Instruments Inc., NY, USA) to form each whole LV section. The images for infarct area were captured under 40× magnification, and the stitched images were then analysed using Fiji software (version 1.48c for Max OS X, National Institutes of Health, USA). The threshold was set for each image, to enable optimal sensing of red fluorescence intensity above threshold, and the software then automatically quantified these red fluorescent signals.

Assessment of systemic inflammation: Blood samples collected from mice subjected to 60 min ischaemia and 48 h reperfusion were diluted 1:20 into 2% acetic acid to lyse the red blood cells for total WBC counting, using a haemocytometer. Blood smears were stained using a hemacolor staining kit (Merck millipore, Melbourne, Australia) and then examined under 60× magnification using an Olympus Biological CHS microscope (Olympus Inc., Tokyo, Japan) for manual counting of neutrophils, lymphocytes and monocytes per 100 WBCs.

Assessment of cardiac histology and fibrosis: LV hearts fixed in NBF after 40 min ischaemia and 7 d reperfusion were embedded in paraffin by the Alfred Pathology Service (Melbourne, Australia) and sectioned at 4 μm with a Leica 2135 microtome (Leica Microsystems, Wetzlar, Germany). Sections were stained with haematoxylin and eosin (H&E) for assessment of myocardial morphology, or picrosirius red (0.1%, Fluka, Bucks, Switzerland; pH2) for cardiac collagen deposition. Images were taken at 1.25× to capture the whole LV. To examine the local infarct area, images were collected at 20× using the microscope (Olympus BX61, Olympus Inc., Ontario, Canada) and QCapture Pro software (version 5.1 for Windows, Media Cybernetic Inc., Maryland, USA). H&E images were scored blindly in random order on a scale of 1 to 5, based on intensity of blue staining of nuclei (1=least, 5=most, classified by independent observer). The area of picrosirius red staining (% LV area) was quantitatively measured using Image-Pro Plus software (Media Cybernetic Inc., Maryland, USA) for sets of LV slides from 48 h reperfusion and 7 d reperfusion study.

Statistical analysis: Graph construction and statistical analysis were performed using Graphpad Prism 6 software (Graphpad Prism Software Inc, La Jolla, USA). Data are presented as the mean±standard error of the mean (SEM). One-way Analysis of Variance (ANOVA) with Tukey post-hoc analysis was performed where n>3, and p<0.05 was considered statistically significant.

Results

Systemic and cardiac characteristics following I-R Injury: The extend of cardiac injury was assayed at 24 h, 48 h and 7 d after initiation of reperfusion, systemic characteristics were only recorded in the 48 h and 7 d reperfusion mouse cohorts.

Body and organ weights were measured to examine effects of drug treatments on systemic and cardiac characteristics in mice subjected to myocardial ischaemia-reperfusion injury or sham operation. Although there was no difference between the two vehicles (10% DMSO) in saline i.v. vs. 10% DMSO containing 0.8% Tween 20 in saline, i.p.), data from these two groups were combined for group analysis. As shown in Table 1, 48 h of reperfusion following an ischaemic insult to the heart, there were no differences in body, atria or lung weights, but heart weight were significantly increased in vehicle, $Ac_{2-26}$ and BIDI-001 treated hearts, when normalized to body weight.

Similar but non-significant trends for infarcted hearts: body weight ratio were evident after 7 d reperfusion with vehicle (p=0.07) compare to sham, but no longer evident in $Ac_{2-26}$-treated hearts (p=0.97). Interestingly, administration of BIDI-001, but not $Ac_{2-26}$ or BIDI-002 significantly reduced both total heart weight, and LV weight, normalized to body weight, consistent with protective actions of BIDI-001 on cardiac modelling post I-R injury.

$Ac_{2-26}$ and BIDI-001 Significantly Reduce Plasma Cardiac Necrosis: Occlusion of the LAD and subsequent reperfusion produced a marked damage in the mouse LV that was reliably measured at the 24 h time point. Approximately 60% of the LV stained by Evans blue underlying the area-at-risk (AAR, FIG. 7B), 30%-40% of this portion of the ventricle was infarcted (FIG. 7C). Administration of peptide $Ac_{2-26}$ immediately before LAD reperfusion significantly attenuated infarct size by ~25%. Interestingly, the small molecule mimetic BIDI-001 reduced infarct size by ~34%, (but not BIDI-002, FIG. 7C). Plasma cTnI level is a selective marker of cardiomyocyte injury. Plasma cTnI levels were significantly increased following 24 h reperfusion compared to sham (FIG. 7D). Although cTnI levels remained significantly increased in $Ac_{2-26}$ treated mice compared to sham following I-R injury, a non-significant trend for $Ac_{2-26}$ to lower cTnI levels relative to vehicle-treated I-R injured mice was evident (p=0.10, FIG. 7D). Excitingly, the small molecule mimetic BIDI-001 significantly reduced cTnI in plasma (not seen with BIDI-002).

Figure 8:
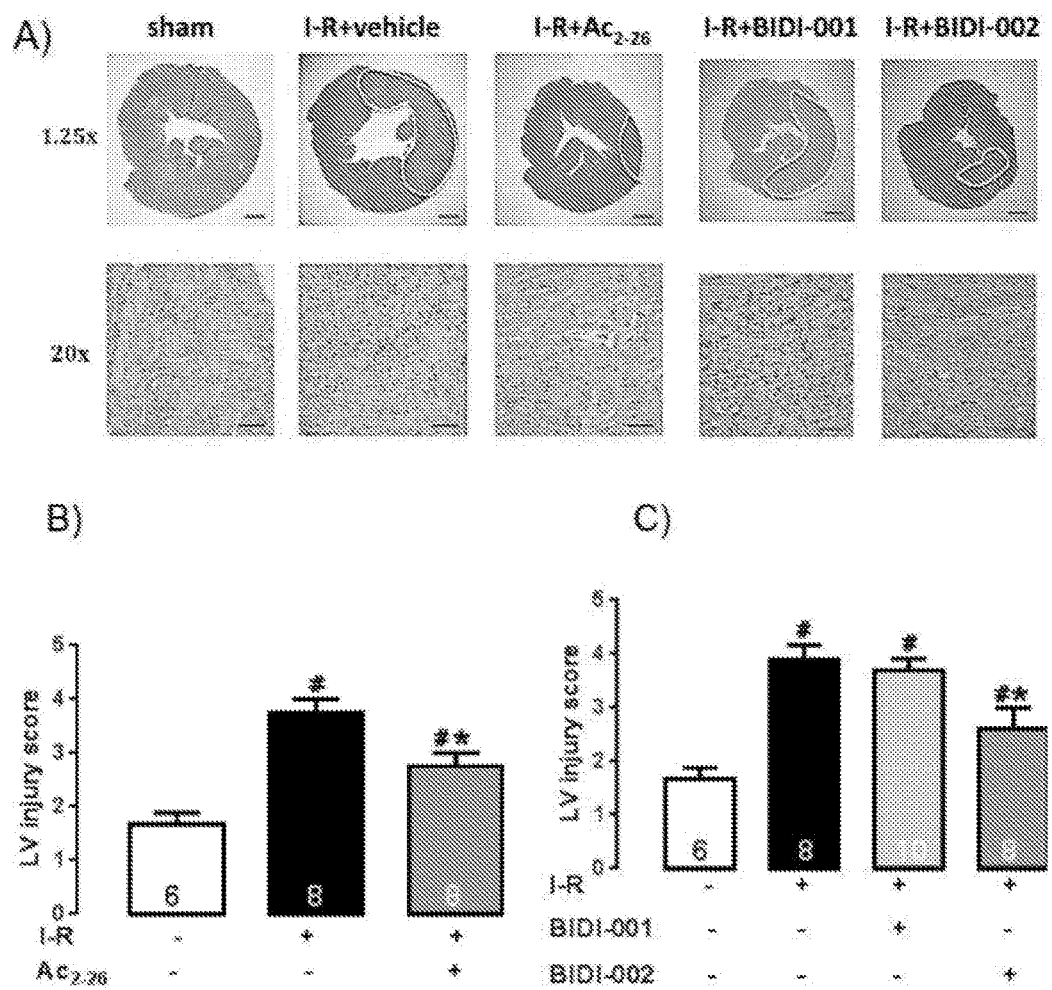
FIG. 8 is an image depicting the effect of peptide and small molecule ANX-A1 mimetics on I-R-induced changes in left ventricular morphology 48 h post I-R. A) Representative H&E stained section of LV from sham mice, vehicle treated, $A_{c2-26}$ or vehicle and small molecule mimetics (BIDI-001, BIDI-002)-treated mice 48 h post I-R. B) Pool data of histological injury scores on H&E staining. #$P<0.05$ versus sham, *$P<0.05$ versus vehicle treated mice. One-way ANOVA with Tukey post-hoc test. Data were represented as mean±SEM.

$Ac_{2-26}$ and BIDI-001 Attenuate Cardiac Inflammation:

The effect of myocardial I-R and treatments on cardiac inflammation after 60 min ischaemic-48 h reperfusion was firstly established by scoring of the H&E staining. Myocardial I-R groups exhibited an H&E injury score in a localized area of LV viewed under low power (1.25×) in all groups compared to sham, regardless of treatment. This was consistent with cell infiltration in this region, as observed at higher magnification (20×, FIG. 8A). Semi-quantitative analysis revealed that LV injury scores were clearly increased in vehicle-treated I-R mice compared to sham; this increase was significantly inhibited by $Ac_{2-26}$ treatment, although LV injury was still greater in $Ac_{2-26}$-treated mice relative to shams (FIG. 8B). Similarly, semi-quantitative analysis also suggested that LV injury scores in vehicle, BIDI-001 and BIDI-002-treated I-R mice were significantly increased (FIG. 8C). BIDI-002 (but not BIDI-001) significantly attenuated cell infiltration compared to vehicle-treated I-R mice (FIG. 8C).

Figure 9:
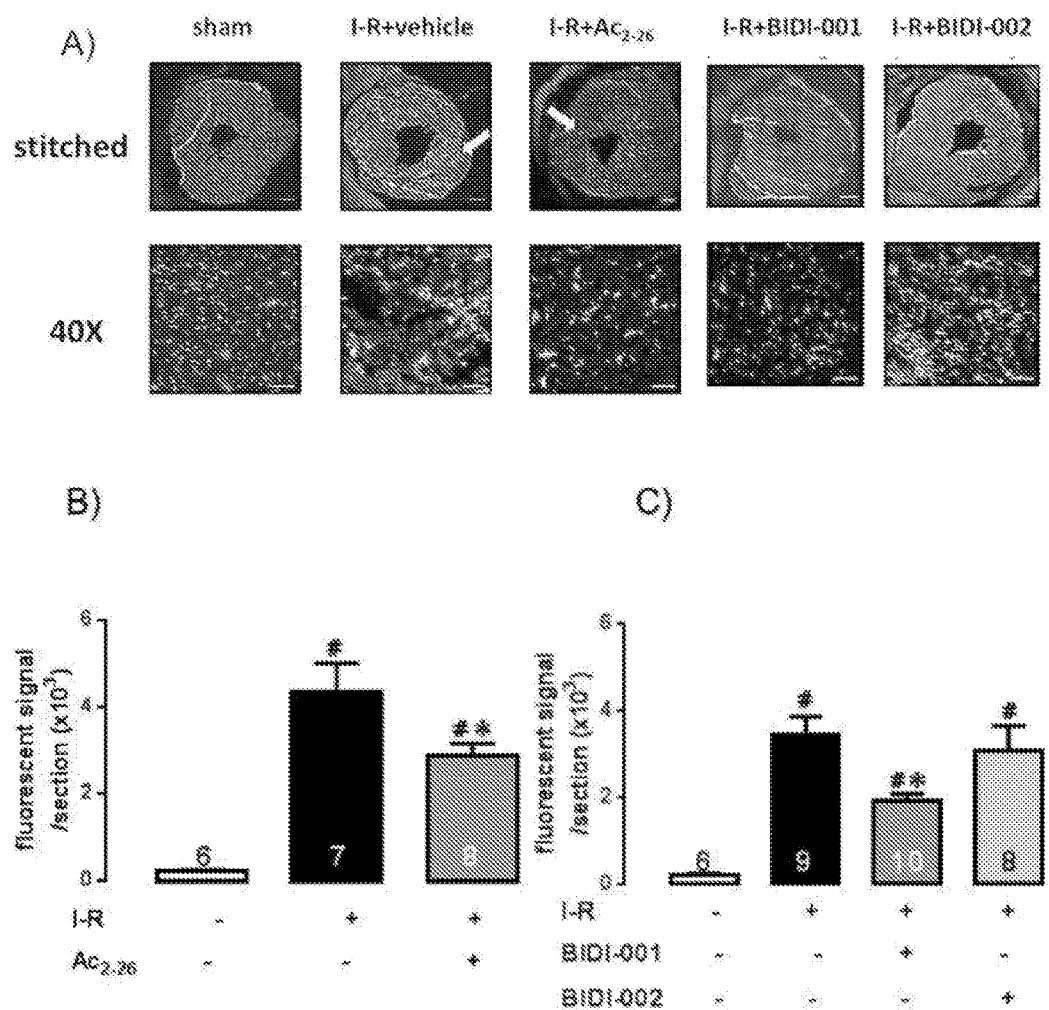
FIG. 9 is an image depicting the effect of peptide mimetic and small molecule ANX-A1 mimetics on I-R-induced neutrophil infiltration in the LV 48 h post I-R injury. A) Representative stained sections of LV from sham, peptide $Ac_{2-26}$ and small molecule non-peptide mimetics (BIDI-001 and BIDI-002). Scale bar 500 µm for 20× (stitched from 9×9 single images photographed under 20× magnification) and 100 µm for 40×. B) Pooled data of Ly-6B.2 signal detection. #$P<0.05$ versus sham, *$P<0.05$ versus vehicle treated mice. One-way ANOVA with Tukey post-hoc test. Data were represented as mean±SEM.

To further investigate the nature of cardiac cell infiltration post I-R injury, detection of macrophages and neutrophils was performed. Immunofluorescent detection of neutrophils in LV sections revealed a significant increase in mice subjected to I-R compared to sham, under both 20× and 40× magnification (FIG. 9), using an antibody to Ly-6B.2. I-R injury elicited significant increased in neutrophil signals per section in both vehicle- and $Ac_{2-26}$-treated I-R mice compared to sham (FIG. 9B). Administration of $Ac_{2-26}$ reduced neutrophil numbers by approximately 35% compared to saline-treated I-R (FIG. 9B). Ly-6B.2 signal detection per LV section was also significantly increased across vehicle-treated I-R mice compared to sham (FIG. 9C). BIDI-001 (but not BIDI-002) significantly attenuated the Ly-6B.2 neutrophil signal by almost half (FIG. 9C).

Figure 10:
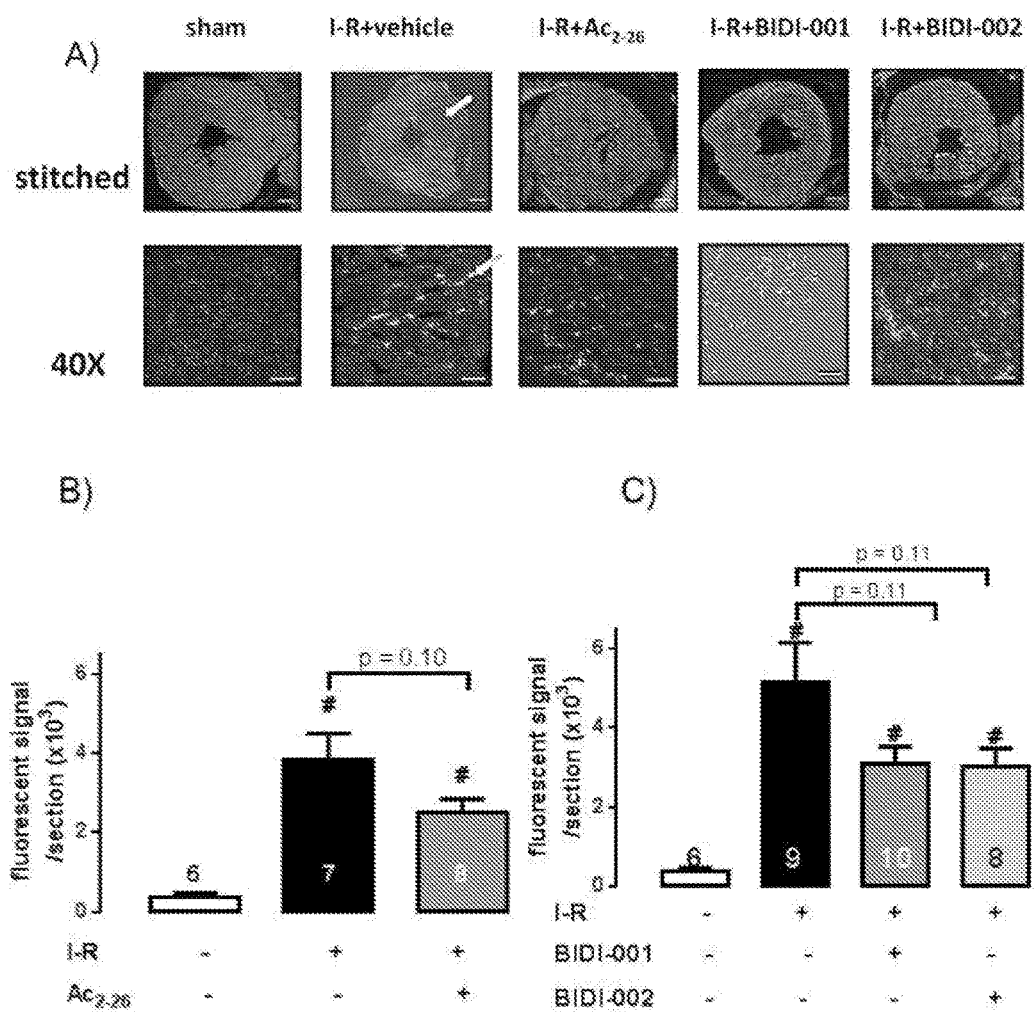
FIG. 10 is an image depicting the effect of peptide and small molecule ANX-A1 mimetics on I-R-induced macrophage infiltration in the LV 48 h post I-R injury. A) Representative stained sections of LV from sham, peptide $Ac_{2-26}$ and small molecule non-peptide mimetics (BIDI-001 and BIDI-002). Scale bar 500 µm for 20× (stitched from 9×9 single images photographed under 20× magnification) and 100 µm for 40×. B) Pooled data of $CB68^+$ signal detection. #$P<0.05$ versus sham, *$P<0.05$ versus vehicle treated mice. One-way ANOVA with Tukey post-hoc test. Data were represented as mean±SEM.

Macrophage numbers in LV sections were also increased in all treatment groups after 60 min ischaemia-48 h reperfusion compared to sham in both vehicle-treated and ANA-A1 mimetic-treated mice (FIG. 10). CD68+ detection of macrophage by immunofluorescence suggested that the amount of signal per LV section was significantly increased in vehicle- and $Ac_{2-26}$-treated I-R mice compared to sham, a non-significant trend (p=0.10) for the reduction of macrophage signal was observed in $Ac_{2-26}$-treated I-R mice compared to vehicle-treated I-R mice (FIG. 10B). As shown in FIG. 10C, a significant increase in CD68+ signal observed in vehicle-treated mice compared to sham, which tended to be reduced by both BIDI-001 (p=0.11) and BIDI-002 (p=0.11, FIG. 10C).

Figure 11:
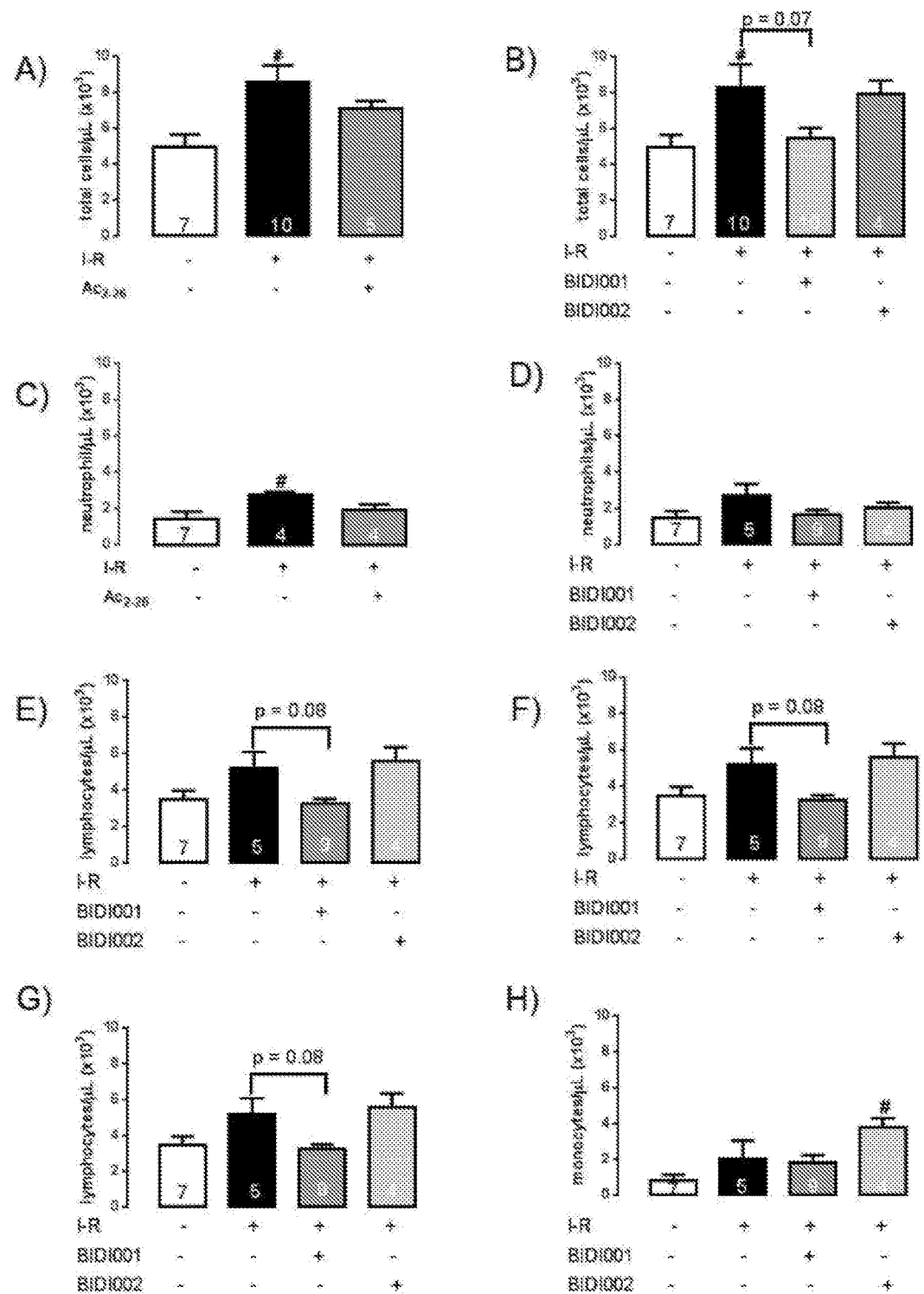
FIG. 11 is a graphical representation of the effect of peptide and small molecule ANX-A1 mimetics on I-R-induced changes in circulatory leukocytes 48 h post I-R injury. Pooled data of A) Total WBS, B) Neutrophil, C) Lymphocytes and D) Monocyte in blood collected from sham, peptide $Ac_{2-26}$ and small molecule non-peptide mimetics (BIDI-001 and BIDI-002). #$P<0.05$ versus sham, *$P<0.05$ versus vehicle treated mice. One-way ANOVA with Tukey post-hoc test. Data were represented as mean±SEM.

$Ac_{2-26}$ and BIDI-001 tend to reduce systemic inflammation: Total and differential WBC quantification was performed to investigate the effects of Anx-A1 mimetics on systemic inflammation (FIG. 11). The number of total circulating WBCs, and differential WBC numbers of neutrophils, lymphocytes and monocytes were significantly increased in vehicle-treated I-R mice compared to sham; but this was not seen in $Ac_{2-26}$-treated I-R mice (FIG. 11A, C, E, G). $Ac_{2-26}$-treated mice did not significantly alter the total and differential WBC numbers. BIDI-001 tended to reduce the WBC (p=0.07) and lymphocyte numbers (p=0.08) (FIG. 11B, F), whereas BIDI-002 significantly increased the level of monocytes (FIG. 11H).

Figure 12:
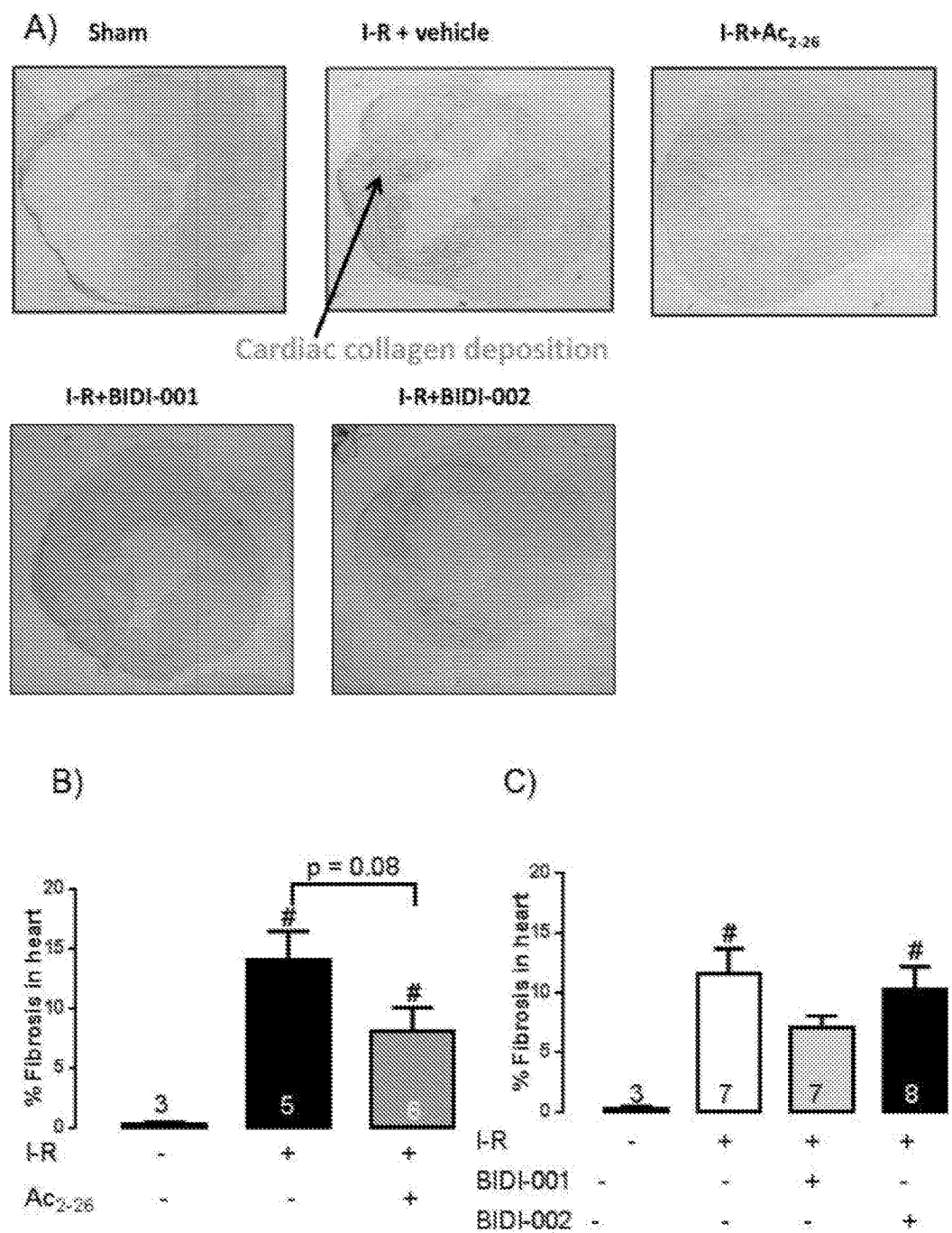
FIG. 12 is an image depicting the effect of peptide and small molecule ANX-A1 mimetics on I-R-induced changes in cardiac fibrosis after 7 days post I-R injury. A) Representative stained cross-sections of infarcted LV stained with picrosirius red in sham, peptide mimetic $Ac_{2-26}$ and small molecule non-peptide mimetics (BIDI-001 and BIDI-002). B) Pooled data of cardiac fibrosis in different treatment groups. #$P<0.05$ versus sham, *$P<0.05$ versus vehicle treated mice. One-way ANOVA with Tukey post-hoc test. Data were represented as mean±SEM.

$Ac_{2-26}$ and BIDI-001 attenuate cardiac fibrosis: Picrosirius red staining was performed for LV sections from both the 48 h reperfusion study and the 7 d reperfusion study, to detect collagen deposition. Reperfusion of 48 h did not induce any evident increase in picrosirius red staining in a localized area of the LV sections viewed under low power (1.25×) in saline- and $Ac_{2-26}$-treated mice (data not shown), while 7d reperfusion caused an obvious increase of stained area in all mice subjected to myocardial I-R injury (FIG. 12B). Quantitative analysis revealed that the area of red staining (% LV area) clearly increased in vehicle-treated I-R mice compared to sham; this increase tended to be inhibited by $Ac_{2-26}$ treatment, but in a non-significant manner (p=0.08, FIG. 12C). Similarly, the I-R-induced increase in cardiac fibrosis persist in vehicle- and BIDI-002-treated mice, but was absent in BIDI-001 treated mice.

Example 3

Further In Vivo Analysis

Animals: All animal research was conducted in accordance with the National Health and Medical Research of Australian guidelines, and the approval was obtained from the Alfred Medical Research Education Precinct (AMREP) Animal Ethics Committee. Neonatal (1-2 day old) Sprague-Dawley rats (mixed sex) and adult male C57BL/6 mice were bred and housed in the AMREP Animal Centre and maintained under a 12 h light/dark cycle. All reagents were purchased from Sigma-Aldrich (St. Louis, USA) except where indicated, and were of analytic grade or higher.

Animal Surgery: Adult C57BL/6 mice were randomly assigned to myocardial ischemia-reperfusion (I-R) injury or sham in vivo. Anesthetized mice (ketamine 80 mg/kg, xylazine 20 mg/kg and atropine 1.2 mg/kg, KXA, i.p.) underwent reversible left arterial descending (LAD) ligation as described (Gao et al. 2000 & Gao et al. 2011). Following sedation, mice were intubated and ventilated (Harvard apparatus, MA, USA) with room air mixed with oxygen (tidal volume 0.25 mL, 150 breaths/min), and placed on a heating pad. A left thoracotomy was be made around the third intercostal space, where the beating heart was located. The LAD was reversibly ligated using 7-0 silk suture with a slipknot enclosing two releasing rings. Regional ischemia was confirmed by pale color of the ligated area. Air was then evacuated from the chest, the cavity closed and normal respiration restored. Blood flow through the left coronary artery was subsequently re-established at the end of the ischemic period (i.e. reperfusion) by releasing the slipknot. Three distinct cohorts of mice were studied. Cohorts 1 and 2 were subjected to 40 mins ischemia with either 24 h or 7 days reperfusion, optimal timepoints for the assessment of cardiac necrosis and early cardiac remodeling in vivo, respectively. Cohort 3 was subjected to 60 mins LAD occlusion with 48 h reperfusion, for the quantification of cardiac and systemic inflammation. Sham-operated mice underwent identical surgical procedures except the LAD was not ligated. Mice were randomly assigned to administration of FPR agonists, either Cmpd17b or Cmpd43 (both 50 mg/kg/day i.p., both synthesized by Anthem Bioscience, Bangalore, India) (3,4), or equivalent volume of vehicle control (10% DMSO containing 0.8% Tween-20 in saline i.p.) immediately prior to reperfusion. FPR-agonist doses in vivo were chosen based on that previously shown for Cmpd43 to reduce ear inflammation (Cilibrizzi et al. 2009 & Burli et al. 2006), with pilot studies suggesting plasma concentrations in the high submicromolar-low micromolar range for both compounds for several hours post dose. Chemical structures and molecular weights of BIDI-001 and BIDI-002 are depicted in FIG. 21A. All other materials were purchased from Sigma-Aldrich (St. Louis, USA) except where indicated, and were of analytic grade or higher. For all three cohorts, infarcted or sham-operated mice were euthanized under KXA anesthesia at study end, and heparinized blood collected by cardiac puncture.

Assessment of cardiac necrosis in vivo: The optimal time point for assessment of cardiac necrosis is 24 h reperfusion after an ischemic insult. Plasma levels of cardiac troponin I (cTnI) were determined at this timepoint firstly using a commercially available, high-sensitivity mouse cTnI ELISA kit (Life Diagnostic Inc., Pennsylvania, USA) as per the manufacturer's instructions. To further evaluate the extent of cardiac necrosis, infarct size (IS) in relation to the area-at-risk (AAR) was also determined using 2,3,5-triphenyltetrazolium chloride (TTC) staining. The LAD was tightly re-occluded in anaesthetized mice after 24 h reperfusion and Evans blue dye (0.1 mL, 5%) was injected as a bolus into the LV. The heart was then excised and rinsed in cold saline to remove excess dye. The LV was isolated, frozen at −20° C. and then cut transversely into six to seven slices at 1.0 mm thickness. LV slices were incubated for 45 min with 1.5% TTC solution at 37° C. The presence of Evans blue indicated perfusion, whereas its absence indicated lack of perfusion to that region. Brick red areas indicated viable myocardium, while white or yellowish regions demarcated necrotic tissue. The slices were mounted between glass slides, and images were acquired digitally using a surgical microscope (Leica Wild M3B, Heerbrugg, Switzerland) coupled with digital camera (Nikon Cool-PIX4500, Tokyo, Japan). The images were analyzed using Image J analysis program (Version 1.45S, National Institute of Health, USA). The non-ischemic zone (blue area), AAR zone (red and white or yellow areas), infarct zone (white or yellow areas) and total LV were outlined and quantified blindly. Infarct size was calculated as percentage of infarct zone in the AAR.

Assessment of early cardiac remodeling in vivo: LV tissues collected from mice in Cohort 2, after 40 min ischemia and 7-days reperfusion (optimal time point for assessment of cardiac fibrosis and apoptosis), were fixed in NBF, embedded in paraffin by the Alfred Pathology Service (Melbourne, Australia) and sectioned at 4 μm with a Leica 2135 microtome (Leica Microsystems, Wetzlar, Germany). Sections were stained with picrosirius red (0.1%, Fluka, Bucks, Switzerland; pH 2) for assessment of cardiac collagen deposition. Images were taken at 1.25× to capture the whole LV. To examine the peri-infarct area, images were collected at 20× using the microscope (Olympus BX61, Olympus Inc., Ontario, Canada) and QCapture Pro software (version 5.1 for Windows, Media Cybernetic Inc., Maryland, USA). The area of picrosirius red staining (% LV area) was quantitatively measured using Image-Pro Plus software (Media Cybernetic Inc., Maryland, USA) for sets of LV slides from the 7-day reperfusion study. Levels of apoptosis of the infarct area were also assessed in paraffin-embedded ventricular sections, using the CardioTAC In Situ Apoptosis Detection Kit (Trevigen, Gaithersburg, Md., USA)(Huynh et al. 2012). This method detects nuclear DNA fragmentation by using a terminal deoxynucleotidyl transferase enzyme, which incorporates labeled nucleotides onto the free 3'-OH ends of DNA fragments. Positively-stained apoptotic cells were distinguished by blue staining, whilst negatively-stained cells were counterstained red with Nuclear Fast Red. Apoptotic cells were quantified as a percentage of non-apoptotic cells, and the results were expressed as fold levels detected in sham mouse heart. Plasma levels of Cmpd17b and Cmpd43 were also determined in Cohort 2 mice after 7 days reperfusion, by the Monash Centre for Drug Candidate Optimization via ultra-performance liquid chromatography with positive electrospray ionization detection approximately 20 h after the last dose.

Assessment of cardiac inflammation in vivo: Lungs, atria, left and right ventricles from mice in Cohort 3 (following 60 min ischemia and 48 h reperfusion, optimal timing for detecting cardiac leukocyte infiltration) were dissected, blotted dry, and weighed. LV were cut in half at the occlusion site, and the apical half placed in Tissue-Tek® optimal cutting temperature compound (Tissue-Tek, Torrance, USA) for storage at −80° C. LV tissues were then sectioned at 6 µm for immunofluorescent detection of cardiac macrophage and neutrophil content. Sections were pre-incubated with 4% paraformaldehyde for 20 min and 10% normal goat serum for a further 30 min. Sections were then incubated at RT with either CD68+ primary antibody or Ly-6B.2 primary antibody (1:200, ABD Serotec, Raleigh, USA) for 1 h, followed by 30 min incubation with the Alexa Fluor 546 secondary antibody (1:200, Invitrogen, Carlsbad, USA). Finally, sections were incubated with 0.001% Hoechst 33342 (Invitrogen, Melbourne, Australia) for 30 min, to elicit nuclear staining. Single images were photographed using a Nikon A1R confocal microscope (Nikon Instruments Inc., NY, USA) under 20× magnification, and 9×9 single images were then automatically stitched together using NIS-Elements AR software (version 4.10 for Windows, Nikon Instruments Inc., NY, USA) to form each complete composite LV image. The images for infarct area were captured under 40× magnification, and the stitched images were then analyzed using Fiji software (version 1.48c for Max OS X, National Institutes of Health, USA). The threshold was set for each image, to enable optimal sensing and quantification of red fluorescence intensity above threshold, and the software then automatically quantified these red fluorescent signals.

Assessment of systemic inflammation in vivo: Whole blood and plasma were also collected from mice in Cohort 3 (following 60 min ischemia and 48 h reperfusion) to assess total and differential circulating white blood cell (WBC) numbers, and plasma levels of the pro-inflammatory cytokine IL-1β. Blood samples were diluted 1:20 into 2% acetic acid, to lyse the red blood cells for total WBC counting, using a hemocytometer. Blood smears were stained using a Hemacolor staining kit (Merck Millipore, Melbourne, Australia) and then examined under 60× magnification using an Olympus Biological CHS microscope (Olympus Inc., Tokyo, Japan) for manual counting of neutrophils, lymphocytes and monocytes per 100 WBCs. Plasma IL-1β was determined using a commercially available ELISA kit (elizakit, Melbourne, Vic, Australia) as per manufacturer's instructions.

Isolation and culture of primary rat cardiomyocytes and mouse cardiac fibroblasts: All materials used for cell isolation were of tissue culture grade. Isolation of primary neonatal rat cardiac cardiomyocytes (NRCM) and adult mouse cardiac fibroblasts (AMCF) was performed by serial enzymatic digestion, as previously described (Irvine et al 2012 & Irvine et al. 3) NRCM were plated onto either 12-well tissue culture plates (for simulated ischemia-reperfusion, via hypoxia-reoxygenation, H-R) or 60 mm tissue culture dishes (for gene expression) at a density of $1.3 \times 10^5$ cells/cm$^2$, in the presence of 1% 5-bromo-2'-deoxyuridine. AMCF (passage #3) were seeded onto 60 mm tissue culture dishes at $9.5 \times 10^4$ cells/cm$^2$ and allowed to grow to 80% confluence prior to study. Following 48 h in serum-free DMEM, NRCM in 12-well tissue plates were subjected to simulated ischemia, induced by replacement of culture media with sterile-filtered Kreb's buffer (118 mM NaCl, 4.8 mM KCl, 1.2 mM KH2PO4, 1.2 mM MgSO4, 25 mM NaHCO3, 50 mM EDTA, 11.0 mM glucose, 1.75 mM CaCl2) prior to incubation for 6 h at 37° C. under hypoxia (95% N2-5% CO2, using a hypoxia chamber, QNA International, Melbourne, Australia). At the end of hypoxia, Kreb's buffer was replaced with fresh, sterile-filtered Kreb's buffer, in the presence or absence of FPR agonists Cmpd17b, Cmpd43 (both 1 µM or vehicle, and NRCM were subjected to 48 h reoxygenation at 37° C. At the end of 48 h reoxygenation, NRCM supernatant was collected for assessment of cardiomyocyte injury. Cardiomyocyte release of cTnI was determined using a commercially available, high-sensitivity rat cTnI ELISA kit (Life Diagnostic Inc.) as per the manufacturer's instructions. Separate NRVM on 60 mm dishes were incubated for 48 h at 37° C. in serum-free DMEM, in the presence or absence of FPR agonists Cmpd17b, Cmpd43 (both 1 µM) or vehicle. At the end of 48 h, RNA was extracted and real-time PCR performed (as described previously (Huynh et al. 2012)), to determine the relative gene expression of rat Fprs (rFpr1, rFpr2 and rFpr3, expressed as the threshold cycle number Ct subtracted from the maximum cycle number utilized, 40). Note that IUPHAR receptor nomenclature uses uppercase letters for human formyl peptide receptors (hence FPR1 etc) whereas title case is used for rodent receptors (hence Fpr1 etc)(Ye et al. 2009).

AMCFs were starved overnight in serum-free DMEM prior to incubation with the pro-fibrotic stimulus transforming growth factor TGF-β (10 ng/ml) for 24 h at 37° C. FPR agonists Cmpd17b, Cmpd43 (both 10 µM) or vehicle were present 30 min prior to TGF-β. At the end of 24 h stimulation, RNA was extracted and real-time PCR performed to determine the relative gene expression of CTGF and IL-1β, relative to housekeeping gene 18S, as described previously (5). Relative gene expression of mouse Fprs (mFpr1 and mFpr2, expressed as the threshold cycle number Ct subtracted from the maximum cycle number utilized, 40) was also determined at the end of 24 h stimulation.

Assessment of biased signaling at human FPRs in vitro: (i) Generation and culture of stably-transfected recombinant hFPR-CHO cells: CHO cells do not express native FPRs and are thus the ideal cells with which to stably-transfect human FPRs. In the present study, FIp-IN CHO cells and Gateway plasmid were obtained from Invitrogen Inc (Carlsbad, Calif., USA). The sequences for all 3 known human FPRs (hFPR1, hFPR2 and hFPR3) were amplified by PCR and cloned into the Gateway entry vector, pDONR202TM, using the BP clonase enzyme mix, according to the manufacturers' instructions. The hFPR pDONR201TM constructs were subsequently transfected into the pEF5/FRT/V5/dest vector using the LR clonase enzyme mix (Invitrogen). Receptor constructs (pEF5/FRT/V5/dest) were used to transfect FIp-IN CHO cells, as described previously (Valant et al. 2014). Cells were selected using 500 µg/mL hydromycin to generate cell lines stably expressing each human receptor construct. Cells were maintained and cultured in high glucose Dulbecco's modified eagle medium (DMEM) supplemented with 10% fetal bovine serum (FBS, from JRH Biosciences, Lenexa, Kans., USA) and 500 µg/mL hydromycin B (Invitrogen Inc) at 37° C. under a humidified atmosphere containing 5% CO2. Cell were plated into 96-well transparent cell culture plates at $4 \times 10^4$ cells per well, cultured overnight in serum-free media at 37° C. in 5% CO2. Concentration-response assays for each of Cmpd17b, Cmpd43 and the widely-studied FPR-subtype-selective agonists N-formyl-Met-Leu-Phe (fMLP, FPR1-selective agonist, from Sigma-Aldrich) and lipoxin-A4 (LxA4, FPR2-selective agonist, from Biomol International, Plymouth Meeting, Pa., USA) were performed for each of intracellular Ca2+ mobilization, extracellular signal regulated kinase 1 and 2 phosphorylation (pERK1/2) and Akt1/2/3 phosphorylation (both Ser473 and Thr308), as well as inhibition of cAMP accumulation.

(ii) Intracellular Ca2+ mobilization: Intracellular Ca2+ mobilization was determined in stably-transfected recombinant hFPR CHO cells, as described previously (Valant et al. 2014). Briefly, cells were washed once using HEPES buffered saline (HBS) solution [150 mM NaCl, 2.2 mM CaCl2, 2.6 mM KCl, 1.2 mM MgCl2, 10 mM HEPES, 10 mM D-Glucose, 0.5% (w(10)(10)(10):v) bovine serum albumin (BSA) and 4 mM probenecid] at pH 7.4, then treated with Fluo-4-AM (1 µM, from Invitrogen Inc, in HBS/BSA/probenecid) for 60 min at 37° C. in 5% CO2 in the dark (May et al. 2010). Cells were then further washed and placed in HBS/BSA/probenecid solution and assayed using the FLEXstation 3 plate reader (Molecular Devices, Sunnyvale, Calif.). For all experiments, the peak change in fluorescence signal was normalized to the cellular response to 100 µM ATP, which was used as an internal positive control.

(iii) Measurement of pERK1/2 phosphorylation: Surefire ERK1/2 phosphorylation kits were purchased from PerkinElmer Life and Analytical Science (Waltham, Mass., USA). Time-course experiments of ERK1/2 phosphorylation at Thr202/Tyr204 were performed to determine the time of maximal phosphorylation after stimulation by each agonist. Stably-transfected recombinant hFPR CHO cells were seeded onto transparent 96-well cell culture plates at $4 \times 10^4$ cells per well. After 6 h, cells were washed once with PBS, and then incubated in serum-free DMEM overnight, to allow FBS-stimulated phosphorylated ERK1/2 levels to subside. Cell were then stimulated with fMLP and Cmpd43 for 5 min, and Cmpd17b for 7 min based on the initial time-course studies, and incubated at 37° C. in 5% CO2. 10% (v:v) FBS was used as a positive control, with vehicle controls also included. The reaction was terminated by removal of study drugs and lysis of cells with 100 µL of SureFire lysis buffer (TGR Biosciences). Lysates were then transferred to 384-well opaque proxiplates. Under low-light conditions, a 1:120 (v:v) dilution of AlphaScreen beads (both acceptor and donor):Surefire reaction buffer was prepared, which was mixed with the activation buffer in a ratio of 6:1 (v:v), respectively. Plates were incubated in the dark at 37° C. for 1 h before the fluorescence signal was measured by a Fusion-α plate reader (PerkinElmer Life and Analytical Sciences, Foster City, Calif., USA) with standard AlphaScreen settings.

(iv) Measurement of Akt1/2/3 (Ser473) and Akt1 (Thr308) phosphorylation:Surefire Akt1/2/3 phosphorylation kits were also purchased from PerkinElmer Life and Analytical Science. Cells were lysed in SureFire lysis buffer and transferred to 384-well opaque proxiplates, using the same lysates as above. Under low-light conditions, a 1:10:40 (v:v:v) dilution of AlphaScreen acceptor beads:Surefire activation buffer:Surefire reaction buffer was prepared and the plate was incubated in the dark at RT for 2 h. Then, a 1:20 (v:v) dilution of AlphaScreen donor beads/dilution was prepared and incubated in the dark at RT for another 2 h, before the fluorescence signal was measured by used of a Fusion-α plate reader (PerkinElmer Life and Analytical Sciences) with standard AlphaScreen settings. For all ERK1/2 and Akt1/2/3 phosphorylation experiments, 10% FBS was used as internal positive control to stimulate pERK1/2 and pAkt1/2/3, and which the maximum responses were used for normalization of data, whilst vehicle was used as negative control, as described previously (May et al. 2010).

(v) cAMP Accumulation: Thirty minutes prior to stimulation, the culture medium of stably-transfected recombinant hFPR CHO cells was replaced with stimulation buffer [1.4 M NaCl, 50 mM KCl, 8 mM MgSO4, 2 mM Na2HPO4, 4.4 mM KH2PO4, 0.1% (w/v) BSA, 5 mM HEPES, 1.3 mM CaCl2, 5.6 mM glucose)] and 10 mM rolipram (selective phosphodiesterase-4 inhibitor), and treated with forskolin (3 µM), and incubated for 30 min at 37° C. in 5% CO2. Medium was aspirated and cAMP was extracted with 100% ice-cold ethanol and dried. Cells were lysed in detection buffer (dH2O, 0.3% Tween 20, 5 mM HEPES, 0.1% BSA). Using Surefire cAMP accumulation kits also purchased from PerkinElmer Life and Analytical Science, lysates were transferred to a 384-well plate and mixtures of detection buffer/donor bead-conjugated anti-cAMP antibody and detection buffer: biotinylated cAMP: acceptor bead-conjugated streptavidin were added to the lysates according to the PerkinElmer cAMP AlphaScreen protocol. Under low-light conditions, a 1:50 (v:v) dilution of AlphaScreen acceptor beads: stimulation buffer was prepared, 1:150 (v:v) dilution of donor beads and 50 nM biotinylated cAMP in detection buffer was prepared in 384-well opaque optiplates. Plates were incubated in the dark at room temperature overnight before the fluorescence signal was measured by use of a Fusion-α plate reader (PerkinElmer Life and Analytical Sciences). Data were normalized to the response elicited by 10 µM forskolin at the same time point.

(vi) Derivation of FPR agonist potency and maximal agonist response: Computerized nonlinear regression was performed using Prism 6.0 (GraphPad Software) as described previously (Kenakin et al. 2012 & Christopoulos et al. 2002). All affinities, potencies, and efficacies were estimated as logarithms. Concentration-response curves mediated by each agonist across the five pathways (intracellular Ca2+ mobilization, pERK1/2 phosphorylation, Akt1/2/3(Ser473) phosphorylation, Akt1(Thr308) phosphorylation and inhibition of cAMP accumulation) were fitted to derive the maximal agonist effect (Emax), and the ligand potency estimate (pEC50), where Emax is the maximal possible response of the system to a defined stimulus (not the agonist), while basal responses are in the absence of stimulus or agonist, and pEC50 is the negative logarithm of the agonist concentration that gives a response halfway between Emax and basal (FIG. 21B).

(vii) Quantification of biased agonism: Development of a quantitative framework of GPCR agonism allows ligand bias to be quantified and statistically analyzed. Using these data, the potential for biased agonism mediated by each agonist across each signal was quantified by first refitting each of the multiple signaling concentration-response curves obtained above, using an extension to the Black-Leff operational model as described previously (FIG. 21B)(Kenakin et al. 2012). A "transduction ratio" is firstly derived for each response (τ/KA, where τ represents efficacy, and KA affinity, of the agonist for each GPCR conformational state), extracted from each concentration-response curve. "Bias factors" (ΔΔ(τ/KA)) were then calculated by normalizing the transduction ratio to a reference ligand (in this case, Cmpd43) and reference pathway, which here was Akt1/2/3 (Thr308) phosphorylation. Lastly, bias factors were plotted on a 'web of bias' to visualize the potential for biased agonism. This approach nullifies the potential confounding influence of the cellular background on the observed agonism and facilitates a quantitative cross-pathway comparison for each agonist. Under these conditions, if the test agonist and the reference agonist activate the two pathways through a common receptor conformation, the log [bias factor] should be 0.0 (i.e. the bias factor 1.0), irrespective of differences in response amplification between pathways. In contrast, significant deviation of log [bias factor] away from 0.0 (i.e. where the bias factor is different to 1.0) indicates the involvement of distinct conformations for the different agonists. All affinities, potencies, efficacies, and cooperativity parameters were estimated as logarithms (Kenakin et al. 2012).

Cardiac injury responses in vivo: Small-molecule FPR-agonists Cmpd17b and Cmpd43 (FIG. 21A) were synthesized as described (Burli et al. 2006 & Cilibrizzi et al. 2009). Their impact on myocardial I-R injury in vivo was assessed in 3 separate cohorts of C57BL/6 mice (see online Supplement) (Gao et al. 2011). FPR-agonists Cmpd17b and Cmpd43 (50 mg/kg/day i.p. as described) or vehicle (10%-DMSO/0.8% Tween20 in saline i.p.) were administered immediately prior to reperfusion, with subsequent doses every 24 h until endpoint. Cardiac necrosis was assessed after 24 h reperfusion (Gao et al. 2011), on both infarct size (2,3,5-triphenyltetrazolium chloride [TTC]) and plasma cardiac troponin-I (cTnI). Cardiac and systemic inflammation were determined in a separate cohort of mice after 48 h reperfusion (Gao et al. 2011) across cardiac macrophage (CD68+) and neutrophil (Ly6B.2+) content, circulating white blood cells (WBC) and plasma interleukin IL-1β (detailed in online Supplement). Lastly, early cardiac remodeling (apoptosis, fibrosis) (Huynh et al. 2010) and plasma FPR-agonist levels were determined in a separate cohort after 7-days reperfusion.

Cardiomyocytes injury responses in vitro: Neonatal rat cardiomyocytes and adult mouse cardiofibroblasts were isolated and cultured as described (online Supplement). Cardiomyocytes were subjected to hypoxia-reoxygenation (H-R) to simulate I-R in vitro, with Cmpd17b, Cmpd43 or vehicle, added at the start of reoxygenation. Cardiomyocyte injury was assessed by measurement of cardiac cTnI in cardiomyocyte supernatant. Cardiofibroblasts were subjected to 24 h pro-fibrotic transforming growth factor (TGF)-β stimulation, with Cmpd17b, Cmpd43 or vehicle, added 30 mins prior to TGF-β. Expression of pro-fibrotic connective tissue growth factor (CTGF), pro-inflammatory IL-1β, Fpr1 and Fpr2 were then assessed.

Assessment of biased signaling at human FPRs in vitro: Refer to online Supplement for detailed description of generation and culture of stably-transfected Chinese hamster ovary (CHO) cells expressing recombinant human (but not native) FPRs, and the construction and analysis of concentration-response curves mediated by FPR-agonists Cmpd17b and Cmpd43. Results were compared to the widely-studied FPR1-selective agonist fMLP and FPR2-selective agonist LxA4. Five signaling pathways were examined, namely pERK1/2-phosphorylation, Akt1/2/3 (Ser473)-phosphorylation, Akt1(Thr308)-phosphorylation, increases in Ca2+i and inhibition of forskolin-induced cAMP accumulation. An operational model of agonism was fitted to each concentration-response curve to estimate a transduction ratio (τ/KA) for each agonist, at each pathway assessed, as described (FIG. 21B) (Kenakin et al. 2012). Transduction ratios were normalized to a reference agonist (Cmpd43) and a reference pathway (Akt1/2/3(Thr308)-phosphorylation), generating bias factors and therefore allowing quantitative cross-pathway comparison for each agonist.

Data analysis: All data were analyzed using GraphPad Prism 6.0 (GraphPad Software, San Deigo, Calif., USA). Results are expressed as means±SEM unless otherwise stated. Statistical analyses were by Student's t test, or one-way ANOVA followed by Dunnett's or Tukey's Comparison post-hoc test, as appropriate. Values of p<0.05 were considered statistically significant.

Results

Figure 13:
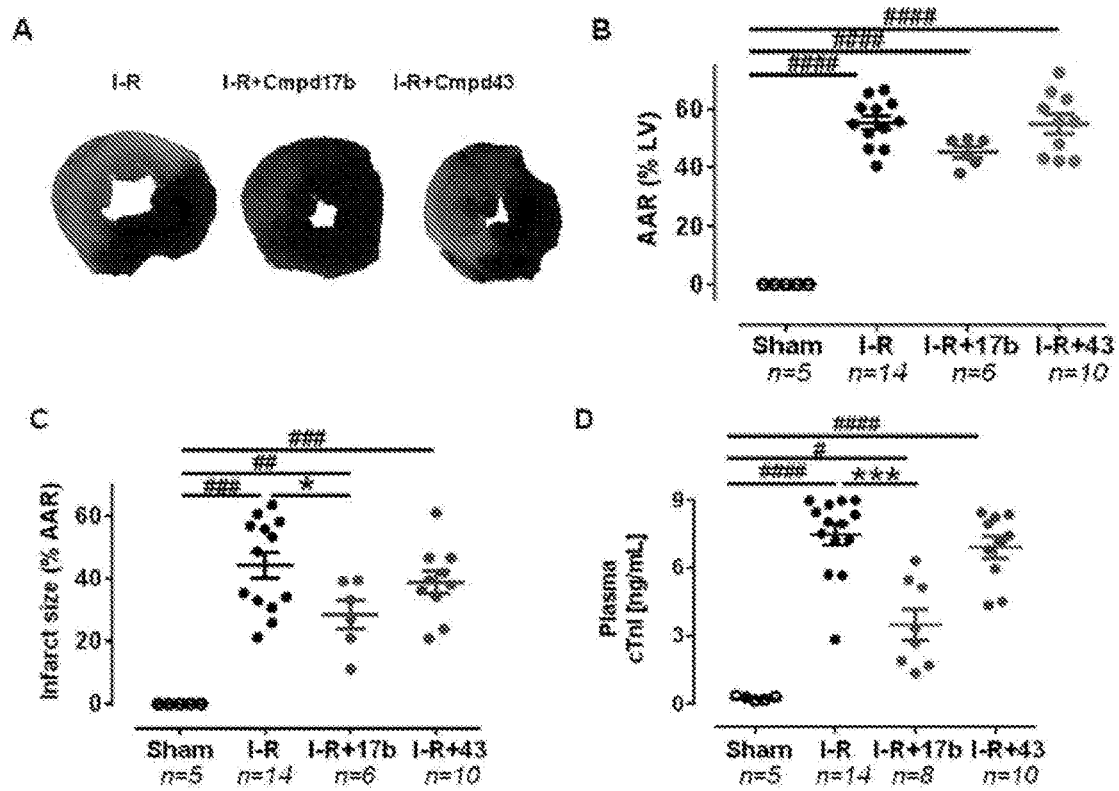
FIG. 13 is an image and graphical representation of FPR-agonist Cmpd17b reduces cardiac necrosis 24 h post I-R injury in vivo. (A) Representative TTC-stained LV transverse slices after 24 h reperfusion in mice allocated to vehicle, Cmpd17b or Cmpd43 (both 50 mg/kg i.p.)-treatment groups. Areas stained dark blue, white and red represented non-risk, infarcted, and ischemic but non-infarcted zones, respectively. Pooled data for (B) AAR (calculated as total infarcted plus ischemic but non-infarcted zones, % total LV), (C) Myocardial infarct size (% AAR), and (D) Plasma cTnI levels. Results are expressed as mean±SEM, with n per group indicated. #$P<0.05$, ###$P<0.001$ and ####$P<0.0001$ vs sham; *$P<0.05$ and ***$P<0.001$ vs vehicle-treated I-R on one-way-ANOVA with Tukey's post-hoc test.

FPR-agonist Cmpd17b reduces cardiac necrosis in vivo: We determined the impact of FPR-agonists (50 mg/kg, i.p., administered just prior to 24 h reperfusion) on cardiac necrosis in mice. There were no differences between I-R groups in the LV identified as the area-at-risk (AAR, ~60% on Evans blue) after 24 h (FIG. 13A,B). Of the AAR in vehicle-treated I-R mice, ~40% was infarcted (FIG. 13A,C) and plasma cTnI levels were markedly elevated (FIG. 13D). We demonstrated that Cmpd17b significantly reduced both infarct size (by ~35%, FIG. 13C) and cTnI levels (FIG. 13D). In contrast, Cmpd43 lacked cardioprotective actions compared to vehicle-treated I-R mice.

Figure 14:
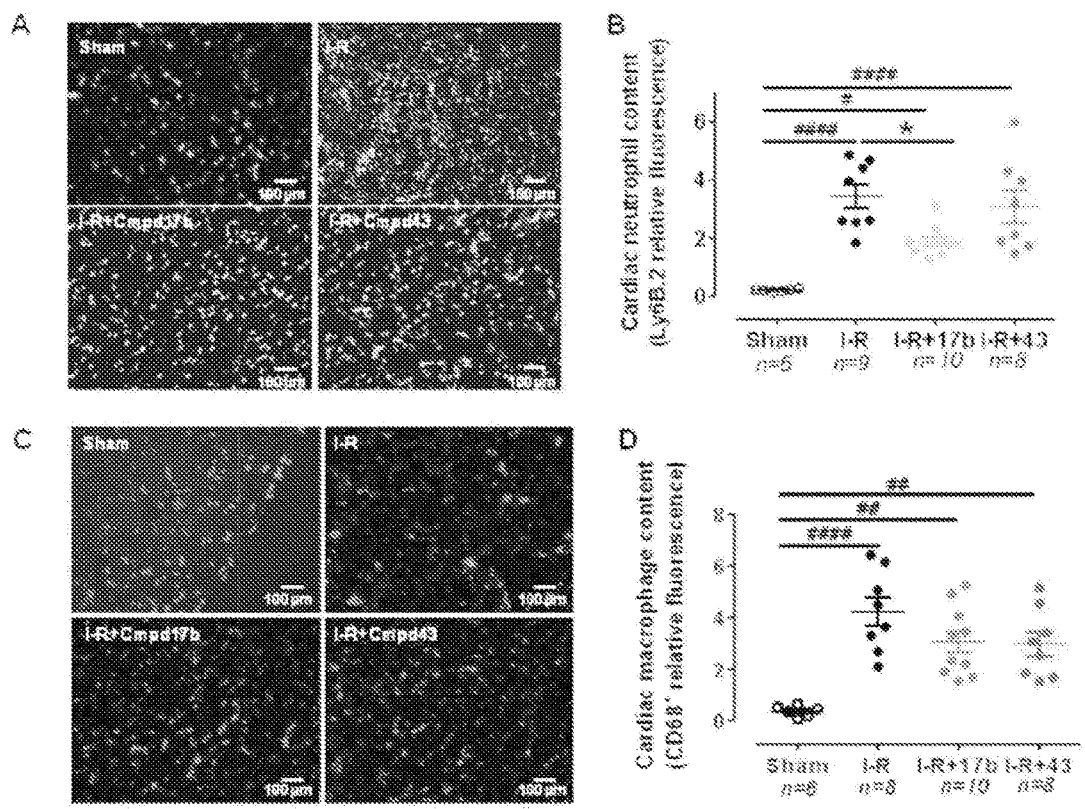
FIG. 14 is an image and graphical representation of FPR-agonist Cmpd17b reduces cardiac inflammation after 48 h post I-R injury. (A) Representative immunofluorescent images of LV neutrophil content (using anti-Ly-6B.2-antibody) from sham, vehicle-, and FPR-agonist-treated (Cmpd17b or Cmpd43, 50 mg/kg, i.p.) mice, 48 h post I-R.) B) Pooled data for LV Ly-6B.2-positive immunofluorescence. (C) Representative immunofluorescent images of LV macrophage content (using anti-CD68-antibody) from sham, vehicle-, and FPR-agonist-treated (Cmpd17b or Cmpd43, 50 mg/kg, i.p.) mice, 48 h post I-R. (D) Pooled data for LV CD68-positive immunofluorescence. Scale bars: 100 µm (40× magnification). Results are expressed as mean±SEM, with n per group indicated. #$P<0.05$ vs sham and *$P<0.05$ vs vehicle-treated mice on one-way-ANOVA with Tukey's post-hoc test.

FPR-agonist Cmpd17b attenuates cardiac and systemic inflammation in vivo: We assessed the extent of I-R-induced cardiac inflammation after 48 h reperfusion, via immunofluorescent-detection of LV neutrophil (anti-Ly-6B.2) and macrophage (anti-CD68) content. Cmpd17b significantly attenuated I-R-induced increases in LV neutrophil content compared to vehicle-treated I-R mice, by almost 50% (FIG. 14A-B, Suppl. FIG. 14A); this cardioprotective action was absent in Cmpd43-treated I-R mice. LV macrophage content was also significantly elevated in vehicle-treated I-R mice compared to sham, but this was not significantly blunted by either FPR-agonist (FIG. 14C-D, Suppl. FIG. 14B).

Figure 15:
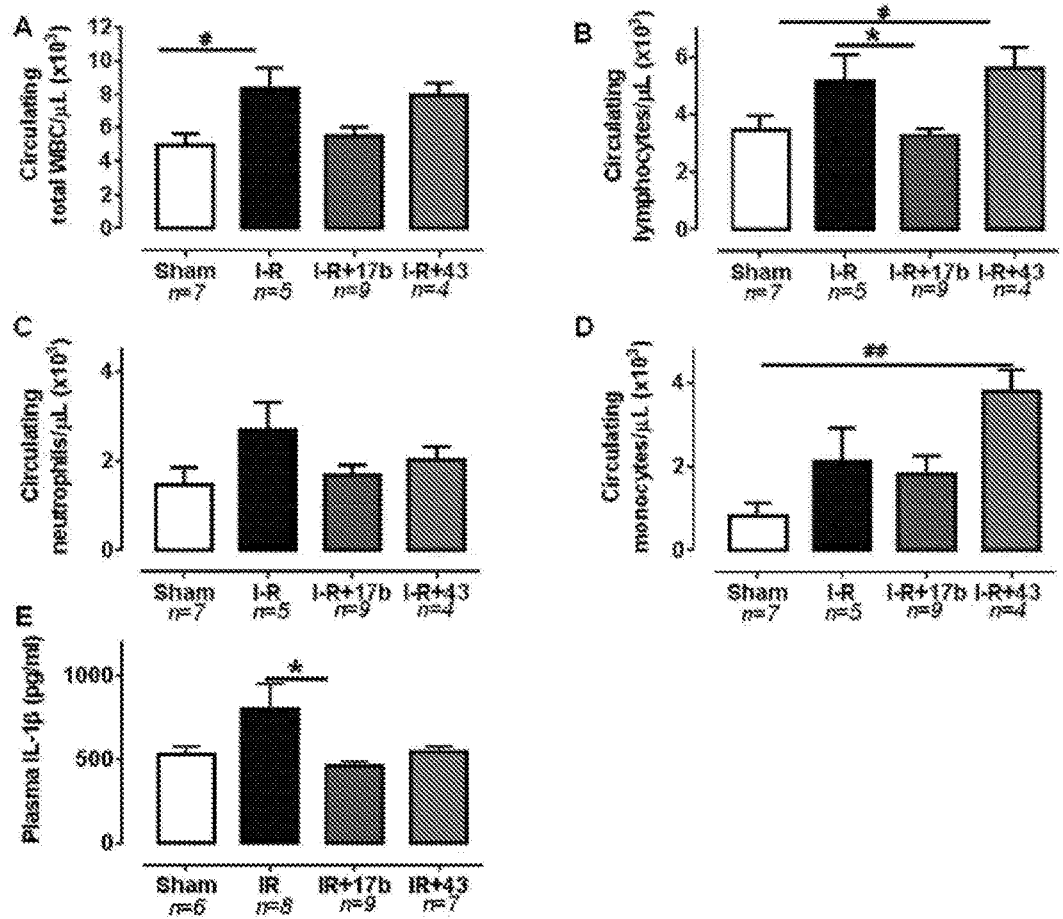
FIG. 15 is a graphical representation of FPR-agonist Cmpd17b reduces systemic inflammation 48 h post I-R injury. Circulating levels of A) Total WBCs, B) Lymphocytes, C) Neutrophils, D) Monocytes and E) IL-1β in sham, vehicle- and FPR-agonist-treated mice after 48 h reperfusion. Results are expressed as mean±SEM. #$P<0.05$ vs sham,*$P<0.05$ vs vehicle-treated mice on one-way-ANOVA with Tukey's post-hoc test.

Circulating total WBC were significantly increased in vehicle-treated mice compared to sham (FIG. 15A). I-R induced similar but non-significant trends in each of circulating lymphocytes (P=0.10), neutrophils (P=0.09) and pro-inflammatory IL-1β (P=0.10), consistent with systemic inflammation (FIG. 15B-E). Cmpd17b significantly blunted levels of circulating lymphocytes and IL-1β, without affecting circulating monocytes. Further, the I-R-induced increases in total WBC and neutrophils were absent in Cmpd17b-treated mice. In contrast, Cmpd43 significantly increased circulating monocytes and lymphocytes after 48 h reperfusion compared to sham. Together our observations suggest Cmpd17b (but not Cmpd43) attenuates the early inflammatory response associated with reperfusion injury.

FPR agonist Cmpd17b attenuates cardiac remodeling in vivo: Next, we determined the impact of FPR-agonists on I-R-induced cardiac apoptosis (by TUNEL) and fibrosis (by picrosirius red) after 7-days reperfusion. Myocardial I-R significantly increased cardiac apoptosis (FIG. 16A,B) and collagen deposition (FIG. 16C,D, FIG. 22C). Cmpd17 significantly attenuated LV apoptosis in the infarct area. The impact of I-R on LV fibrosis in this region was absent in Cmpd17b-treated mice. Further, Cmp17b significantly reduced heart and LV weights (normalized to bodyweight, FIG. 16E,F, Table 7). Cmpd43 again lacked these cardioprotective actions compared to vehicle-treated I-R mice.

Figure 17:
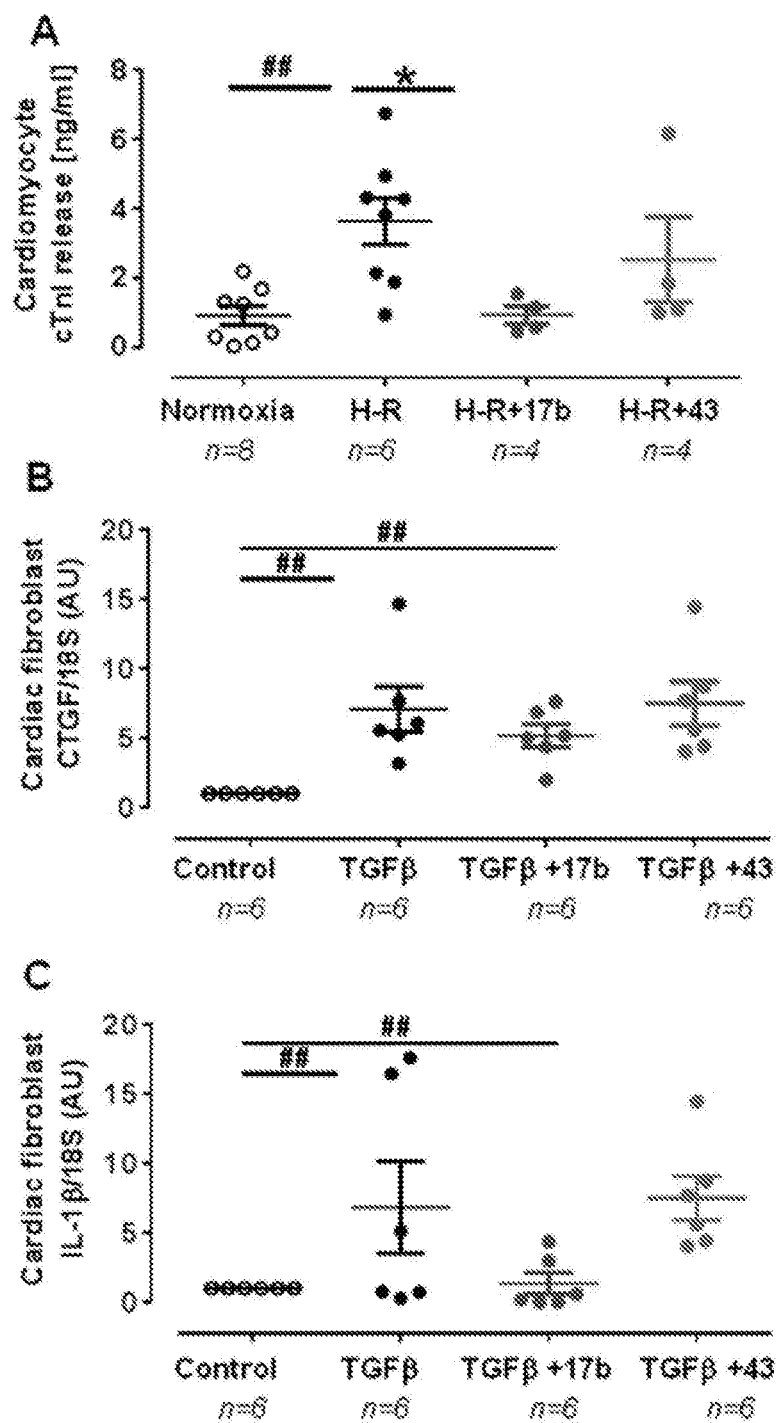
FIG. 17 is a graphical representation of the protective actions of FPR agonist Cmpd17b against cardiomyocyte injury responses in vitro. A) Effect of small-molecule FPR-agonists (both 1 µM, added on reoxygenation) on cardiomyocyte cTnI release subsequent to H-R. Effect of Cmpd17b and Cmpd43 (both 10 µM) on TGF-β stimulation of cardiofibroblast, B) pro-fibrotic, C) TGF and C pro-inflammatory IL-1β expression. Results expressed as mean±SEM. ##$P<0.05$ vs sham and *$P<0.05$ vs vehicle-treated H-R (cardiomyocytes) or TGF-β-stimulation (cardiofibroblasts), on one-way-ANOVA with Tukey's post-hoc test.
Figure 18:
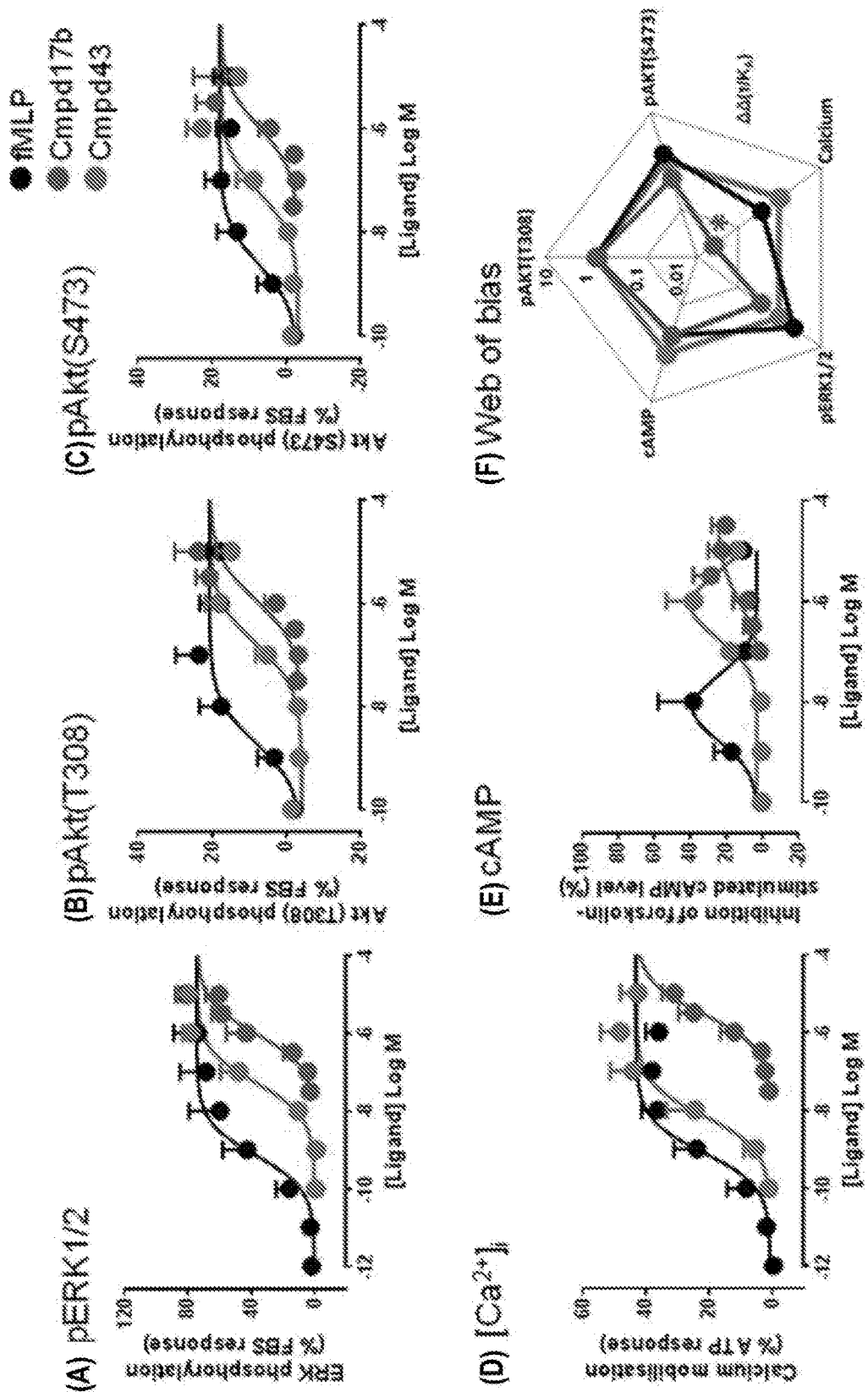
FIG. 18 is a graphical representation of signaling fingerprint of FPR-agonists in CHO cells stably-expressing hFPR1: Cmpd17b is a biased agonist of hFPR1. Impact of fMLP (black), Cmpd17b (blue) and Cmpd43 (red) on intracellular signaling intermediates downstream of GPCRs. A) ERK1/2-phosphorylation; B) Akt1/2/3Thr308-phosphorylation; C) Akt1/2/3Ser473-phosphorylation; D) Ca2+i; and E) inhibition of forskolin-stimulated cAMP accumulation. Results are expressed as mean±SEM of 3-4 experiments (each performed in triplicate). F) The 'web of bias' plots bias factors (ΔΔτ/KA) normalized to a reference agonist (Cmpd43) and a reference pathway (pAkt1/2/3Thr308), derived from results in panels A-E, expressed as the mean. *$P<0.05$ Cmpd17b vs Cmpd 43 for Ca2+i, one-way-ANOVA followed by Tukey's post-hoc test.
Figure 19:
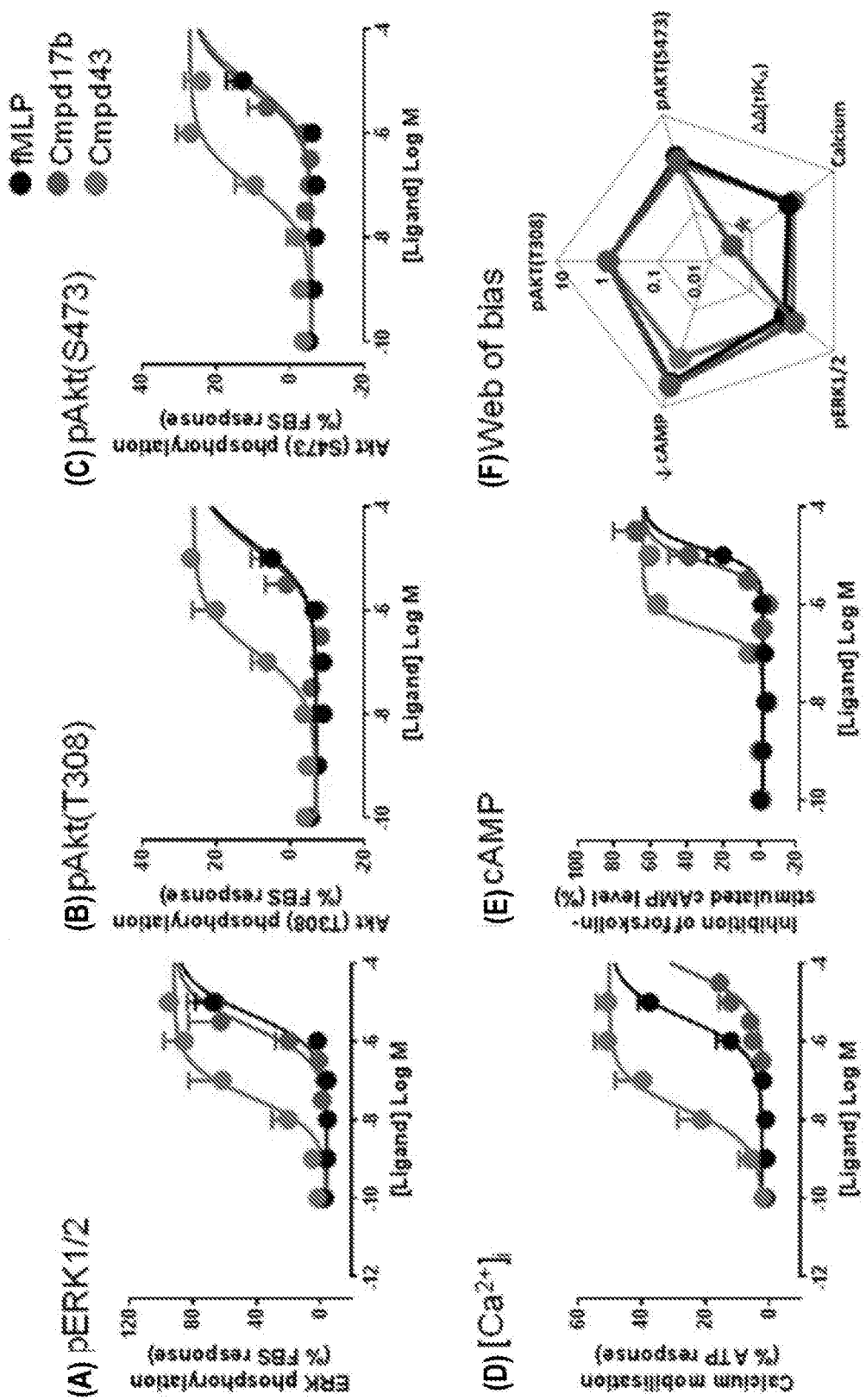
FIG. 19 is a graphical representation of signaling fingerprint of FPR-agonists in CHO cells stably-expressing hFPR2. Impact of fMLP (black), Cmpd17b (blue) and Cmpd43 (red) on intracellular signaling intermediates downstream of GPCRs. A) ERK1/2-phosphorylation; B) Akt1/2/3Thr308-phosphorylation; C) Akt1/2/3Ser473-phosphorylation; D) Ca2+i; and E inhibition of forskolin-stimulated cAMP accumulation. Results are expressed as mean±SEM of 3-4 experiments (each performed in triplicate). F) The 'web of bias' showing bias factors (ΔΔτ/KA) normalized to Cmpd43 and reference pathway pAkt1/2/3Thr308, derived from results in panels A-E, expressed as the mean. *$P<0.05$ Cmpd17b vs Cmpd 43 for Ca2+i, one-way-ANOVA followed by Tukey's post-hoc test.
Figure 20:
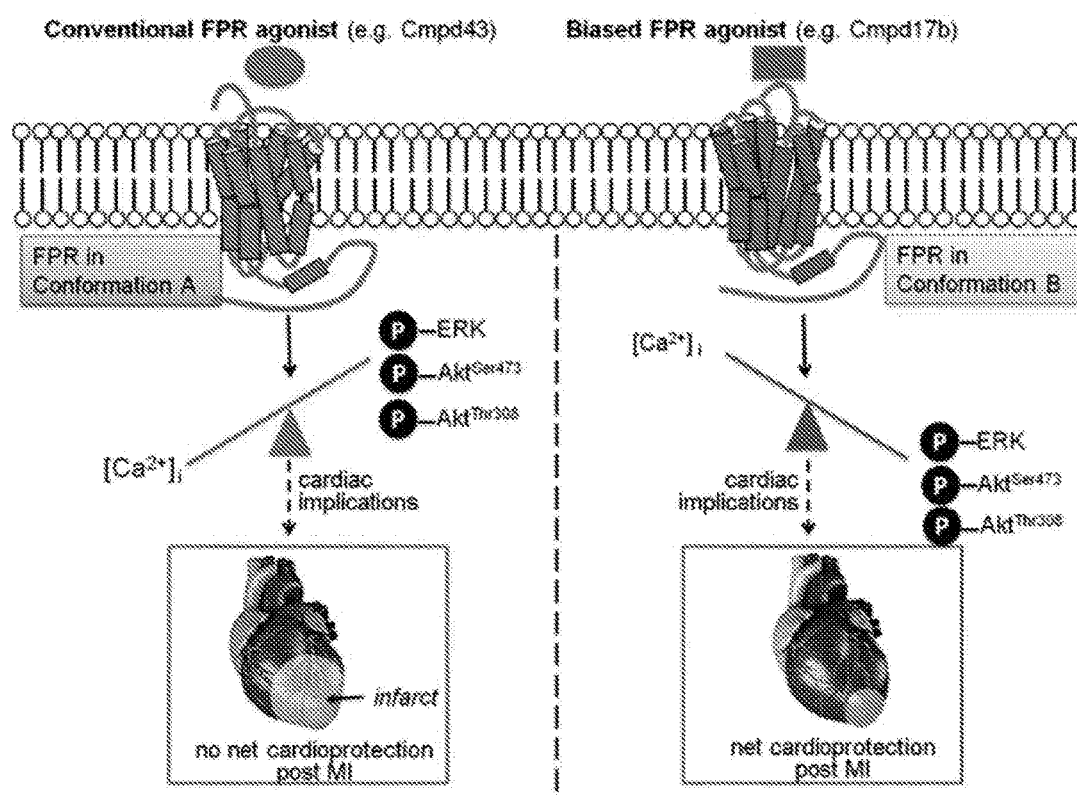
FIG. 20 is an image of the bias properties of FPR-agonists and implications for their role against myocardial I-R injury. Cmpd17b and Cmpd43 activate both FPR1 and FPR2, but Cmpd17b offers superior cardioprotective effect, likely through biased activation of desirable cardioprotective RISK signaling pathways (ERK1/2, Akt1/2/3Thr308, Akt1/

FPR-agonist Cmpd17b reduces cardiomyocytes injury responses in vitro: We assessed the direct effects of Cmp17b and Cmpd43 on cell injury responses in primary cardiomyocytes and cardiofibroblasts, both of which express native rodent Fpr1 and Fpr2 (FIG. 23). Using H-R to simulate I-R in vitro, we demonstrated that Cmpd17b rescued cardiomyocyte cTnI release post-H-R (FIG. 17A). The pro-fibrotic CTGF response to TGF-β remained significant in Cmpd43-treated (but not Cmpd17b-treated) cardiofibroblasts relative to control (FIG. 17B, P<0.01). In addition, the tendency for TGF-β-induced pro-inflammatory IL-1β responses tended to persist in Cmpd43-treated (but not Cmpd17b-treated) cardiofibroblasts, but this was not significant (FIG. 17C). Refer to online Supplement for treatment impact on cellular Fpr1/2 expression (FIG. 23).

Figure 16:
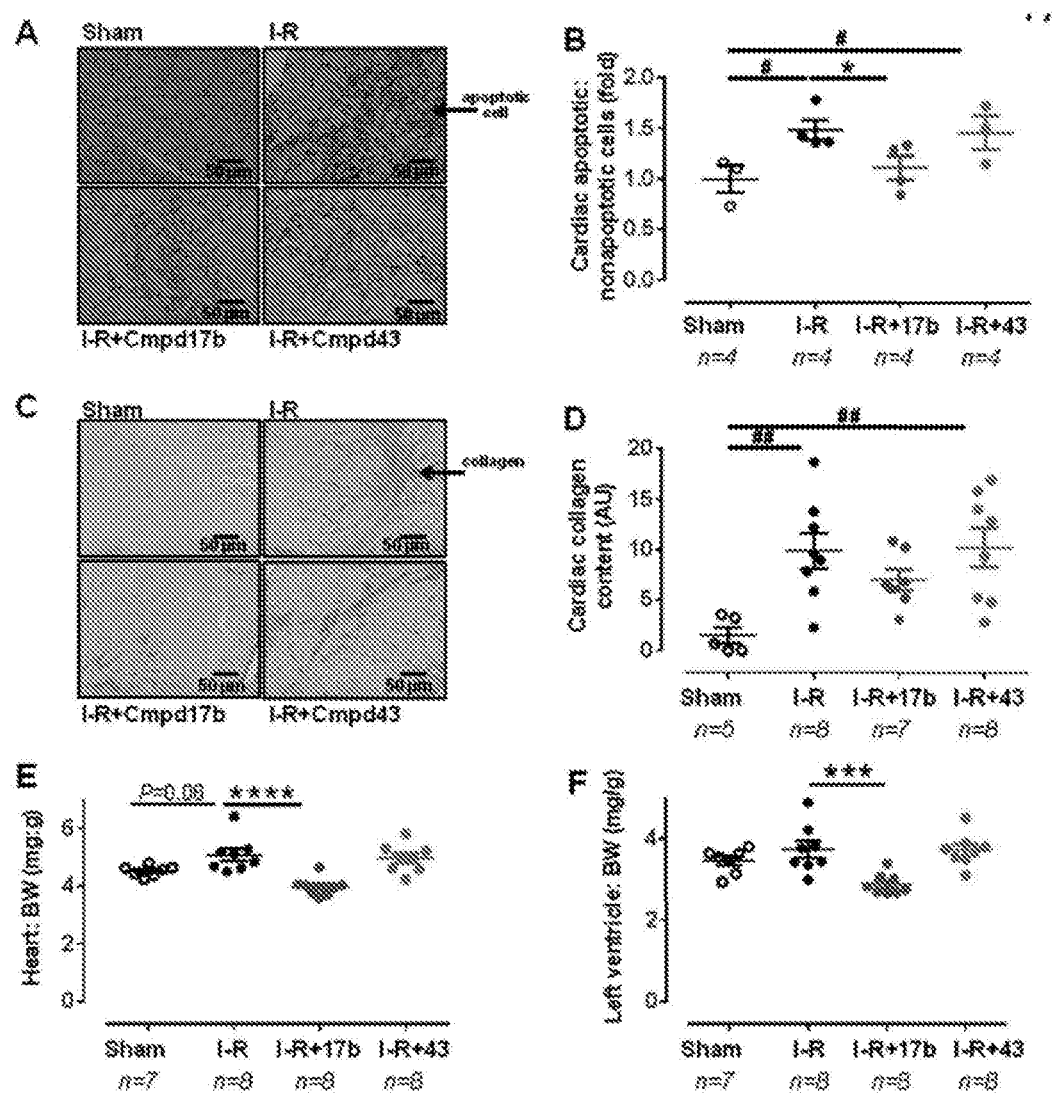
FIG. 16 is an image and graphical representation of FPR-agonist Cmpd17b reduces cardiac remodeling 7 days post I-R injury. A) Representative picrosirius red-stained LV cross-sections from sham, vehicle- and FPR-agonist (Cmpd17b or Cmpd43, 50 mg/kg i.p.)-treated mice, 7-days post I-R. B) Quantification of cardiac fibrosis (collagen appears red); magnification ×200. C) Representative LV sections using CardioTAC In Situ Apoptosis Detection (positively-stained apoptotic cells appear dark blue, indicated by arrow); magnification ×200. D) Quantification of apoptotic:non-apoptotic cells (expressed as fold sham). E) Heart and F) LV weight normalized to BW 7-days post I-R. Results are expressed as mean±SEM. #$P<0.05$, ##$P<0.01$ vs sham; *$P<0.05$, *$P<0.001$, **$P<0.0001$ vs vehicle-treated mice on one-way-ANOVA with Tukey's post-hoc test.

FPR-agonists Cmpd17b and Cmpd43 activate human FPR1 and FPR2: Lastly, we assessed the FPR1/FPR2-signaling fingerprints of the FPR-agonists Cmpd17b and Cmpd43 in vitro in Flp-In-CHO cells stably-expressing human FPR1 (hFPR1-CHO) or human FPR2 (hFPR2-CHO). Both Cmpd17b and Cmpd43 stimulated concentration-dependent phosphorylation of key cardiomyocyte survival pathways ERK1/2, Akt1/2/3(Thr308) and Akt1/2/3 (Ser474), and an increase in Ca2+I (key to both Ca2+-overload-induced cardiomyocyte loss post I-R as well as inflammatory cell migration) in hFPR1-CHO (FIG. 18A-D) and hFPR2-CHO (FIG. 19A-D) cells. Both Cmpd17b and Cmpd43 inhibited forskolin-stimulated cAMP accumulation in hFPR1-CHO (FIG. 18E) and hFPR2-CHO (FIG. 7E) cells, consistent with FPR1/2-coupling to Gi/o proteins, inhibiting adenylate cyclase. However, in hFPR1-CHO cells, Cmpd43 and fMLP stimulated cAMP accumulation at higher concentrations, yielding a bi-phasic curve; the EC50 was hence derived over the concentration range that inhibited cAMP. At both FPR1 and FPR2, Cmpd43 exhibited a higher potency than Cmpd17b for each signaling pathway assessed (Table 8). The high-affinity FPR1-selective agonist fMLP stimulated concentration-dependent increases in Ca2+i, inhibition of cAMP accumulation and phosphorylation of ERK1/2, Akt1/2/3(Thr308) and Akt1/2/3(Ser474) in hFPR1-CHO cells, with higher (nanomolar) potency but similar maxima to Cmpd17b and Cmpd43 (FIG. 18A-E, Table 8). The putative FPR2-selective agonist LxA4 failed to stimulate ERK-phosphorylation downstream of any hFPR-subtype (FIG. 16). None of the agonists tested elicited ERK-phosphorylation in hFPR3-CHO cells (FIG. 24), confirming specificity of the observed responses to the relevant hFPR1/hFPR2-subtype.

Cmpd17b is a biased FPR-agonist: GPCRs can isomerize between a spectrum of conformational states, each signaling response reflecting a particular subset of these. To assess potential for ligand bias at a given GPCR, it is imperative that multiple signaling responses be incorporated into quantitative analysis; bias cannot be predicted on potency to a single response (Kenakin et al. 2012). In the present study, an operational model of agonism was fitted to concentration-response curves for each of the five signaling pathways. This generated a transduction coefficient (t/KA) for each agonist at each signaling endpoint, a composite value of ligand efficacy (t) and affinity (KA) that provides a measure of the overall power of an agonist (Kenakin et al. 2012) (FIG. 21B). Bias factors derived for each agonist for each downstream signal at hFPR1 and hFPR2-subtypes are shown in Table 8. The 'web of bias', which enables visualization of bias factors, reveals that relative to Cmpd43, Cmpd17b was significantly biased away from Ca2+i at both FPR1 (FIG. 18F) and FPR2 (FIG. 19F), by approximately 30-fold.

Systemic and cardiac characteristics following I-R injury in vivo: Body and organ weights measured after 48 h and 7 days reperfusion are shown in Table 7. Following 48 h post-ischemic reperfusion, no differences in body, atria or lung weights were observed. Wet heart weight (HW) was however significantly increased in vehicle-, and Cmpd17b-treated, I-R mice when normalized to body weight (BW). A similar but non-significant trend for heart: body weight ratio (HW:BW) was evident after 7 days reperfusion with vehicle-treated I-R compared to sham mice (p=0.07, Table 7). Interestingly, administration of Cmpd17b (50 mg/kg/day i.p.) significantly reduced both total HW, and LV weight normalized to BW, consistent with protective actions of Cmpd17b on cardiac remodeling post I-R. This cardioprotection was however not shared by Cmpd43 at the same dosing regimen, despite plasma concentrations of both FPR small molecule agonists exceeding 0.1 µM approximately 20 h after the final dose in mice subjected to 7 days reperfusion, with plasma Cmpd43 levels in the micromolar range at this timepoint.

Relative expression of Fprs in NRCMs and AMCFs in vitro: As shown in FIG. 23A, the relative expression of Fprs in normoxic NRCMs is rFpr1>rFpr2>>rFpr3, assessed by real-time PCR. Cmpd17b did not significantly influence NRCM expression of rFpr1 (FIG. 23B) or rFpr2 (FIG. 23C) after 48 h incubation. In contrast, Cmpd43 tended to reduce NRCM expression of rFpr2 (P=0.05) but was without impact on NRCM rFpr1 expression. As shown in FIG. 23D, the relative expression of Fprs in untreated AMCFs is mFpr2>mFpr1; mFpr3 was not determined. TGF-β reduced AMCF expression of both mFpr1 (FIG. 23E) and mFpr2 (FIG. 23F) after 24 h incubation. Cmpd17b did not significantly influence AMCF expression of either mFpr1 or mFpr2; Cmpd43 by contrast restored AMCF expression of mFpr1 (FIG. 23).

Timecourse of FPR agonist effects at hFPRs in vitro: effect of LxA4: To elucidate the optimal timing of activation of each FPR agonist on each FPR subtype, we performed a pilot study to ascertain the timecourse of ERK1/2 phosphorylation in response to fMLP, Cmpd17b, Cmpd43 and LxA4 (each 10 µM). As shown in FIGS. 24A and 24B, maximal ERK1/2 phosphorylation was observed after 5 mins treatment with fMLP and Cmpd43 in both hFPR1 and hFPR2-CHO cells, whereas 7 mins was the timepoint of maximal effect of Cpmd17b. None of the 4 FPR agonists elicited effects at hFPR3 (FIGS. 24C and 24D). LxA4 was without effect on any hFPR subtype, regardless of concentration studied (FIG. 24E).

Example 4

Quantitative Fingerprinting: BIDI-001 exhibits biased signalling away from Ca2+i at FPR1 in CHO cells in vitro (yet leaving ERK1/2 & Akt phosphorylation intact). Importantly, despite having lower CHO cell potency, BIDI-001 (but not Cmpd43) conferred cardioprotection both in isolated cardio-myocytes in vitro & intact heart subjected to MI in vivo. These results suggest bias away from Ca2+i (implicated in both inflammation & cardiomyocyte death post MI) may be predictive of superior in vivo cardioprotection. This suggestions is further substantiated by results on compounds 10394 and 10396 of which only 10396 displays Ca2+i bias in vitro & confers cardioprotection in vivo (FIG. 25 and Table 9).

TABLE 1

Potency (pEC$_{50}$), and maximal agonist [Ca$^{2+}$]$_i$ mobilization response (E$_{max}$) in FlpIn-CHO cells stably expressing the hFPR1 receptor or hFPR2 receptor. Data points represent as percentage of the mean ± SEM of [Ca$^{2+}$]$_i$ mobilization elicited by ATP from 3-7 experiments performed in triplicate, n indicates number of independent experiments. p < 0.01, **p < 0.0001 vs. fMLP; ###p < 0.001, ####p < 0.0001 vs BIDI-001, one-way ANOVA followed by Dunnett's Comparison post-hoc tests

| [Ca$^{2+}$]$_i$ mobilization | hFPR1-FlpIn-CHO | | | hFPR2-FlpIn-CHO | | |
|---|---|---|---|---|---|---|
| | pEC$_{50}$ | E$_{max}$ (%) | n | pEC$_{50}$ | E$_{max}$ (%) | n |
| fMLP | 9.04 ± 0.16 | 38 ± 6 | 4 | 5.79 ± 0.13 | 38 ± 4 | 3 |
| BIDI-001 | 5.79 ± 0.19**** | 31 ± 4 | 7 | 5.24 ± 0.13 | 16 ± 2****#### | 4 |
| BIDI-002 | 7.96 ± 0.19**#### | 43 ± 6 | 7 | 7.68 ± 0.33**### | 51 ± 3* | 5 |

TABLE 2

Potency (pEC$_{50}$), and maximal agonist pERK1/2 response (E$_{max}$ %) in FlpIn-CHO cells stably expressing the hFPR1 or hFPR2. Data points represent as percentage of the mean ± SEM of ERK1/2 phosphorylation elicited by 10% FBS from 4-6 experiments performed in triplicate, n indicates number of independent experiments. p < 0.01, **p < 0.0001 vs. fMLP; #p < 0.05 vs BIDI-001, one-way ANOVA followed by Tukey's post-hoc tests.

| ERK1/2 phosphorylation | hFPR1-FlpIn-CHO | | | hFPR2-FlpIn-CHO | | |
|---|---|---|---|---|---|---|
| | pEC$_{50}$ | E$_{max}$ (%) | n | pEC$_{50}$ | E$_{max}$ (%) | n |
| fMLP | 9.01 ± 0.58 | 80 ± 7 | 6 | 5.23 ± 0.14 | 68 ± 11 | 4 |
| BIDI-001 | 6.06 ± 0.24** | 82 ± 6 | 6 | 5.44 ± 0.42 | 66 ± 18 | 4 |
| BIDI-002 | 7.17 ± 0.24*** | 61 ± 9 | 6 | 7.26 ± 0.41 | 95 ± 4**# | 4 |

TABLE 3

Potency (pEC$_{50}$), and maximal agonist pAkt1/2/3 (Ser473) and pAkt1/2/3 (Thr308) response (E$_{max}$ %) in FlpIn-CHO cells stably expressing the hFPR1 or FPR2. Data points represent as percentage of the mean ± SEM of Akt1/2/3 phosphorylation elicited by 10% FBS from 4-5 experiments. p < 0.01, **p < 0.0001 vs. fMLP; #p < 0.05 vs BIDI-001, one-way ANOVA followed by Tukey's post-hoc tests.

| | hFPR1-FlpIn-CHO | | | hFPR2-FlpIn-CHO | | |
|---|---|---|---|---|---|---|
| | pEC$_{50}$ | E$_{max}$ (%) | n | pEC$_{50}$ | E$_{max}$ (%) | n |
| Akt 1 (Thr308) phosphorylation | | | | | | |
| fMLP | 8.90 ± 0.32 | 18 ± 4 | 5 | ND | 7 ± 2 | 5 |
| BIDI-001 | 5.66 ± 0.23**** | 24 ± 6 | 5 | ND | 10 ± 3 | 5 |
| BIDI-002 | 6.89 ± 0.32**# | 15 ± 4 | 5 | 6.86 ± 0.19 | 27 ± 2 | 5 |
| Akt 1/2/3 (Ser473) | | | | | | |
| fMLP | 9.01 ± 0.46 | 16 ± 4 | 4 | ND | 13 ± 4 | 5 |
| BIDI-001 | 5.81 ± 0.24**** | 18 ± 7 | 5 | ND | 13 ± 3 | 5 |
| BIDI-002 | 7.06 ± 0.31**# | 13 ± 3 | 5 | 6.84 ± 0.33 | 30 ± 6 | 5 |

TABLE 4

Potency ($pEC_{50}$), and maximal agonist cAMP accumulation inhibition response ($E_{max}$) in FlpIn-CHO cells stably expressing the hFPR1 or hFPR2. Data points represent as percentage of the mean ± SEM of inhibition to cAMP accumulation from 3-4 experiments. p < 0.01, * p < 0.001, vs. fMLP, one-way ANOVA followed by Tukey's post-hoc tests.

| Inhibition to cAMP accumulation | hFPR1-FlpIn-CHO | | | hFPR2-FlpIn-CHO | | |
|---|---|---|---|---|---|---|
| | $pEC_{50}$ | $E_{max}$ (%) | n | $pEC_{50}$ | $E_{max}$ (%) | n |
| fMLP | 7.34 ± 0.01 | 28 ± 12 | 3 | 5.46 ± 0.54 | 10 ± 8 | 4 |
| BIDI-001 | 6.30 ± 0.15 | 12 ± 10 | 4 | 4.87 ± 0.09 | 47 ± 6** | 4 |
| BIDI-002 | 7.13 ± 0.37 | 27 ± 20 | 3 | 6.77 ± 0.10 | 66 ± 6*** | 4 |

TABLE 5

Effect of 48 h myocardial I-R and $Ac_{2-26}$, BIDI-001, BIDI-002 treatment on body and organ weights. #P < 0.05 versus sham, P < 0.05 versus vehicle treated mice. One-way ANOVA with Tukey post-hoc test. Data were represented as mean ± SEM.

| | | Sham | I-R + vehicle | I-R + $AC_{2-26}$ | I-R + BIDI-001 | I-R + BIDI-002 |
|---|---|---|---|---|---|---|
| No. of mice | | 6 | 17 | 9 | 10 | 7 |
| Body Weight (g) | | 26.9 ± 1.3 | 29.0 ± 0.4 | 28.2 ± 1.0 | 28.2 ± 1.0 | 27 ± 0.6 |
| Organ weight (mg) | heart | 113 ± 5 | 135 ± 4# | 144 ± 6# | 147 ± 11 | 132 ± 11 |
| | atria | 8.2 ± 1.0 | 10.9 ± 0.5 | 10.1 ± 0.7 | 14.6 ± 1.2 | 9.9 ± 2.8 |
| | LV | 83.2 ± 4.5 | 95.4 ± 6.5 | 109.8 ± 5.5 | 105.0 ± 8.3 | 94.9 ± 7.5 |
| | RV | 21.1 ± 1.5 | 21.9 ± 1.6 | 24.3 ± 0.9 | 24.9 ± 3.1 | 22.9 ± 1.7 |
| | lung | 140 ± 8 | 146 ± 4 | 145 ± 9 | 157 ± 6 | 154 ± 6 |
| Organ weight: body weight (mg/g) | heart | 4.2 ± 0.1 | 4.8 ± 0.2# | 5.0 ± 0.2# | 5.2 ± 0.3# | 4.8 ± 0.3 |
| | atria | 0.3 ± 0.0 | 0.4 ± 0.0 | 0.3 ± 0.0 | 0.5 ± 0.0 | 0.5 ± 0.1 |
| | LV | 3.1 ± 0.1 | 3.6 ± 0.1 | 3.8 ± 0.2# | 3.7 ± 0.2 | 3.5 ± 0.2 |
| | RV | 0.8 ± 0.1 | 0.8 ± 0.1 | 0.8 ± 0.0 | 1.0 ± 0.0 | 0.8 ± 0.0 |
| | lung | 5.2 ± 0.2 | 5.3 ± 0.1 | 5.0 ± 0.3 | 5.6 ± 0.2 | 5.7 ± 0.1 |

TABLE 6

Effect of 7 d myocardial I-R and $Ac_{2-26}$, BIDI-001, BIDI-002 treatment on body and organ weights. #P < 0.05 versus sham, P < 0.05 versus vehicle treated mice. One-way ANOVA with Tukey post-hoc test. Data were represented as mean ± SEM.

| | | Sham | I-R + vehicle | I-R + $AC_{2-26}$ | I-R + BIDI-001 | I-R + BIDI-002 |
|---|---|---|---|---|---|---|
| No. of mice | | 6 | 14 | 6 | 8 | 8 |
| Body Weight (g) | | 26.3 ± 0.5 | 25.5 ± 0.6 | 25.6 ± 1.0 | 24.3 ± 0.5 | 23.8 ± 0.9 |
| Organ weight (mg) | heart | 118 ± 5 | 131 ± 4 | 129 ± 10 | 96 ± 4* | 118 ± 6 |
| | atria | 6.3 ± 0.2 | 10.3 ± 0.7# | 8.3 ± 1.0 | 7.3 ± 0.8* | 7.8 ± 0.5 |
| | LV | 86.7 ± 3.2 | 98.8 ± 4.8 | 102.9 ± 6.5# | 70.1 ± 2.9* | 89.0 ± 4.2 |
| | RV | 21.1 ± 1.0 | 22.1 ± 1.0 | 17.8 ± 2.4 | 19.0 ± 1.0 | 21.4 ± 1.6 |
| | lung | 148 ± 7 | 142 ± 4 | 147 ± 7 | 132 ± 3 | 138 ± 7 |
| Organ weight: body weight (mg/g) | heart | 4.6 ± 0.2 | 5.2 ± 0.2 | 5.0 ± 0.2 | 4.0 ± 0.1* | 5.0 ± 0.2 |
| | atria | 0.2 ± 0.0 | 0.4 ± 0.00# | 0.3 ± 0.0 | 0.3 ± 0.0 | 0.3 ± 0.0 |
| | LV | 3.4 ± 0.1 | 3.9 ± 0.2 | 4.0 ± 0.2# | 2.9 ± 0.1* | 3.7 ± 0.1 |
| | RV | 0.8 ± 0.1 | 0.9 ± 0.1 | 0.7 ± 0.1 | 0.8 ± 0.3 | 0.9 ± 0.1 |
| | lung | 5.8 ± 0.3 | 5.6 ± 0.16 | 5.7 ± 0.2 | 4.7 ± 0.7 | 5.8 ± 0.3 |

TABLE 7

Impact of I-R in the presence and absence of Cmpd17b and Cmpd43 treatment on body and organ weights 48 h and 7 days following I-R injury.

|  |  | Sham | I-R | I | I-R + Cmpd43 |
|---|---|---|---|---|---|
| 48 h myocardial I-R ||||||
| n |  | 6 | 9 | 10 | 7 |
| Body Weight (BW, g) |  | 27 ± 1 | 29 ± 1 | 28 ± 1 | 27 ± 1 |
| Organ weight: BW (mg/g) | heart | 4.2 ± 0.2 | 4.6 ± 0.2# | 5.2 ± 0.3# | 4.8 ± 0.3 |
|  | atria | 0.3 ± 0.0 | 0.4 ± 0.0 | 0.5 ± 0.0 | 0.5 ± 0.1 |
|  | LV | 3.1 ± 0.1 | 3.6 ± 0.1 | 3.7 ± 0.2 | 3.5 ± 0.2 |
|  | RV | 0.8 ± 0.1 | 0.8 ± 0.1 | 1.0 ± 0.0 | 0.8 ± 0.0 |
|  | lung | 5.2 ± 0.2 | 5.4 ± 0.1 | 5.6 ± 0.2 | 5.7 ± 0.1 |
| 7 days myocardial I-R ||||||
| n |  | 6 | 14 | 8 | 8 |
| BW (g) |  | 26 ± 1 | 26 ± 1 | 24 ± 1 | 24 ± 1 |
| Organ weight: BW (mg/g) | heart | 4.6 ± 0.2 | 5.2 ± 0.2 | 4.0 ± 0.1* | 5.0 ± 0.2 |
|  | Atria | 0.2 ± 0.0 | 0.4 ± 0.0# | 0.3 ± 0.0 | 0.3 ± 0.0 |
|  | LV | 3.3 ± 0.2 | 3.9 ± 0.2 | 2.9 ± 0.1* | 3.7 ± 0.1 |
|  | RV | 0.8 ± 0.1 | 0.9 ± 0.1 | 0.8 ± 0.3 | 0.9 ± 0.1 |
|  | lung | 5.8 ± 0.3 | 5.6 ± 0.2 | 5.4 ± 0.1 | 5.8 ± 0.3 |

TABLE 8

FPR agonist potency (pEC$_{50}$), maximal agonist response (E$_{max}$), transduction coefficient (Log($\tau$/K$_A$)), and "normalized" transduction coefficient ($\Delta$ Log($\tau$/K$_A$)) for phosphorylation of ERK1/2, Akt1/2/3(Thr308), Akt1/2/3(Ser473), intracellular Ca$^{2+}$ mobilization and inhibition of cAMP accumulation in CHO cells stably expressing hFPR1 or hFPR2. Data represents percent of the mean ± SEM of response elicited by 10% FBS (phosphorylation), ATP (Ca2+ mobilization) or inhibition of forskolin-induced cAMP accumulation, from 3-7 experiments performed in triplicate, n indicates number of independent experiments. p < 0.01, **p < 0.0001 vs. fMLP; ###p < 0.001, ####p < 0.0001 vs. Cmpd17b, ⁀p < 0.01, ⁀⁀p < 0.001 vs. intracellular Ca2+ mobilization, one-way ANOVA followed by Tukey's post-hoc tests.

| | hFPR1-FlpIn-CHO |  |  |  |  | hFPR2-FlpIn-CHO |  |  |  |
|---|---|---|---|---|---|---|---|---|---|
|  | pEC$_{50}$ | E$_{max}$ | Log($\tau$/K$_A$) | $\Delta$Log($\tau$/K$_A$) | n | pEC$_{50}$ | E$_{max}$ | Log($\tau$/K$_A$) | $\Delta$Log($\tau$/K$_A$) | n |
| ERK1/2 phosphorylation |||||||||||
| fMLP | 9.0 ± 0.6 | 80 ± 7 | 9.6 ± 0.2 | 2.3 ± 0.1 | 6 | 5.2 ± 0.1 | 68 ± 11 | 5.4 ± 0.1 | −2.3 ± 0.2 | 4 |
| Cmpd17b | 6.1 ± 0.2** | 82 ± 6 | 6.0 ± 0.2 | −1.3 ± 0.2⁀⁀ | 6 | 5.4 ± 0.4 | 66 ± 18 | 5.8 ± 0.1 | −1.9 ± 0.3⁀ | 4 |
| Cmpd43 | 7.2 ± 0.2*** | 61 ± 9 | 7.3 ± 0.1 | 0.0 | 6 | 7.3 ± 0.4**# | 95 ± 4 | 7.7 ± 0.2 | 0.0 | 4 |
| Akt 1/2/3 (Thr308) phosphorylation |||||||||||
| fMLP | 8.9 ± 0.3 | 18 ± 4 | 8.8 ± 0.3 | 1.9 ± 0.1 | 5 | 4.7 ± 0.2 | 21 ± 2 | 4.8 ± 0.1 | −2.1 ± 0.3 | 5 |
| Cmpd17b | 5.7 ± 0.2**** | 24 ± 6 | 6.0 ± 0.1 | −0.9 ± 0.2⁀ | 5 | 4.8 ± 0.1 | 21 ± 3 | 5.1 ± 0.2 | −1.9 ± 0.2⁀ | 5 |
| Cmpd43 | 6.9 ± 0.3**# | 15 ± 4 | 6.9 ± 0.3 | 0.0 | 5 | 6.9 ± 0.2**# | 27 ± 2 | 7.0 ± 0.2 | 0.0 | 5 |
| Akt 1/2/3 (Ser473) phosphorylation |||||||||||
| fMLP | 9.0 ± 0.5 | 16 ± 4 | 9.0 ± 0.4 | 2.1 ± 0.3 | 4 | 5.0 ± 0.1 | 20 ± 4 | 4.9 ± 0.2 | −2.0 ± 0.2 | 5 |
| Cmpd17b | 5.8 ± 0.2**** | 18 ± 7 | 5.7 ± 0.2 | −1.3 ± 0.3⁀ | 5 | 5.0 ± 0.1 | 20 ± 3 | 5.1 ± 0.2 | −1.9 ± 0.2⁀ | 5 |
| Cmpd43 | 7.1 ± 0.3**# | 13 ± 3 | 6.9 ± 0.3 | 0.0 | 5 | 6.8 ± 0.3**# | 30 ± 6 | 6.9 ± 0.4 | 0.0 | 5 |
| [Ca$^{2+}$]$_i$ mobilization |||||||||||
| fMLP | 9.0 ± 0.2 | 38 ± 6 | 8.4 ± 0.3 | 1.5 ± 0.7 | 4 | 5.8 ± 0.1 | 38 ± 4 | 5.4 ± 0.1 | −2.2 ± 0.3 | 3 |
| Cmpd17b | 5.8 ± 0.2**** | 31 ± 4 | 5.5 ± 0.2 | −2.5 ± 0.1 | 7 | 5.2 ± 0.1 | 16 ± 2*** | 4.3 ± 0.1 | −3.4 ± 0.3 | 4 |
| Cmpd43 | 8.0 ± 0.2**#### | 43 ± 6 | 8.0 ± 0.2 | 0.0 | 7 | 7.7 ± 0.3**### | 51 ± 3**#### | 7.7 ± 0.3 | 0.0 | 5 |
| Inhibition of cAMP accumulation |||||||||||
| fMLP | 7.3 ± 0.0 | 28 ± 12 | 8.6 ± 0.3 | 1.5 ± 0.5 | 3 | 5.5 ± 0.5 | 10 ± 8 | 4.9 ± 0.1 | −1.6 ± 0.2 | 4 |
| Cmpd17b | 6.3 ± 0.2 | 12 ± 10 | 5.8 ± 0.4 | −1.3 ± 0.6⁀ | 4 | 4.9 ± 0.1 | 47 ± 6** | 5.1 ± 0.1 | −1.4 ± 0.2⁀ | 4 |
| Cmpd43 | 7.1 ± 0.4 | 27 ± 20 | 7.1 ± 0.3 | 0.0 | 3 | 6.6 ± 0.1*### | 66 ± 6*** | 6.5 ± 0.1 | 0.0 | 4 |

TABLE 9

BIDI-001 exhibits biased signalling away from Ca2+ i at FPR1 in CHO cells in vitro and cardioprotection both in isolated cardio-myocytes in vitro & intact heart subjected to MI in vivo. ND = Not detectable.

| Candidate | hFPR1-FlpInCHO cells in vitro potency (pEC$_{50}$) | | | Mice in vitro | | Cardioprotection | | |
|---|---|---|---|---|---|---|---|---|
| | pERK1/2 | Ca$^{2+}{}_i$ | Bias | $t_{1/2}$ (h) | $T_{max}$ (h) | Infarct size | Inflammation | Adverse remodelling |
| Cmpd43 | 7.17 ± 0.24 | 7.96 ± 0.19 | No | 3.8 | 2.0 | ↔ | ↔ | ↔ |
| BIDI-001 | 5.69 ± 0.21 | 5.32 ± 0.43 | Strong | 7.6 | 0.5 | ↓↓ | ↓↓ | ↓↓ |
| 10396 | 6.17 ± 0.08 | 4.48 ± 0.72 | Strong | 11.7 | 1.0 | ↓↓ | ND | ND |
| 10394 | 6.77 ± 0.08 | 6.39 ± 0.11 | Slight | 9.5 | 0.3 | ↔ | ND | ND |

TABLE 10

Active compounds tested.

| Reference Number | Structure | ERK | | Calcium | |
|---|---|---|---|---|---|
| | | pEC50 | Rmax | pEC50 | Rmax |
| MIPS008744 | (3-OMe-benzyl pyridazinone, 4-Cl anilide) | 5.47 ± 0.12 | 95 ± 5 | ND | 20 ± 5 |
| MIPS-0008745 | (3-OMe-benzyl pyridazinone, 3-F anilide) | 5.12 ± 0.38 | 50 ± 4 | ND | ND |
| MIPS-0008749 | (3-OMe-benzyl pyridazinone, 4-F anilide) | 5.07 ± 0.18 | 57 ± 2 | ND | ND |
| MIPS-0008750 | (3-OMe-benzyl pyridazinone, benzodioxole anilide) | 5.24 ± 0.16 | 74 ± 7 | ND | 26 ± 6 |
| MIPS-0008853 | (4-OMe-benzyl pyridazinone, 4-Br anilide) | 5.58 ± 0.14 | 81 ± 6 | ND | 26 ± 6 |

TABLE 10-continued

Active compounds tested.

| Reference Number | Structure | ERK pEC50 | ERK Rmax | Calcium pEC50 | Calcium Rmax |
|---|---|---|---|---|---|
| MIPS-0008854 | 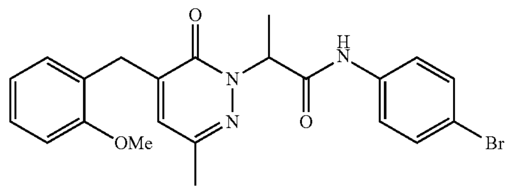 [SMILES: COc1ccccc1Cc1cc(C)nn(C(C)C(=O)Nc2ccc(Br)cc2)c1=O] | 6.07 ± 0.11 | 76 ± 3 | ND | 26 ± 9 |
| MIPS-0008855 | 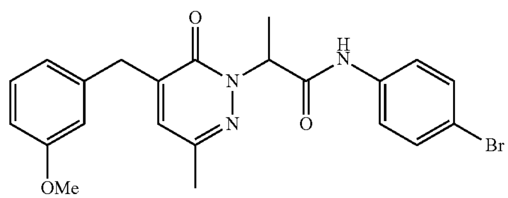 [SMILES: COc1cccc(Cc2cc(C)nn(C(C)C(=O)Nc3ccc(Br)cc3)c2=O)c1] | 5.22 ± 0.13 | 88 ± 8 | ND | 22 ± 6 |
| MIPS-0008856 | 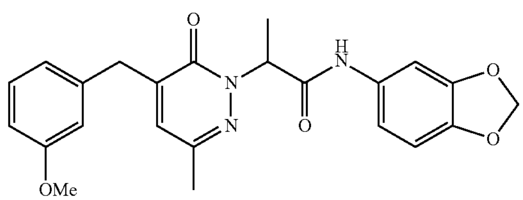 [SMILES: COc1cccc(Cc2cc(C)nn(C(C)C(=O)Nc3ccc4c(c3)OCO4)c2=O)c1] | 4.90 ± 1.27 | 64 ± 4 | ND | 19 ± 3 |
| MIPS-0008857 | 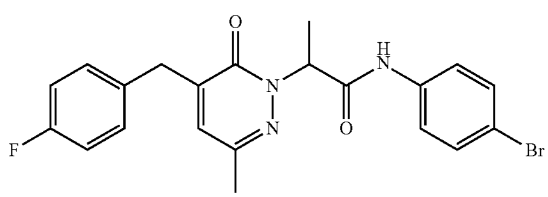 [SMILES: Cc1cc(Cc2ccc(F)cc2)c(=O)n(C(C)C(=O)Nc2ccc(Br)cc2)n1] | 5.74 ± 0.13 | 89 ± 1 | ND | 5 ± 1 |
| MIPS-0008858 | 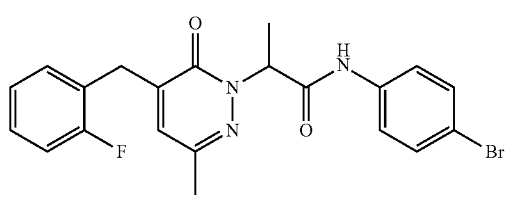 [SMILES: Cc1cc(Cc2ccccc2F)c(=O)n(C(C)C(=O)Nc2ccc(Br)cc2)n1] | 5.75 ± 0.12 | 91 ± 8 | ND | 8 ± 2 |
| MIPS-0008859 | 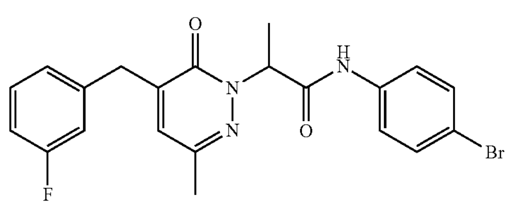 [SMILES: Cc1cc(Cc2cccc(F)c2)c(=O)n(C(C)C(=O)Nc2ccc(Br)cc2)n1] | 5.68 ± 16 | 93 ± 7 | ND | 18 ± 3 |
| MIPS-0008860 (R-enantiomer for 17b) | 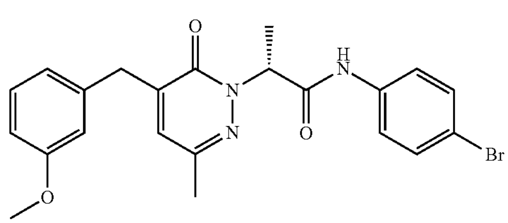 [SMILES: COc1cccc(Cc2cc(C)nn([C@H](C)C(=O)Nc3ccc(Br)cc3)c2=O)c1] | 6.13 ± 0.13 | 82 ± 9 | 5.07 ± 0.15 | 39 ± 2 |

TABLE 10-continued

Active compounds tested.

| Reference Number | Structure | ERK | | Calcium | |
|---|---|---|---|---|---|
| | | pEC50 | Rmax | pEC50 | Rmax |
| MIPS-0008861 (S-enantiomer for 17b) | 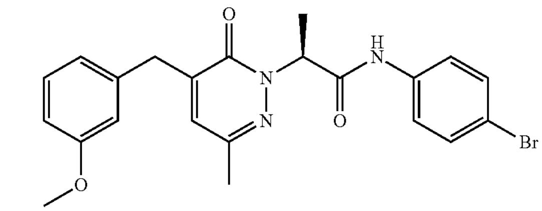 [SMILES: COc1cccc(Cc2cc(C)nn([C@@H](C)C(=O)Nc3ccc(Br)cc3)c2=O)c1] | 5.76 ± 0.19 | 80 ± 9 | 4.41 ± 1.49 | 16 ± 4 |
| MIPS-0010384 | 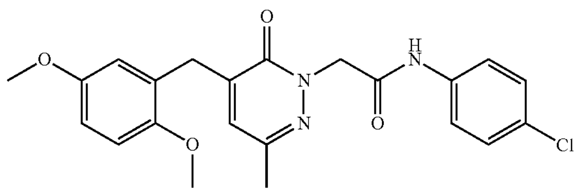 [SMILES: COc1ccc(OC)c(Cc2cc(C)nn(CC(=O)Nc3ccc(Cl)cc3)c2=O)c1] | 5.00 ± 0.37 | 77 ± 3 | 5.22 ± 0.22 | 19 ± 2 |
| MIPS-0010392 | 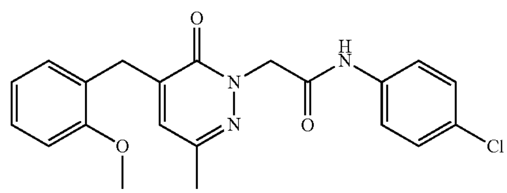 [SMILES: COc1ccccc1Cc1cc(C)nn(CC(=O)Nc2ccc(Cl)cc2)c1=O] | 5.91 ± 0.13 | 81 ± 2 | 4.74 ± 0.53 | 17 ± 3 |
| MIPS-0010394 | 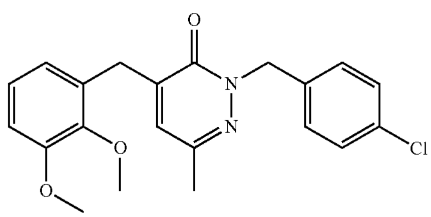 [SMILES: COc1cccc(Cc2cc(C)nn(Cc3ccc(Cl)cc3)c2=O)c1OC] | 6.77 ± 0.08 | 82 ± 5 | 6.39 ± 0.11 | 38 ± 2 |
| MIPS-0010395 | 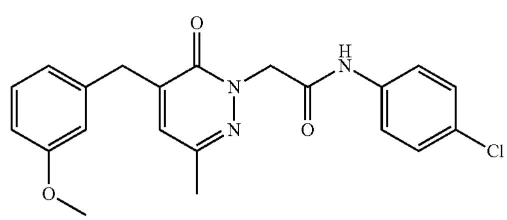 [SMILES: COc1cccc(Cc2cc(C)nn(CC(=O)Nc3ccc(Cl)cc3)c2=O)c1] | 5.65 ± 0.13 | 79 ± 4 | ND | ND |
| MIPS-0010396 | 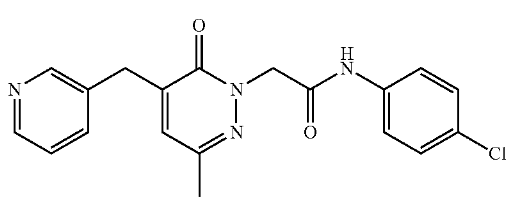 [SMILES: Cc1cc(Cc2cccnc2)c(=O)n(CC(=O)Nc2ccc(Cl)cc2)n1] | 6.17 ± 0.08 | 76 ± 2 | 4.48 ± 0.72 | 22 ± 2 |
| MIPS-0010397 | 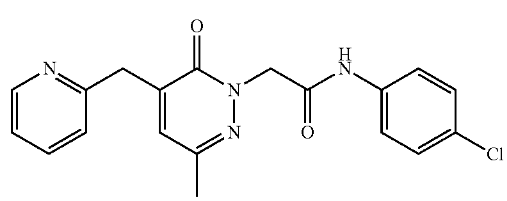 [SMILES: Cc1cc(Cc2ccccn2)c(=O)n(CC(=O)Nc2ccc(Cl)cc2)n1] | 5.99 ± 0.15 | 74 ± 3 | ND | 18 ± 8 |

TABLE 10-continued

Active compounds tested.

| Reference Number | Structure | ERK | | Calcium | |
|---|---|---|---|---|---|
| | | pEC50 | Rmax | pEC50 | Rmax |
| MIPS-0014051 | | 5.30 ± 0.12 | 79 ± 9 | ND | ND |
| MIPS-0014052 | | 5.10 ± 0.23 | 64 ± 6 | ND | 13 ± 3 |
| MIPS-0014053 | | 5.72 ± 0.09 | 78 ± 13 | ND | ND |
| MIPS-0014055 | | 5.75 ± 0.16 | 94 ± 11 | ND | 11 ± 2 |
| MIPS-0014057 | | 6.22 ± 0.18 | 91 ± 4 | 5.34 ± 0.18 | 45 ± 10 |
| MIPS-0014058 | | 5.94 ± 0.10 | 87 ± 1 | 5.30 ± 0.19 | 32 ± 1 |
| MIPS-0014071 | | 5.58 ± 0.02 | 78 ± 2 | 5.55 ± 0.08 | 48 ± 7 |

ND = Not detectable.

BIBLIOGRAPHY

Armstrong et al., *JAMA* 2007, 297, 43-51;
Arumugam, T. V., et al., *Shock.* 2009, 32(1), 4-16;
S. M. Berge et al., *J. Pharm. Sci.*, 1977, 66, 1-19;
Burli R W, Xu H, Zou X et al. *Bioorg Med Chem Lett* 2006; 16:3713-8.
Cha, J., et al., *Ann. Thorac. Surg.* 2008, 85(5), 1678-85;
Chao, W., *Am. J. Physiol. Heart Circ. Physiol.* 2009, 296(1), H1-12;
Chen, G. Y. and G. Nunez, *Nat. Rev. Immunol.* 2010, 10(12), 826-37;
Christopoulos A, Kenakin T. *Pharmacol Rev* 2002; 54:323-74.
Cilibrizzi et al. in *J. Med. Chem.* 2009, 52, 5044-5057;
Cilibrizzi et al., *Bioorg. Med. Chem.* 2012, 20, 3781-3792;
Crocetti et al., *Drug Dev. Res.* 2013, 74, 259-271;
Giovannoni et al., *Eur. J. Med. Chem.* 2013, 65, 512-528;
Egleton and Davis, *Peptides,* 1997, 18, 1431-1439;
Fleetwood et al., *J Immunol.* 2007, 178, 5245-5252;
Gao, X-M et al., *J. Mol. Cell. Cardiol.* 2000, 32(9), 1679-1686;
Gao X-M, et. al., *J. Mol. Cell. Cardiol.* 2011, 50(6), 991-999;
Granger et al., *Circulation.* 2003, 108, 1184-1190;
House, H. O., *Modern Synthetic Reactions* 2nd Edition (W. A. Benjamin, Inc., Menlo Park, 1972);
Huynh K, Kiriazis H, Du X J et al. *Diabetologia* 2012; 55:1544-53.
Hwang et al., *J. Am. Coll. Cardiol.* 2001, 38, 1546-1553;
Irvine J C, Ganthavee V, Love J E et al. *PloS One* 2012; 7:e44481.
Irvine, J. C. et al., *Am. J. Physiol.* 2013, 305(3), H365-377;
Kenakin T, Watson C, Muniz-Medina V, Christopoulos A, Novick S. *ACS Chem Neurosci* 2012; 3:193-203.
Keov, P. et al., *J. Biol. Chem.* 2014, 289(34), 23817-37;
Langer, *Science,* 1990, 249, 1527-1533;
Larock, R. C., *Comprehensive Organic Transformations* (VCH, New York, 1989);
Le Y. Y. et al., *J. Immunol.* 1999, 163(12), 6777-84;
Lefer and Granger, *Am. J. Med.* 2000, 109, 315-323;
Liotta, D. C. and Volmer, M., eds, *Organic Syntheses Reaction Guide* (John Wiley & Sons, Inc., New York, 1991);
Mahaffey et al. *Circulation.* 2003, 108, 1176-1183;
March, J., *Advanced Organic Chemistry,* 3rd Edition (John Wiley & Sons, New York, 1985);
May L T, Self T J, Briddon S J, Hill S J. *Mol Pharmacol* 2010; 78:511-23.
Monden et al., *Cardiovasc Res.* 2007, 73, 794-805;
Prossnitz, E. R., and R. D. Ye. *Pharmacol. Ther.* 1997, 74(1), 73-102; *Remington's Pharmaceutical Sciences, 17th* ed., Mack Publishing Company, Easton, Pa., 1985;
Simpkins, N. S., ed. 100 *Modern Reagents* (The Royal Society of Chemistry, London, 1989);
Stewart G D et al., *Int. J. Cancer* 2009, 124(1), 223-232;
Sun et al., *Circulation.* 2004, 110, 3221-3228;
Suzuki et al., *Circulation.* 2001, 104, I308-I303;
Tavener, S. A. and P. Kubes, *Am. J. Physiol. Heart Circ. Physiol.* 2006, 290(2), H800-6;
Timmers et al., *J. Am. Coll. Cardiol.* 2009, 53, 501-510;
Valant C et al., *PNAS* 2014, 111(12), 4614-19;
Ye, R. D. et al., *Pharmacol. Rev.* 2009, 61(2), 119-161.

The invention claimed is:
1. A method of minimising the extent of ischaemia-induced myocardial tissue damage or ischaemia-reperfusion-induced myocardial tissue damage in a mammal comprising administering to said mammal an effective amount of a compound of structure (I):

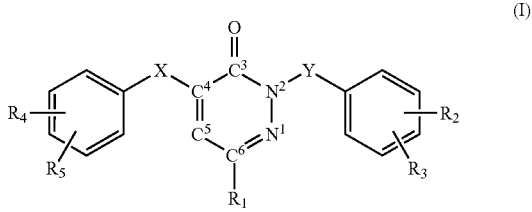

or a pharmaceutically acceptable salt, solvate or stereoisomer thereof, wherein (a) X is $CH_2$;
  Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
  wherein $R_6$ is H;
    $R_7$ is $CH_3$, $C_2H_5$, n-$C_3H_7$, i-$C_3H_7$, n-$C_4H_9$, or $C_6H_5$;
  or
    $R_6$ is $CH_3$;
    $R_7$ is $C_2H_5$ or $CH_3$; and
  $R_1$ is $CH_3$;
or (b) X is $CH_2$;
  Y is $CH_2CONH$; and
  $R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or (c) X is NHCO or NHCONH;
  Y is $CH_2$; and
  $R_1$ is $CH_3$;
or (d) X is NH;
  Y is $CH_2CONH$; and
  $R_1$ is $CH_3$;
or (e) X is NHCO or CO;
  Y is $CH_2CONH$; and
  $R_1$ is $CH_3$;
or (f) X is $CH_2$;
  Y is $CH_2CO$;
    wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and
  $R_1$ is $CH_3$;
or (g) X is NHCONH, NHCO, or NH;
  Y of structure (I) is not present and instead the phenyl group substituted with $R_2$ and $R_3$ is directly bonded to the N2 of the pyridazinone ring; and
  $R_1$ is $CH_3$;
or (h) X is $CH_2$;
  Y is $CH_2CONH$;
    the phenyl group substituted with $R_4$ and $R_5$ and bonded to X of structure (I) is replaced with 3-Furyl, 3-Thienyl, 2-Thienyl, 1-Naphthyl, or 3-Pyridyl; and R₁ is CH₃;
or
(i) X and the phenyl group substituted with R₄ and R₅ are not present;
Y is CH₂CONH; and
R₁ is CH₃;
or
(j) X and the phenyl group substituted with R₄ and R₅ are not present;
Y is CH₂CONH;
R₁ is CH₃; and
the bond between C4 and C5 of the pyridazinone ring is a single bond;
or
(k) X is NH₂ and the phenyl group substituted with R₄ and R₅ is not present;
Y is CH₂CONH; and
R₁ is CH₃;
or
(l) X of structure (I) is not present and instead the phenyl group substituted with R₄ and R₅ is directly bonded to C4 of the pyridazinone ring;
Y is CH₂CONH; and
R₁ is CH₃;
or
(m) X is NH;
Y is CH₂CONH;
R₁ is CH₃; and
C5 is additionally substituted with COCH₃;
wherein R₂, R₃, R₄ and R₅ are independently hydrogen, halogen, alkyl, alkoxy, haloalkyl, haloalkoxy, alkylsulfide, cyano, nitro, or R₂ and R₃ and/or R₄ and R₅ is a bridged di-alkoxy group; and
wherein said compound is administered for a time and under conditions sufficient for said compound to induce cardiomyocyte FPR1 activation.

2. A method of minimising the extent of ischaemia-induced myocardial tissue damage or ischaemia-reperfusion-induced myocardial tissue damage in a mammal comprising administering to said mammal an effective amount of a compound of structure (I):

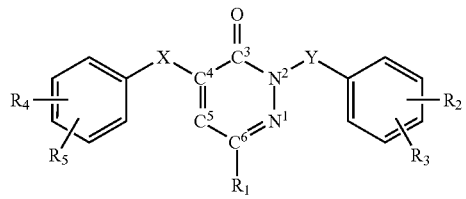
(I)

or a pharmaceutically acceptable salt, solvate or stereoisomer thereof, wherein
X is CH₂;
Y is CH₂CONH or CH(CH₃)CONH;
the phenyl group substituted with R₄ and R₅ and bonded to X of structure (I) is replaced with 2-Pyridyl, or is replaced with a moiety selected from the group consisting of 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro;
and
R₁ is CH₃;
wherein R₂ and R₃, are independently hydrogen, halogen, alkyl, alkoxy, haloalkyl, haloalkoxy, alkylsulfide, cyano, nitro, or R₂ and R₃ is a bridged di-alkoxy group;
and
wherein said compound is administered for a time and under conditions sufficient for said compound to induce cardiomyocyte FPR1 activation.

3. A method of therapeutically or prophylactically treating a condition characterised by ischaemia-induced myocardial tissue damage or ischaemia-reperfusion-induced myocardial tissue damage in a mammal comprising administering to said mammal an effective amount of the compound of structure (I):

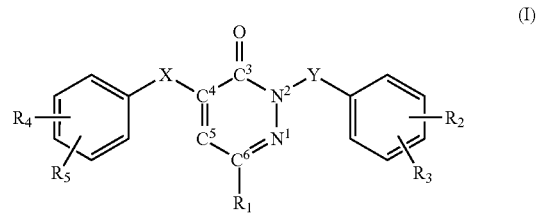
(I)

or a pharmaceutically acceptable salt, solvate or stereoisomer thereof, wherein
(a) X is CH₂;
Y is CH₂CONH, (CH₂)₂CONH, CH(CH₃)CONH, CH₂, CH₂CO, CH₂NHCONH, CH₂NHCO, (CH₂)₂O, (CH₂)₂NH, (CH₂)₂NHCONH, (CH₂)₂NHCO, CH₂CSNH, or C(R₆R₇)CONH;
wherein R₆ is H;
R₇ is CH₃, C₂H₅, n-C₃H₇, i-C₃H₇, n-C₄H₉, or C₆H₅;
or
R₆ is CH₃;
R₇ is C₂H₅ or CH₃; and
R₁ is CH₃;
or
(b) X is CH₂;
Y is CH₂CONH; and
R₁ is CH₃, H, CH₂CH₃, CH(CH₃)₂, C₆H₁₁, C₆H₅, 2-Thienyl, C₆H₄—OCH₃, C₆H₄—Cl, C₆H₄—CH₃, C₆H₄—F, or CH₂—C₆H₅;
or
(c) X is NHCO or NHCONH;
Y is CH₂; and
R₁ is CH₃;
or
(d) X is NH;
Y is CH₂CONH; and
R₁ is CH₃;
or
(e) X is NHCO or CO;
Y is CH₂CONH; and
R₁ is CH₃;
or
(f) X is CH₂;
Y is CH₂CO;
wherein the phenyl group substituted with R₂ and R₃ and bonded to Y of structure (I) is replaced with N-methyl piperazine, N(CH₃)—C₆H₄—Br, NHCH₂—C₆H₄—Br, or O—C₆H₄—Br; and R₁ is CH₃;
or
(g) X is NHCONH, NHCO, or NH;
Y of structure (I) is not present and instead the phenyl group substituted with R₂ and R₃ is directly bonded to the N2 of the pyridazinone ring; and
R₁ is CH₃;
or
(h) X is CH₂;
Y is CH₂CONH;
the phenyl group substituted with R₄ and R₅ and bonded to X of structure (I) is replaced with 3-Furyl, 3-Thienyl, 2-Thienyl, 1-Naphthyl, or 3-Pyridyl; and
R₁ is CH₃;
or
(i) X and the phenyl group substituted with R₄ and R₅ are not present;
Y is CH₂CONH; and
R₁ is CH₃;
or
(j) X and the phenyl group substituted with R₄ and R₅ are not present;
Y is CH₂CONH;
R₁ is CH₃; and
the bond between C4 and C5 of the pyridazinone ring is a single bond;
or
(k) X is NH₂ and the phenyl group substituted with R₄ and R₅ is not present;
Y is CH₂CONH; and
R₁ is CH₃;
or
(l) X of structure (I) is not present and instead the phenyl group substituted with R₄ and R₅ is directly bonded to C4 of the pyridazinone ring;
Y is CH₂CONH; and
R₁ is CH₃;
or
(m) X is NH;
Y is CH₂CONH;
R₁ is CH₃; and
C5 is additionally substituted with COCH₃;
wherein R₂, R₃, R₄ and R₅ are independently hydrogen, halogen, alkyl, alkoxy, haloalkyl, haloalkoxy, alkylsulfide, cyano, nitro, or R₂ and R₃ and/or R₄ and R₅ is a bridged di-alkoxy group; and
wherein said compound is administered for a time and under conditions sufficient for said compound to induce cardiomyocyte FPR1 activation.

4. A method of therapeutically or prophylactically treating a cardiac condition characterised by ischaemia-induced myocardial tissue damage or ischaemia-reperfusion-induced myocardial tissue damage in a mammal comprising administering to said mammal an effective amount of the compound of structure (I):

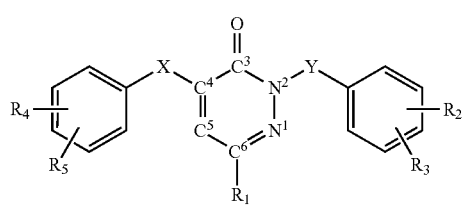

or a pharmaceutically acceptable salt, solvate or stereoisomer thereof, wherein
(h) X is CH₂;
Y is CH₂CONH or CH(CH₃)CONH;
the phenyl group substituted with R₄ and R₅ and bonded to X of structure (I) is replaced with 2-Pyridyl, or is replaced with a moiety selected from the group consisting of 3-Furyl, 3-Thienyl, 2-Thienyl, 1-Naphthyl, 2-Pyridyl or 3-Pyridyl, each of which is optionally substituted with one or more of halogen, alkyl, alkoxy, haloalkyl, haloalkoxy, alkylsulfide, cyano or nitro; and
R₁ is CH₃;
wherein R₂ and R₃ are independently hydrogen, halogen, alkyl, alkoxy, haloalkyl, haloalkoxy, alkylsulfide, cyano, nitro, or R₂ and R₃ is a bridged di-alkoxy group; and
wherein said compound is administered for a time and under conditions sufficient for said compound to induce cardiomyocyte FPR1 activation.

5. The method according to claim 1, wherein said tissue damage is loss of cellular viability and contractile function.

6. The method according to claim 1, wherein said tissue damage is myocardial infarction-induced tissue damage.

7. The method according to claim 1, wherein said myocardial infarction-induced tissue damage is acute myocardial infarction-induced tissue damage.

8. The method according to claim 1, wherein said tissue damage is selected from the group consisting of myocardial inflammation, loss of contractive functioning, cellular necrosis, cellular apoptosis, fibrosis, myocardial tissue remodelling, infarct size, and left ventricular functioning.

9. The method according to claim 1, wherein said mammal is a human.

10. The method according to claim 1, wherein the compound of structure (I) is:

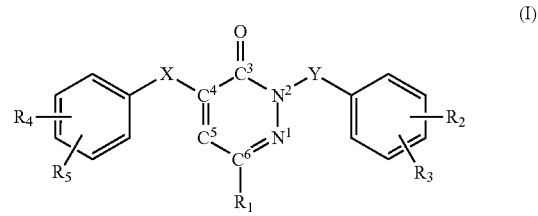

wherein
(g) X is CH₂;
Y is CH(CH₃)CONH
R₁ is CH₃;
wherein R₂, R₃, R₄ and R₅ are independently hydrogen, halogen, alkyl, alkoxy, haloalkyl, haloalkoxy, alkylsulfide, cyano, nitro, or R₂ and R₃ and/or R₄ and R₅ is a bridged di-alkoxy group;
or a pharmaceutically acceptable salt, solvate or stereoisomer thereof.

11. The method according to claim 1, wherein the compound of structure (I) is:

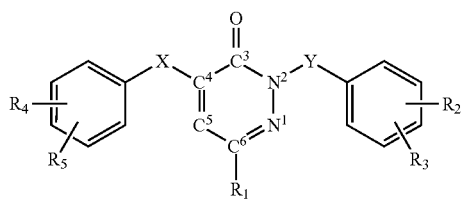

wherein
(h) X is CH₂;
Y is CH(CH₃)CONH
R₁ is CH₃;
wherein R₂ is hydrogen and R₃ is para-bromine, and R₄ and R₅ are independently hydrogen, halogen, alkyl, alkoxy, haloalkyl, haloalkoxy, alkylsulfide, cyano, or nitro;
or a pharmaceutically acceptable salt, solvate or stereoisomer thereof.

12. The method according to claim 1, wherein the compound of structure (I) is:

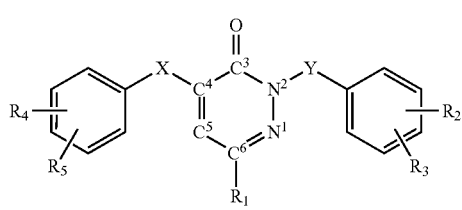

wherein
(i) X is CH₂;
Y is CH(CH₃)CONH
R₁ is CH₃;
wherein R₂ and R₃ are independently hydrogen, halogen, alkyl, alkoxy, haloalkyl, haloalkoxy, alkylsulfide, cyano, or nitro, and R₄ is hydrogen and R₅ is meta-methoxy;
or a pharmaceutically acceptable salt, solvate or stereoisomer thereof.

13. The method according to claim 1, wherein the compound of structure (I) is:

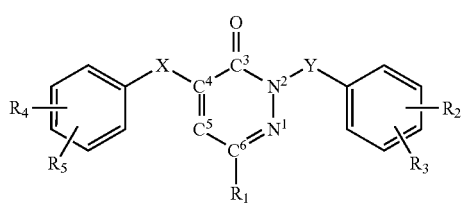

wherein
(j) X is CH₂;
Y is CH(CH₃)CONH
R₁ is CH₃;
wherein R₂ is hydrogen and R₃ is para-bromine, and R₄ is hydrogen and R₅ is meta-methoxy;
or a pharmaceutically acceptable salt, solvate or stereoisomer thereof.

14. The method according to claim 1, wherein the compound of structure (I) is selected from the group consisting of:

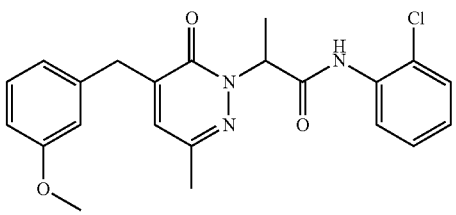
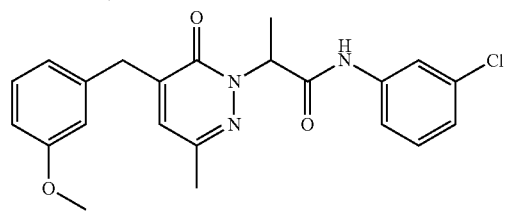
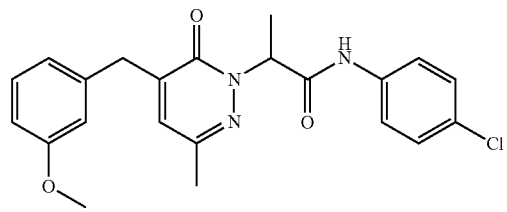
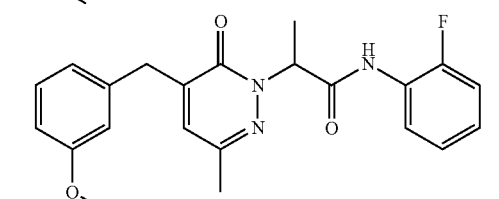
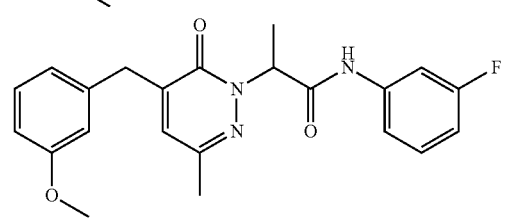
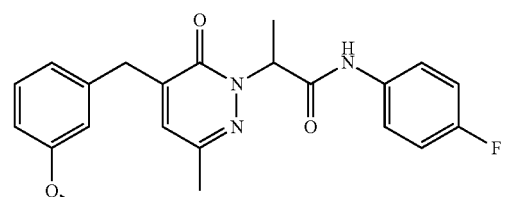
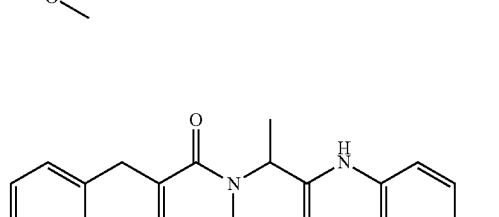

105
-continued
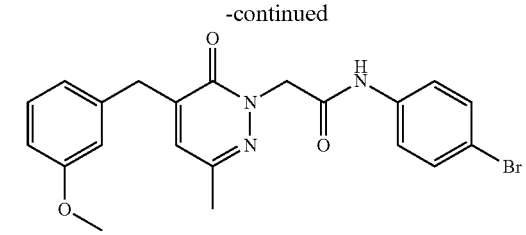
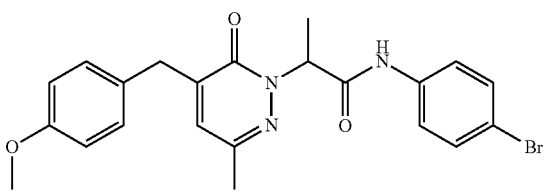
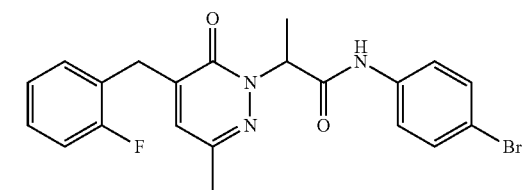
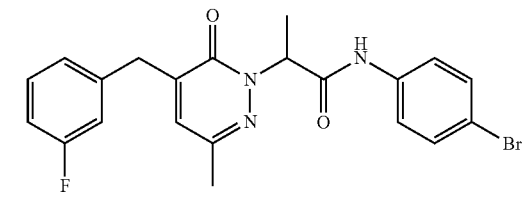
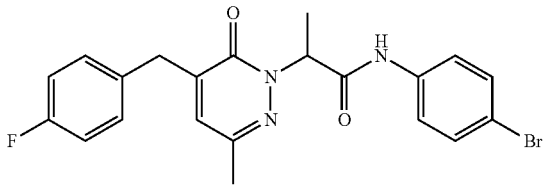
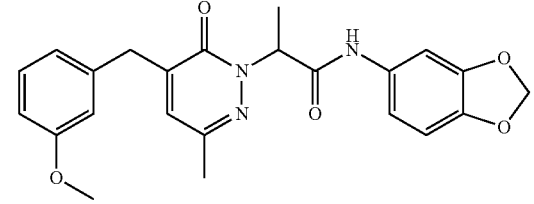
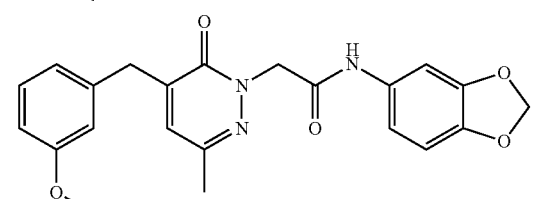
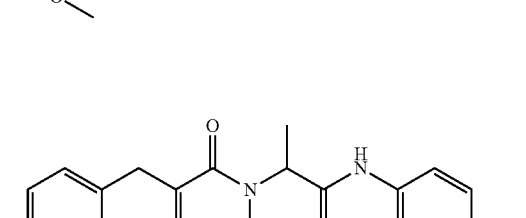
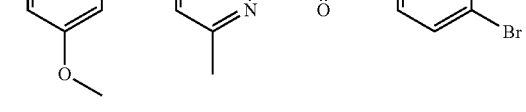
106
-continued
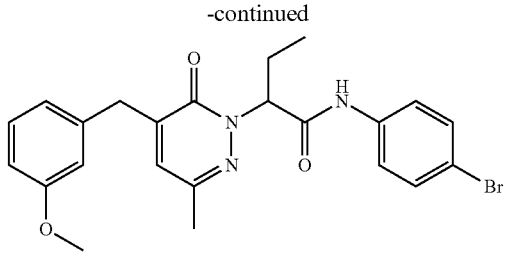
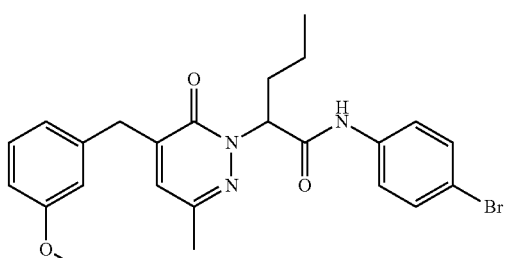
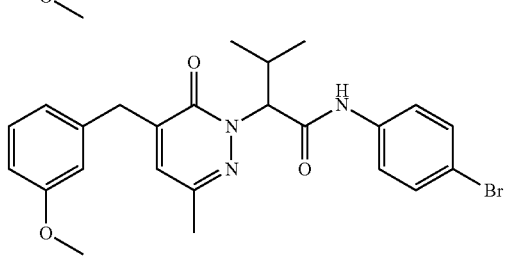
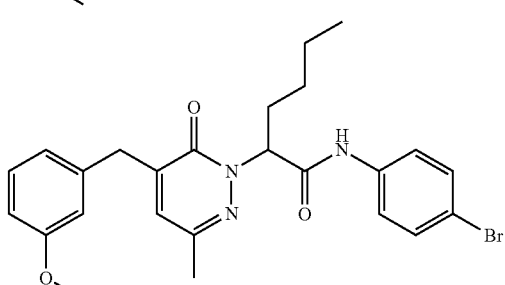
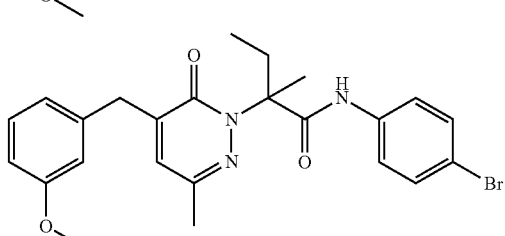
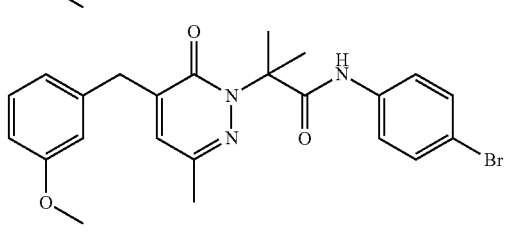
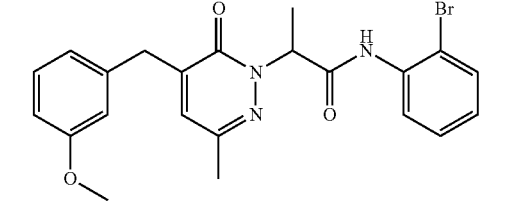

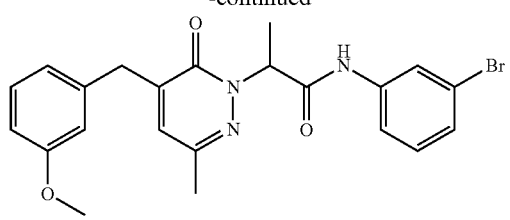
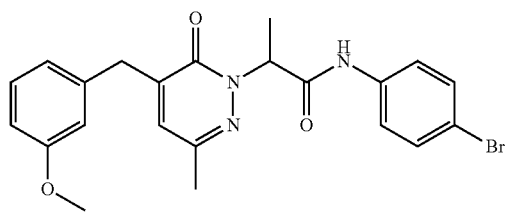
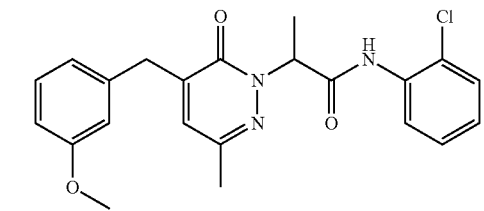
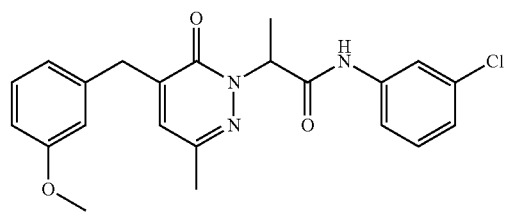
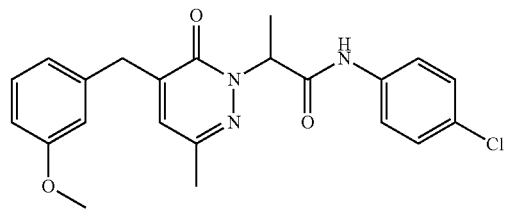
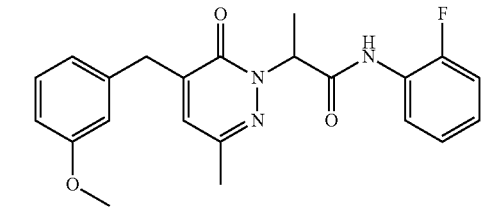
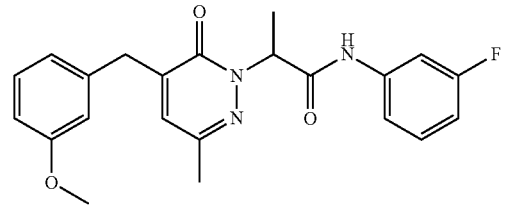
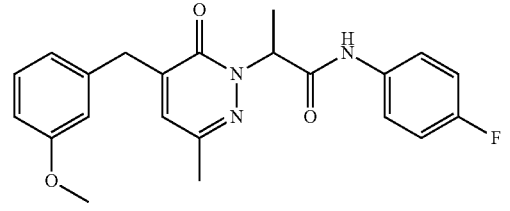
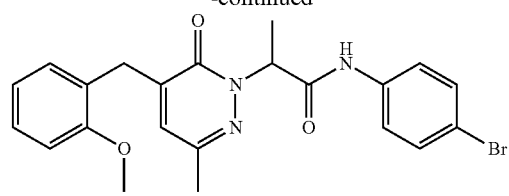
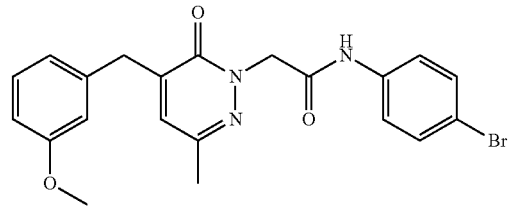
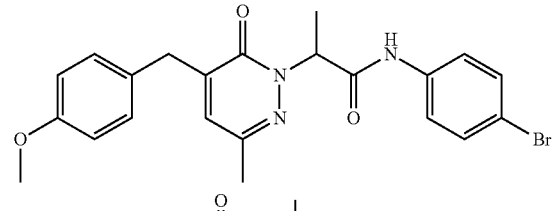
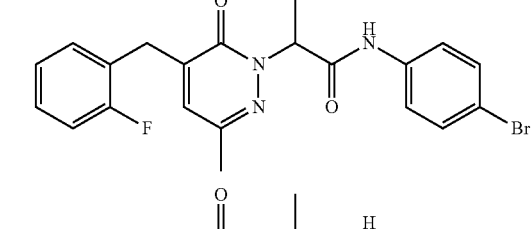
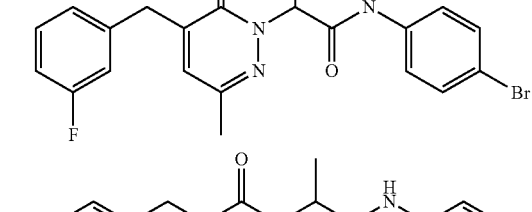
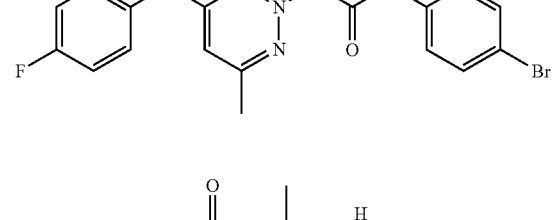
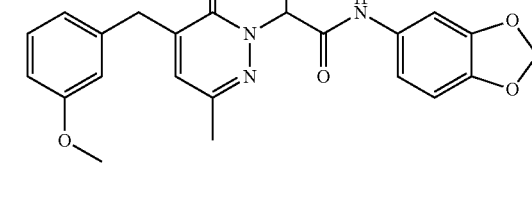
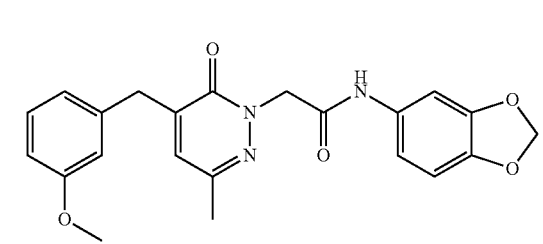

-continued
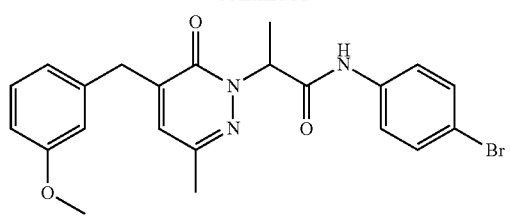
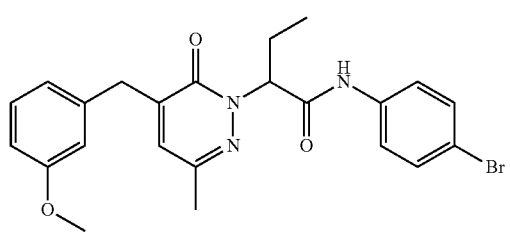
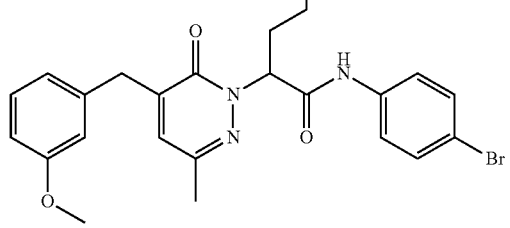
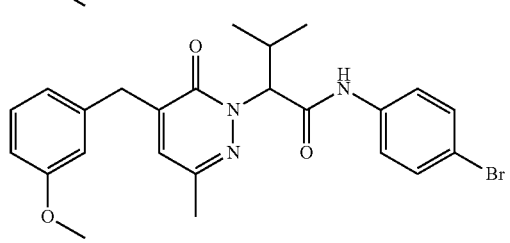
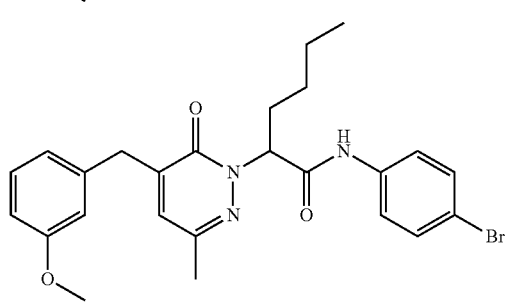
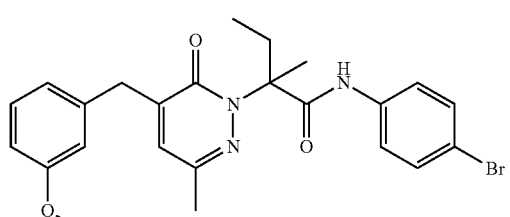
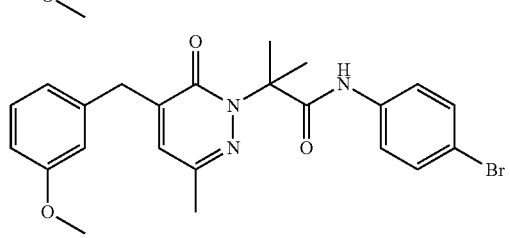
-continued
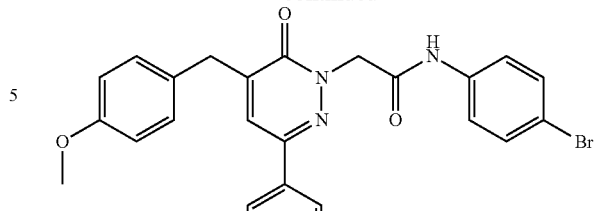
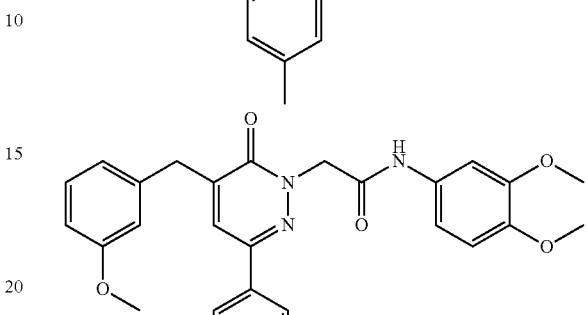
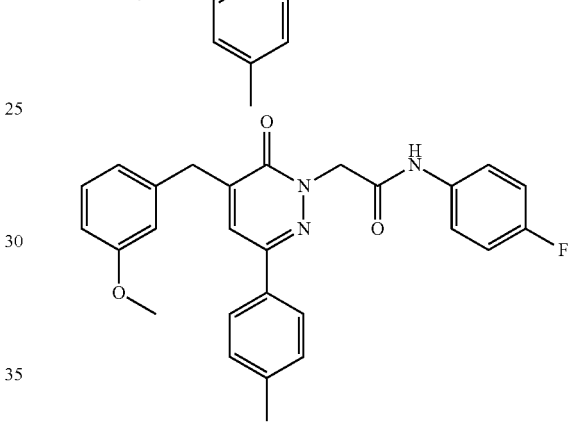
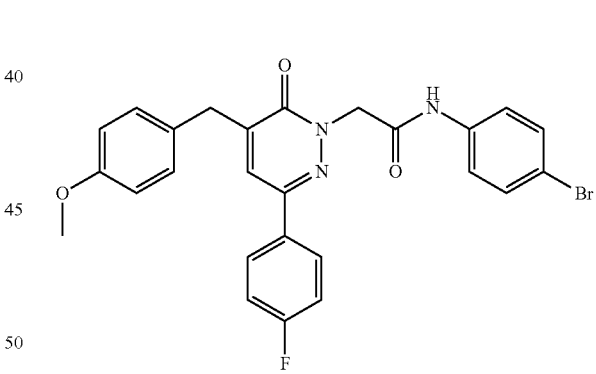
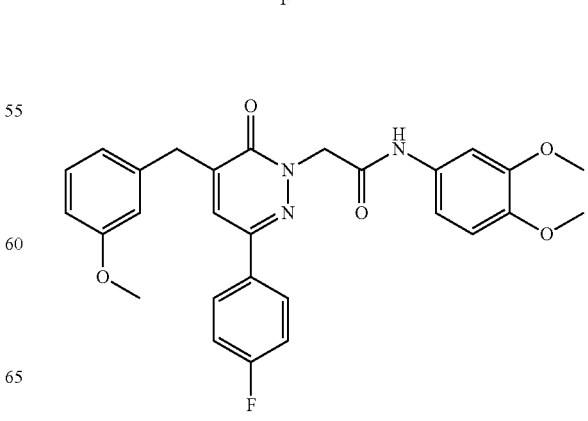

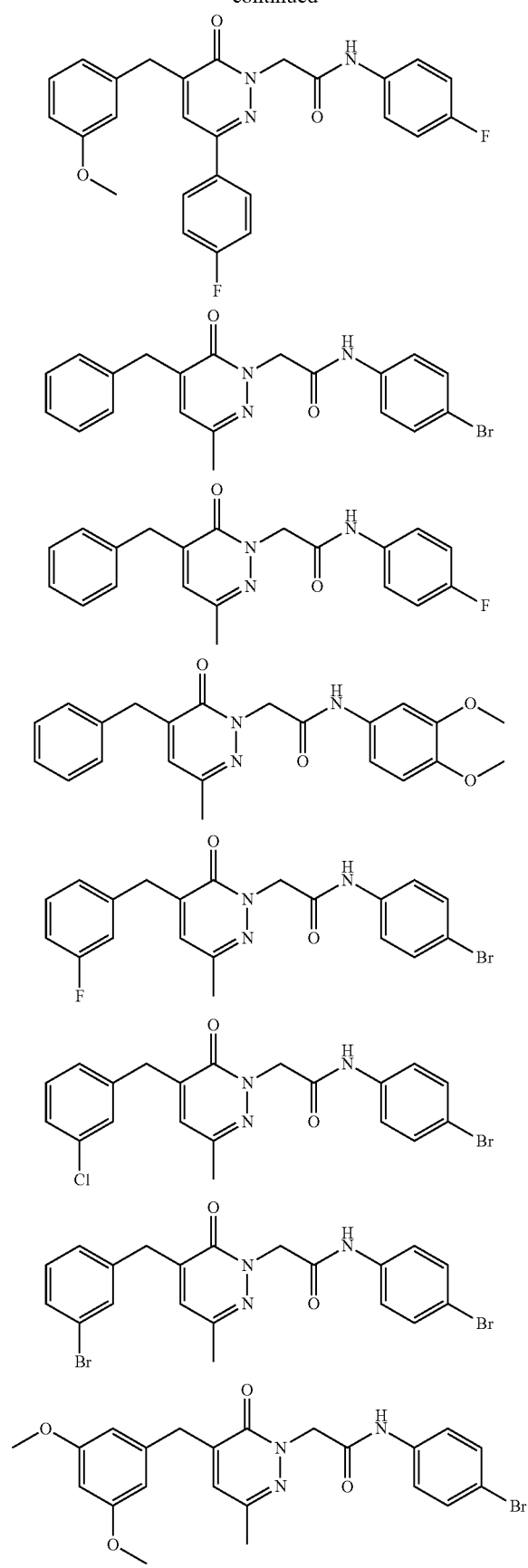
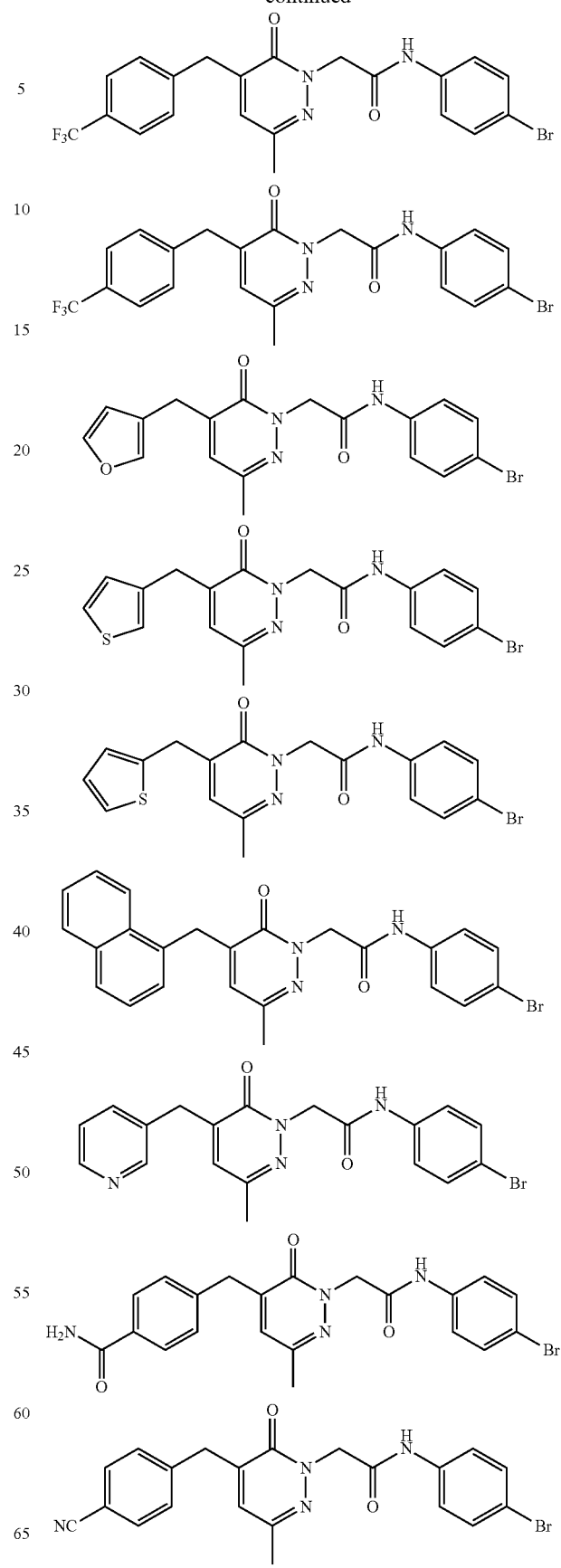

113
-continued
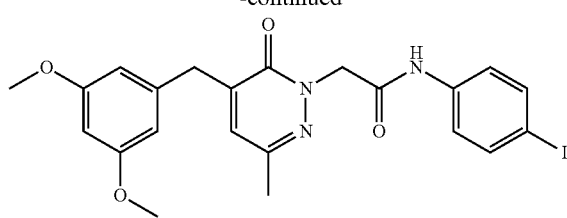
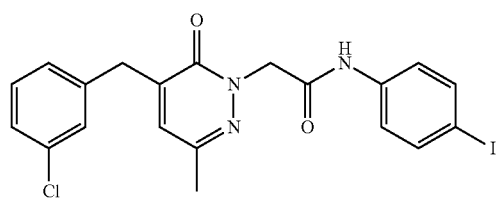
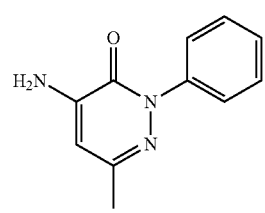
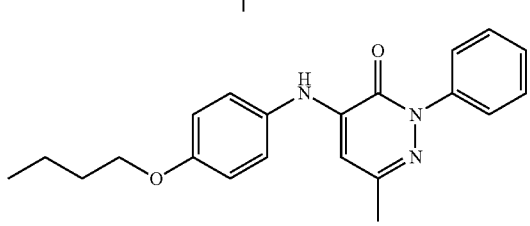
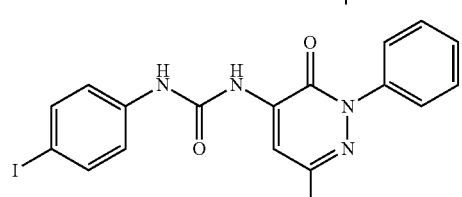
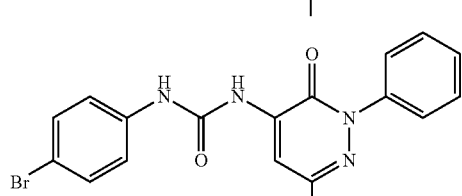
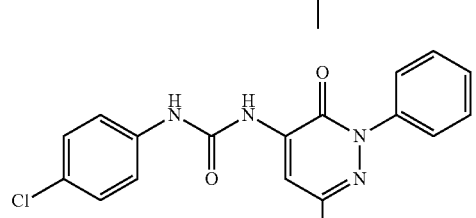
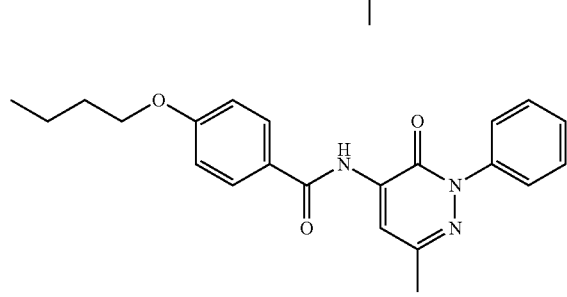
114
-continued
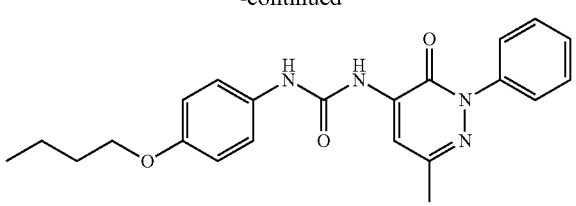
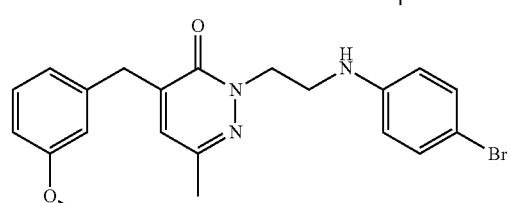
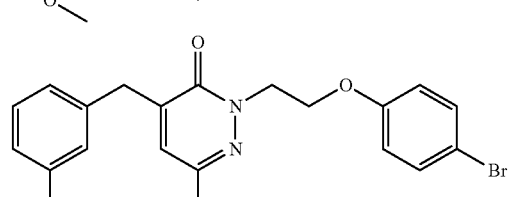
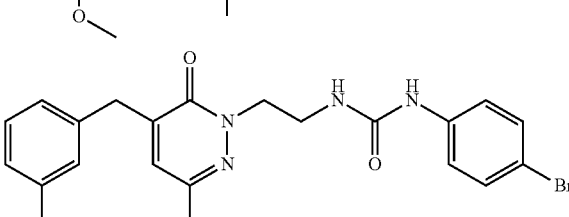
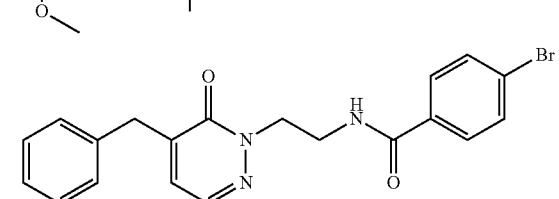
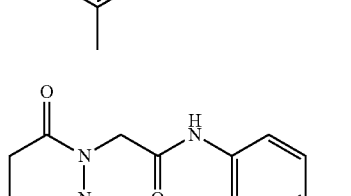
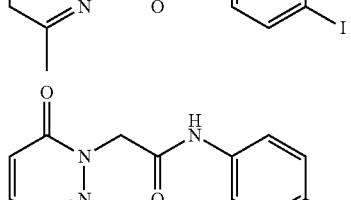
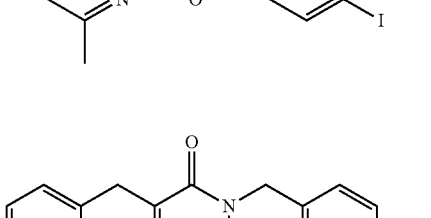

115
-continued
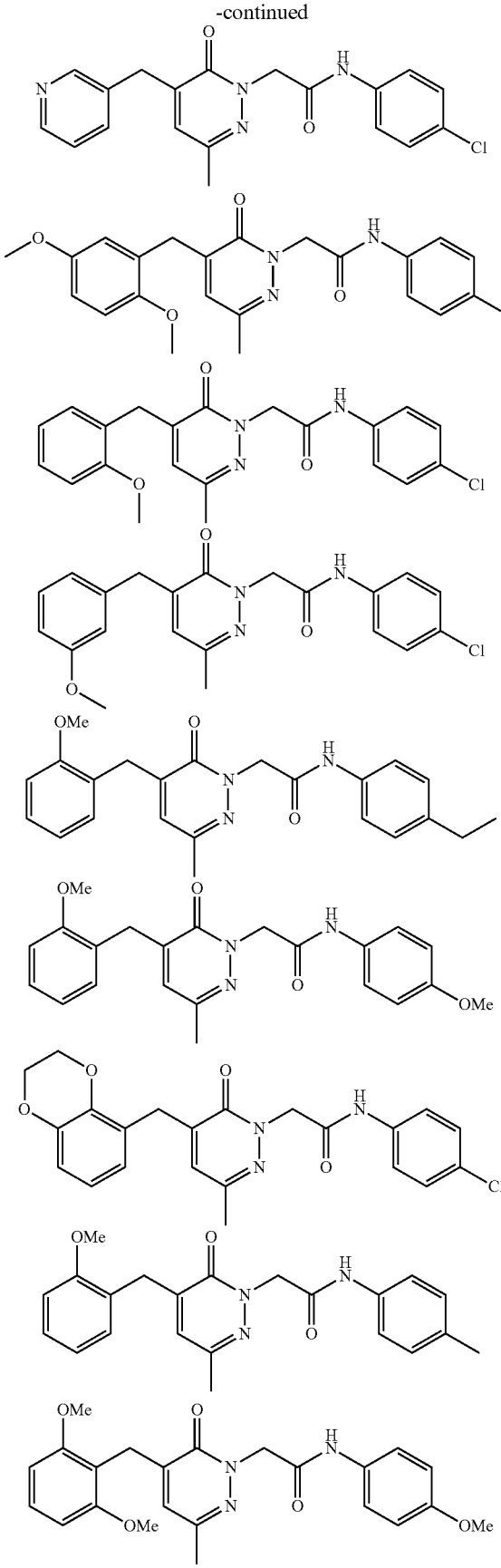
116
and pharmaceutically acceptable salts, solvates and stereoisomers thereof.
15. The method according to claim 1, wherein the compound of structure (I) is selected from the group consisting of:
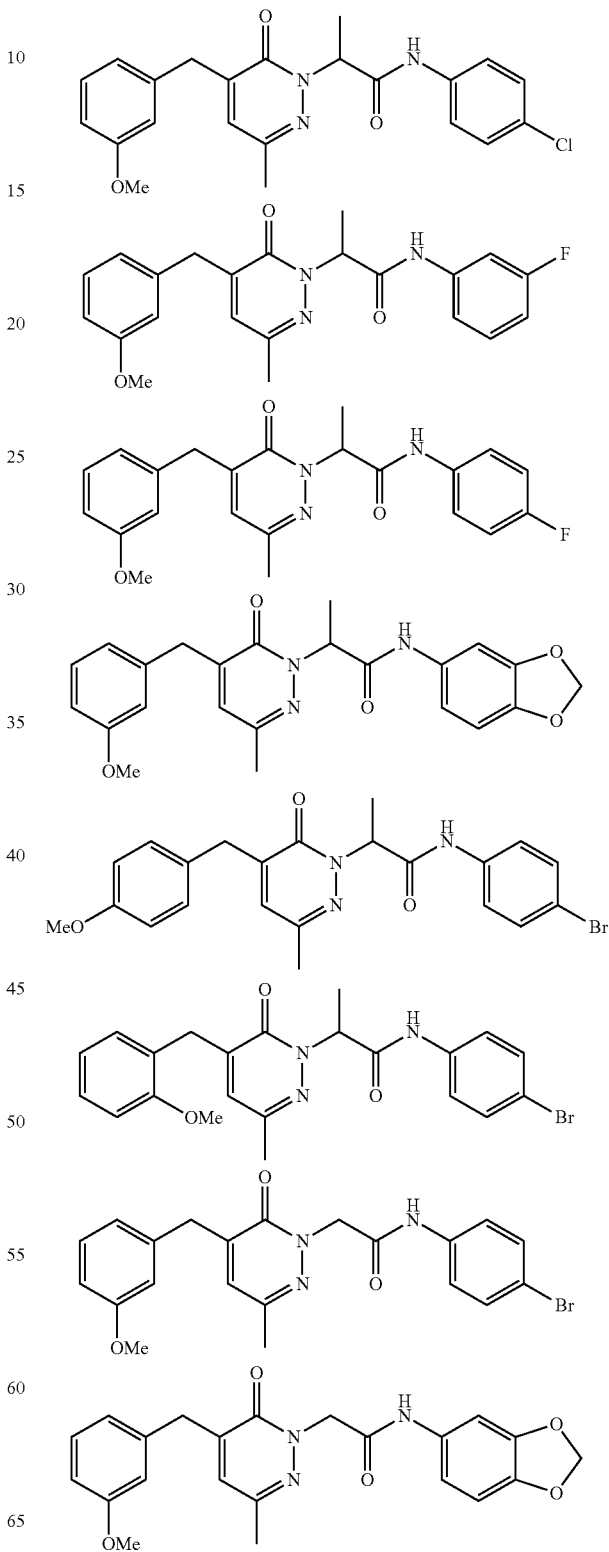

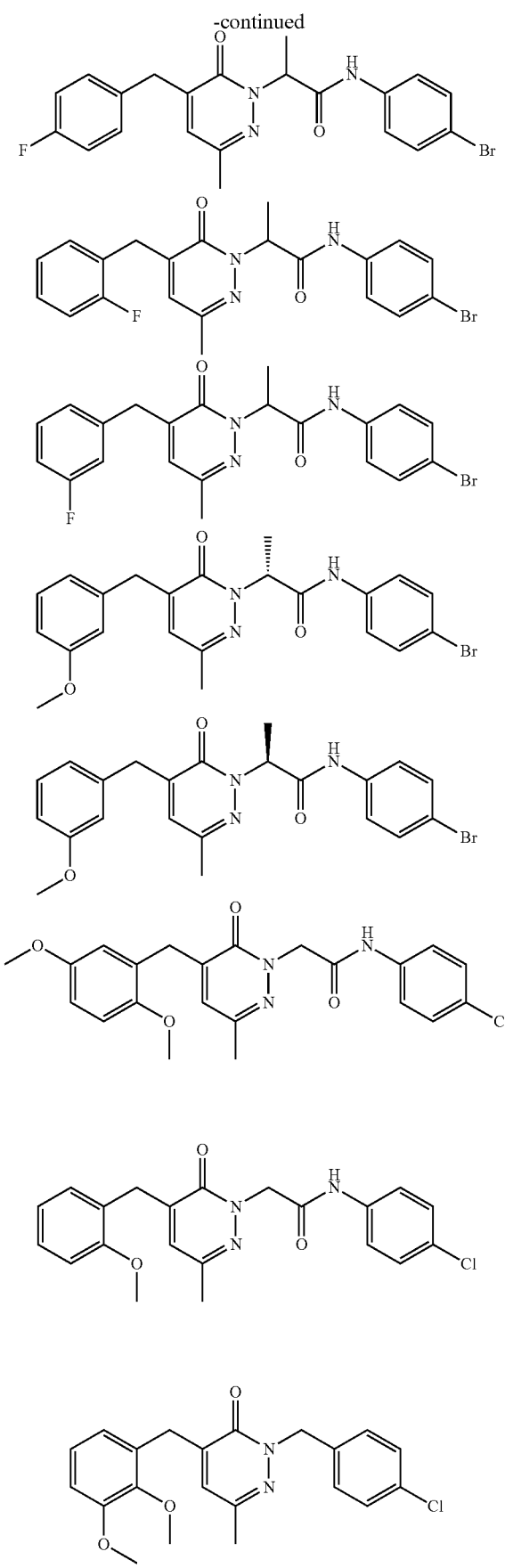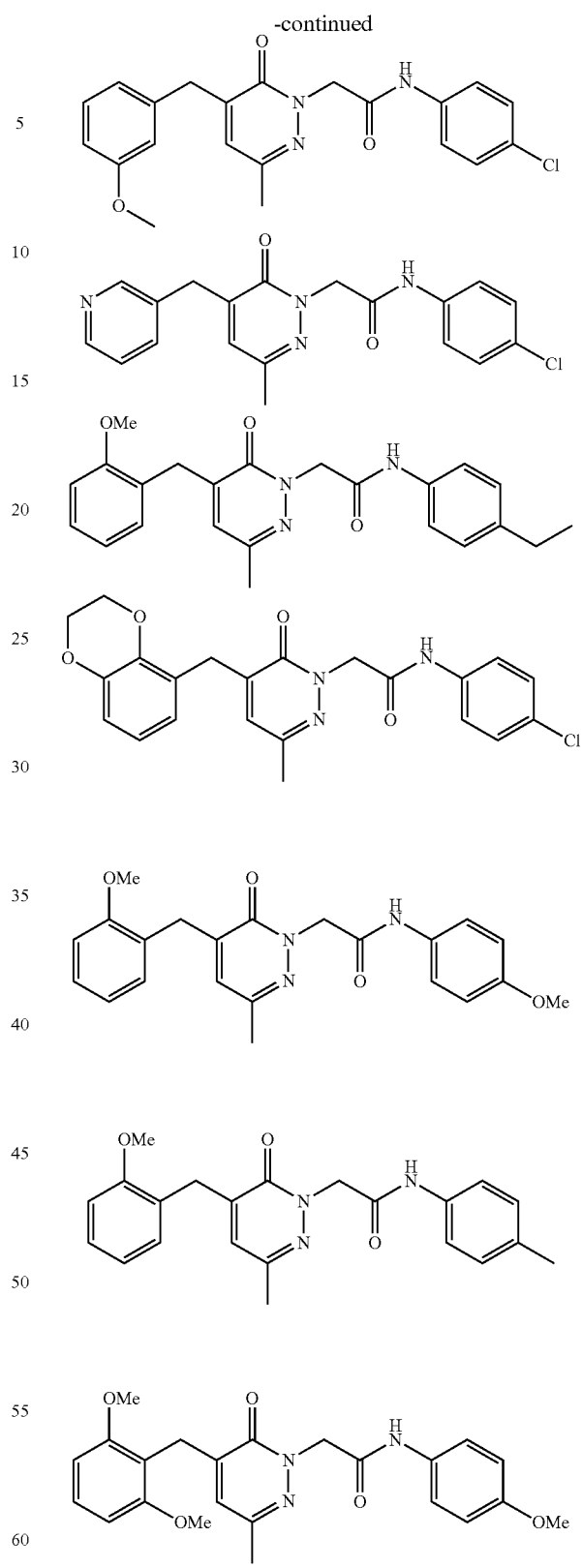
and pharmaceutically acceptable salts, solvates or stereoisomers thereof.
16. The method according to claim 1, wherein the compound of structure (I) is selected from the group consisting of:

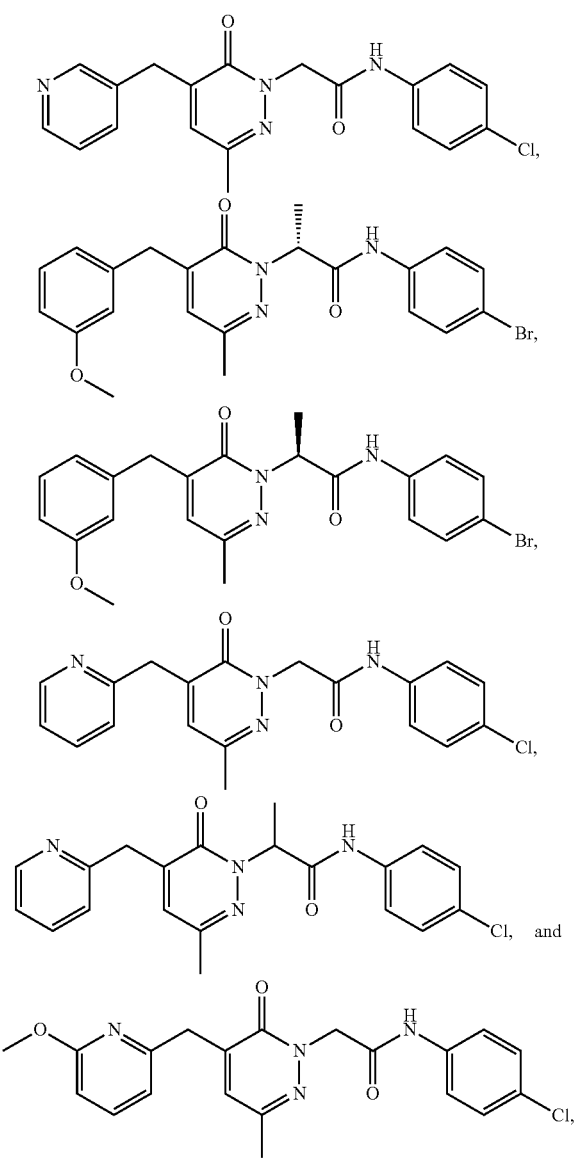

and pharmaceutically acceptable salts, solvates or stereoisomers thereof.

17. A method of treating ischaemia-induced myocardial tissue damage or ischaemia-reperfusion-induced myocardial tissue damage in a mammal comprising administering to said mammal an effective amount of a compound of structure (I):

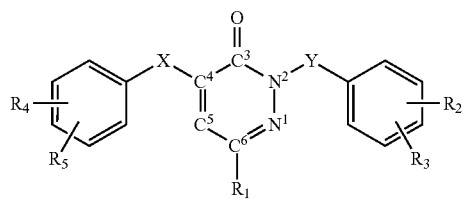

or a pharmaceutically acceptable salt, solvate or stereoisomer thereof, wherein (a) X is $CH_2$;
Y is $CH_2CONH$, $(CH_2)_2CONH$, $CH(CH_3)CONH$, $CH_2$, $CH_2CO$, $CH_2NHCONH$, $CH_2NHCO$, $(CH_2)_2O$, $(CH_2)_2NH$, $(CH_2)_2NHCONH$, $(CH_2)_2NHCO$, $CH_2CSNH$, or $C(R_6R_7)CONH$;
wherein $R_6$ is H;
$R_7$ is $CH_3$, $C_2H_5$, n-$C_3H_7$, i-$C_3H_7$, n-$C_4H_9$, or $C_6H_5$;
or
$R_6$ is $CH_3$;
$R_7$ is $C_2H_5$ or $CH_3$; and
$R_1$ is $CH_3$;
or (b) X is $CH_2$;
Y is $CH_2CONH$; and
$R_1$ is $CH_3$, H, $CH_2CH_3$, $CH(CH_3)_2$, $C_6H_{11}$, $C_6H_5$, 2-Thienyl, $C_6H_4$—$OCH_3$, $C_6H_4$—Cl, $C_6H_4$—$CH_3$, $C_6H_4$—F, or $CH_2$—$C_6H_5$;
or (c) X is NHCO or NHCONH;
Y is $CH_2$; and
$R_1$ is $CH_3$;
or (d) X is NH;
Y is $CH_2CONH$; and
$R_1$ is $CH_3$;
or (e) X is NHCO or CO;
Y is $CH_2CONH$; and
$R_1$ is $CH_3$;
or (f) X is $CH_2$;
Y is $CH_2CO$;
wherein the phenyl group substituted with $R_2$ and $R_3$ and bonded to Y of structure (I) is replaced with N-methyl piperazine, $N(CH_3)$—$C_6H_4$—Br, $NHCH_2$—$C_6H_4$—Br, or O—$C_6H_4$—Br; and
$R_1$ is $CH_3$;
or (g) X is NHCONH, NHCO, or NH;
Y of structure (I) is not present and instead the phenyl group
substituted with $R_2$ and $R_3$ is directly bonded to the N2 of the pyridazinone ring; and
$R_1$ is $CH_3$;
or (h) X is $CH_2$;
Y is $CH_2CONH$;
the phenyl group substituted with $R_4$ and $R_5$ and bonded to X of structure (I) is replaced with 3-Furyl, 3-Thienyl, 2-Thienyl, 1-Naphthyl, or 3-Pyridyl; and
$R_1$ is $CH_3$;
or (i) X and the phenyl group substituted with $R_4$ and $R_5$ are not present;
Y is $CH_2CONH$; and
$R_1$ is $CH_3$;
or (j) X and the phenyl group substituted with $R_4$ and $R_5$ are not present;
Y is $CH_2CONH$;
$R_1$ is $CH_3$; and
the bond between C4 and C5 of the pyridazinone ring is a single bond;

or
(k) X is NH$_2$ and the phenyl group substituted with R$_4$ and R$_5$ is not present;
Y is CH$_2$CONH; and
R$_1$ is CH$_3$;
or
(l) X of structure (I) is not present and instead the phenyl group substituted with R$_4$ and R$_5$ is directly bonded to C4 of the pyridazinone ring;
Y is CH$_2$CONH; and
R$_1$ is CH$_3$;
or
(m) X is NH;
Y is CH$_2$CONH;
R$_1$ is CH$_3$; and
C5 is additionally substituted with COCH$_3$;
wherein R$_2$, R$_3$, R$_4$ and R$_5$ are independently hydrogen, halogen, alkyl, alkoxy, haloalkyl, haloalkoxy, alkylsulfide, cyano, nitro, or R$_2$ and R$_3$ and/or R$_4$ and R$_5$ is a bridged di-alkoxy group; and
wherein said compound is administered for a time and under conditions sufficient for said compound to induce cardiomyocyte FPR1 activation.

18. The method according to claim 17, wherein the compound of structure (I) is:

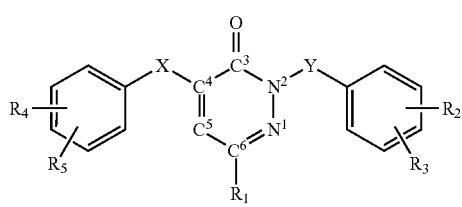

wherein
(g) X is CH$_2$;
Y is CH(CH$_3$)CONH
R$_1$ is CH$_3$;
wherein R$_2$, R$_3$, R$_4$ and R$_5$ are independently hydrogen, halogen, alkyl, alkoxy, haloalkyl, haloalkoxy, alkylsulfide, cyano, nitro, or R$_2$ and R$_3$ and/or R$_4$ and R$_5$ is a bridged di-alkoxy group;
or a pharmaceutically acceptable salt, solvate or stereoisomer thereof.

19. The method according to claim 17, wherein the compound of structure (I) is:

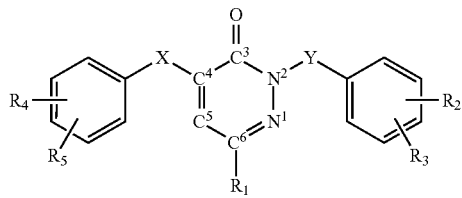

wherein
(h) X is CH$_2$;
Y is CH(CH$_3$)CONH
R$_1$ is CH$_3$;

wherein R$_2$ is hydrogen and R$_3$ is para-bromine, and R$_4$ and R$_5$ are independently hydrogen, halogen, alkyl, alkoxy, haloalkyl, haloalkoxy, alkylsulfide, cyano, or nitro;
or a pharmaceutically acceptable salt, solvate or stereoisomer thereof.

20. The method according to claim 17, wherein the compound of structure (I) is:

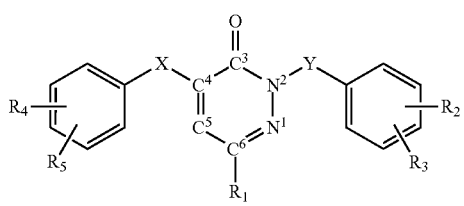

wherein
(i) X is CH$_2$;
Y is CH(CH$_3$)CONH
R$_1$ is CH$_3$;
wherein R$_2$ and R$_3$ are independently hydrogen, halogen, alkyl, alkoxy, haloalkyl, haloalkoxy, alkylsulfide, cyano, or nitro, and R$_4$ is hydrogen and R$_5$ is meta-methoxy;
or a pharmaceutically acceptable salt, solvate or stereoisomer thereof.

21. The method according to claim 17, wherein the compound of structure (I) is:

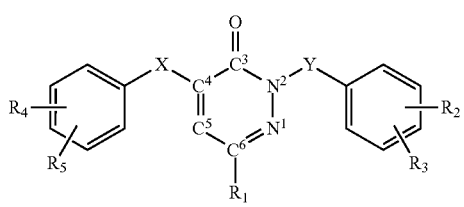

wherein
(j) X is CH$_2$;
Y is CH(CH$_3$)CONH
R$_1$ is CH$_3$;
wherein R$_2$ is hydrogen and R$_3$ is para-bromine, and R$_4$ is hydrogen and R$_5$ is meta-methoxy;
or a pharmaceutically acceptable salt, solvate or stereoisomer thereof.

22. The method according to claim 1, wherein the compound of structure (I) is:

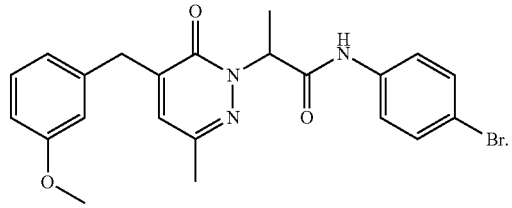 [SMILES: COc1cccc(Cc2cc(C)nn(C(C)C(=O)Nc3ccc(Br)cc3)c2=O)c1]

* * * * *